US012638452B2

(12) United States Patent
Haque et al.

(10) Patent No.: US 12,638,452 B2
(45) Date of Patent: May 26, 2026

(54) NANOPORE ASSEMBLIES AND USES THEREOF

(71) Applicant: Oxford Nanopore Technologies plc, Oxford (GB)

(72) Inventors: Farzin Haque, Long Island City, NY (US); Shaoying Wang, Piscataway, NJ (US)

(73) Assignee: Oxford Nanopore Technologies PLC, Oxford (GB)

( * ) Notice: Subject to any disclaimer, the term of this patent is extended or adjusted under 35 U.S.C. 154(b) by 1269 days.

(21) Appl. No.: 16/969,518

(22) PCT Filed: Feb. 11, 2019

(86) PCT No.: PCT/US2019/017432
§ 371 (c)(1),
(2) Date: Aug. 12, 2020

(87) PCT Pub. No.: WO2019/157424
PCT Pub. Date: Aug. 15, 2019

(65) Prior Publication Data
US 2020/0399693 A1      Dec. 24, 2020

Related U.S. Application Data

(60) Provisional application No. 62/629,604, filed on Feb. 12, 2018.

(51) Int. Cl.
B01J 20/32          (2006.01)
B01J 20/26          (2006.01)
(Continued)

(52) U.S. Cl.
CPC ....... G01N 33/6818 (2013.01); C12Q 1/6825 (2013.01); G01N 33/54373 (2013.01);
(Continued)

(58) Field of Classification Search
CPC ......... G01N 33/6818; G01N 33/54373; G01N 33/573; G01N 2333/96455; C12Q 1/6825;
(Continued)

(56) References Cited

U.S. PATENT DOCUMENTS 6,190,918 B1     2/2001   Chu et al.
8,968,545 B2     3/2015   Holt
(Continued)

FOREIGN PATENT DOCUMENTS

CN          104220874 A      12/2014
CN          104335044 A      2/2015
(Continued)

OTHER PUBLICATIONS

Stefan Howorka, "Building membrane nanopores" Nature Nanotechnology, vol. 12, pp. 619-630 (Year: 2017).*
(Continued)

*Primary Examiner* — Shafiqul Haq
*Assistant Examiner* — Nam P Nguyen
(74) *Attorney, Agent, or Firm* — Fox Rothschild LLP

(57)                    ABSTRACT

The disclosure provides a nanopore system assembled with non-membrane proteins for detecting analytes. Also disclosed are the methods, kits, and detection devices employing the disclosed nanopore system. The nanopore system has a wide variety of applications, including single molecule detection, DNA/RNA/peptide sequencing, sensing of chemicals, biological reagents, and polymers, and disease diagnosis.

19 Claims, 10 Drawing Sheets

Specification includes a Sequence Listing.

A. Layers relevant for membrane anchoring of non membrane proteins

Cis-hydrophilic layer

Membrane anchoring layer

Trans-hydrophilic layer

Non-membrane protein pore

B. Layers relevant for conjugation of probes on non-membrane proteins

Cis- functional conjugation site

Trans- functional conjugation site

Non-membrane protein pore

(51) Int. Cl.
| | |
|---|---|
| *B01J 20/28* | (2006.01) |
| *C12Q 1/6825* | (2018.01) |
| *G01N 33/543* | (2006.01) |
| *G01N 33/573* | (2006.01) |
| *G01N 33/68* | (2006.01) |
| *B82Y 15/00* | (2011.01) |
| *C12Q 1/6869* | (2018.01) |

(52) U.S. Cl.
CPC ............ *G01N 33/573* (2013.01); *B82Y 15/00* (2013.01); *C12Q 1/6869* (2013.01); *G01N 2333/96455* (2013.01)

(58) Field of Classification Search
CPC .... C12Q 1/6869; B82Y 15/00; B01J 20/3204; B01J 20/3206; B01J 20/3274; B01J 20/2808
See application file for complete search history.

(56) References Cited

U.S. PATENT DOCUMENTS

| | | | |
|---|---|---|---|
| 2003/0232340 A1 | 12/2003 | Anderson | |
| 2005/0266416 A1 | 12/2005 | Guo | |
| 2015/0177237 A1 | 6/2015 | Turner et al. | |
| 2015/0267253 A1 | 9/2015 | Guo | |
| 2017/0058337 A1 | 3/2017 | Clarke et al. | |
| 2017/0199149 A1 | 7/2017 | Gundlach et al. | |
| 2017/0343530 A1 | 11/2017 | Guo et al. | |

FOREIGN PATENT DOCUMENTS

| | | | |
|---|---|---|---|
| CN | 106133513 A | 11/2016 | |
| JP | 2005530142 A | 10/2005 | |
| WO | 2010062697 A2 | 6/2010 | |
| WO | 2014153625 A1 | 10/2014 | |
| WO | 2016187159 A2 | 11/2016 | |
| WO | 2017049101 A2 | 3/2017 | |
| WO | 2017167811 A1 | 10/2017 | |
| WO | 2017184866 A1 | 10/2017 | |

OTHER PUBLICATIONS

Protein NCBI (https://www.ncbi.nlm.nih.gov/protein/5FB4_A?report=genbank&log$=protalign&blast_rank=1&RID=RMR7GNEW013, print retrieved on Dec. 13, 2023) (Year: 2023).*
Nucleotide NCBI (https://www.ncbi.nlm.nih.gov/nucleotide/JQ478411.1?report=genbank&log$=nuclalign&blast_rank=1&RID=RKXGPNRC016, print retrieved on Dec. 13, 2023) (Year: 2023).*
Zakeri et al. ("Peptide tag forming a rapid covalent bond to a protein, through engineering a bacterial adhesin", PNAS, vol. 109 (No. 12), pp. E690-E697, published Feb. 24, 2012) (Year: 2012).*
Morton et al. ("Tailored polymeric membranes for *Mycobacterium smegmatis* porin A (MspA) based biosensors", J. Mater. Chem. B, vol. 3, pp. 5080-5086, published May 5, 2015) (Year: 2015).*
Wang, "Three-step channel conformational changes common to DNA packaging motors of bacterial viruses T3, T4, SPP1, and Phi29", Virology, Elsevier, Amsterdam, NL, vol. 500, May 12, 2016, pp. 285-291.
Extended European Search Report for European Application No. 19750540.7, filing date Feb. 11, 2019, mailed Apr. 28, 2022.
Haque et al., Real-Time Sensing and Discriminaton of Single Chemicals using the Channel of Phi29 DNA Packaging Nanomotor, ACS Nano, Mar. 29, 2012, vol. 6, No. 4, pp. 3251-3261.
Wang et al., Engineered Nanopore of Phi29 DNA-Packaging Motor for Real-Time Detection of Single Colon Cancer Specific Antibody in Serum, ACS Nano, Nov. 26, 2013, vol. 7, No. 11, pp. 9814-9822.
Wang, Shaoying et al., Engineering of protein nanopores for sequencing, chemical or protein sensing and disease diagnosis, Current Opinion in Biotechnology, vol. 51, Dec. 10, 2017 (Dec. 10, 2017).

Wang, Shaoying, Development of new biological nanopores and their application for biosensing and disease detection, Jan. 1, 2016 (Jan. 1, 2016).
Xu, Jingwei, et al., The bacteriophage [phi]29 tail possesses a pore-forming loop for cell membrane penetration, Nature, vol. 534, No. 7608, Jun. 20, 2016 (Jun. 20, 2016), pp. 544-547.
Geng, Jia, et al., Channel Size Conversion of Phi29 DNA-Packaging Nanomotor for Discrimination of Single- and Double-Stranded Nucleic Acids, ACS NANO, vol. 7, No. 4, Mar. 15, 2013 (Mar. 15, 2013), pp. 3315-3323.
Cingolani, Gino et al., Preliminary crystallographic analysis of the bacteriophage P22 portal protein, Journal of Structural Biology, vol. 139, No. 1, Jul. 1, 2002 (Jul. 1, 2002), pp. 46-54.
Batzer et al., (1991) Enhanced evolutionary PCR using oligonucle-otides with inosine at the 3'-terminus Nucleic Acid Res. 19: 5081.
Berg et al (Biochemistry, 5th edition, New York: W H Freeman; 2002), downloaded on Apr. 18, 2014 from URL: <http://www.ncbi.nlm.nih.gov/books/NBK22361/.
Cressiot B. et al; (2017) Porphyrin-Assisted Docking of a Thermophage Portal Protein into Lipid Bilayers: Nanopore Engineering and Characterization; ACS Nano, ;11(12):11931-11945. doi: 10.1021/acsnano.7b06980.
Garalde et al., (2011) Distinct Complexes of DNA Polymerase I (Klenow Fragment) for Base and Sugar Discrimination during Nucleotide Substrate Selection J. Biol. Chem. 286: 14480-14492.
Guasch et al, Detailed Architecture of a DNA Translocating Machine: The High-resolution Structure of the Bacteriophage phi29 Connec-tor Particle, J. Mol. Biol. (2002) 315, 663-676.
Guo et al, Construction and 3-D Computer Modeling of Connector Arrays withT etragonal to Decagonal Transition Induced by pRNA of phi29 DNA-Packaging Motor, Journal of Nanoscience and Nanotechnology, vol. 5, 856-863, 2005.
Howorka et al (2001) Kinetics of duplex formation for individual DNA strands within a single protein nanopore; PNAS 98: 12996-13301.
Howorka et al. (2001); Sequence-specific detection of individual DNA strands using engineered nanopores; Nature Biotechnology 19: 636-639.
Howorka et al., (2002) Probing distance and electrical potential within a protein pore with tethered DNA; Biophysical Journal 83: 3202-3210.
Hurt et al., (2009) Specific Nucleotide Binding and Rebinding to Individual DNA Polymerase Complexes Captured on a Nanopore; JACS 131: 3772-3778.
International Search Report issued for PCT/US2019/017329, mailed Jun. 28, 2019.
Kim et al., (2012) Detecting single-abasic residues within a DNA strand immobilized in a biological nanopore using an integrated CMOS sensor Sens. Actuators B Chem. 177: 1075-1082.
Ohtsuka et al., (1985) An alternative approach to deoxyoligonucleotides as hybridization probes by insertion of deoxyinosine at ambiguous codon positions J. Biol. Chem. 260: 2605-8.
Olsen et al, (2013) Electronic Measurements of Single-Molecule Processing by DNA Polymerase I (Klenow Fragment) JACS 135: 7855-7860.
Rakhmatullina et al., (2008) Solid-Supported Block Copolymer Membranes through Interfacial Adsorption of Charged Block Copo-lymer Vesicles; Langmuir: the ACS Journal of Surfaces and Col-loids 24:6254-6261.
Rossolini et al., (1994) Use of deoxyinosine-containing primers vs degenerate primers for polymerase chain reaction based on ambigu-ous sequence information; Mol. Cell. Probes 8: 91-8, 1994.
Ying Cai, et al., The Effect of N- or C-terminal Alterations of the Connector of Bacteriophage phi9 DNA Packaging Motor on Procapsid Assembly, pRNA Binding, and DNA Packaging, Nanomedicine: Nanotechnology, Biology, and Medicine 4 (2008) 8-18.
Feng Xiao, et al., Fabrication of Massive Sheets of Singe Layer Patterned Arrays Using Lipid Directed Reengineered Phi29 Motor Dodecamer, ACSNano vol. 3, No. 1, 100-107 (2009).
Henk M. Keizer, et al., Functional Ion Channels in Tethered Bilayer Membranes—Implications for Biosensors, ChemBioChem 2007, 8 1246-1250.

(56) References Cited

OTHER PUBLICATIONS

David Wendell, et al., Translocation of Double-Stranded DNA through Membrane-Adapted phi29 Motor Protein Nanopores, vol. 4, (2009).

* cited by examiner

A. Layers relevant for membrane anchoring of non membrane proteins

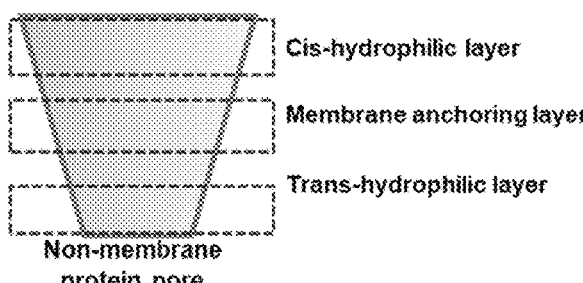

Cis-hydrophilic layer

Membrane anchoring layer

Trans-hydrophilic layer

Non-membrane protein pore

B. Layers relevant for conjugation of probes on non-membrane proteins

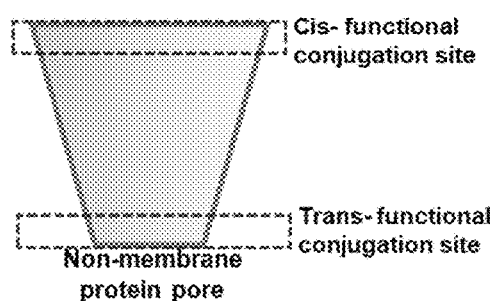

Cis- functional conjugation site

Trans- functional conjugation site

Non-membrane protein pore

FIGs. 1A, 1B

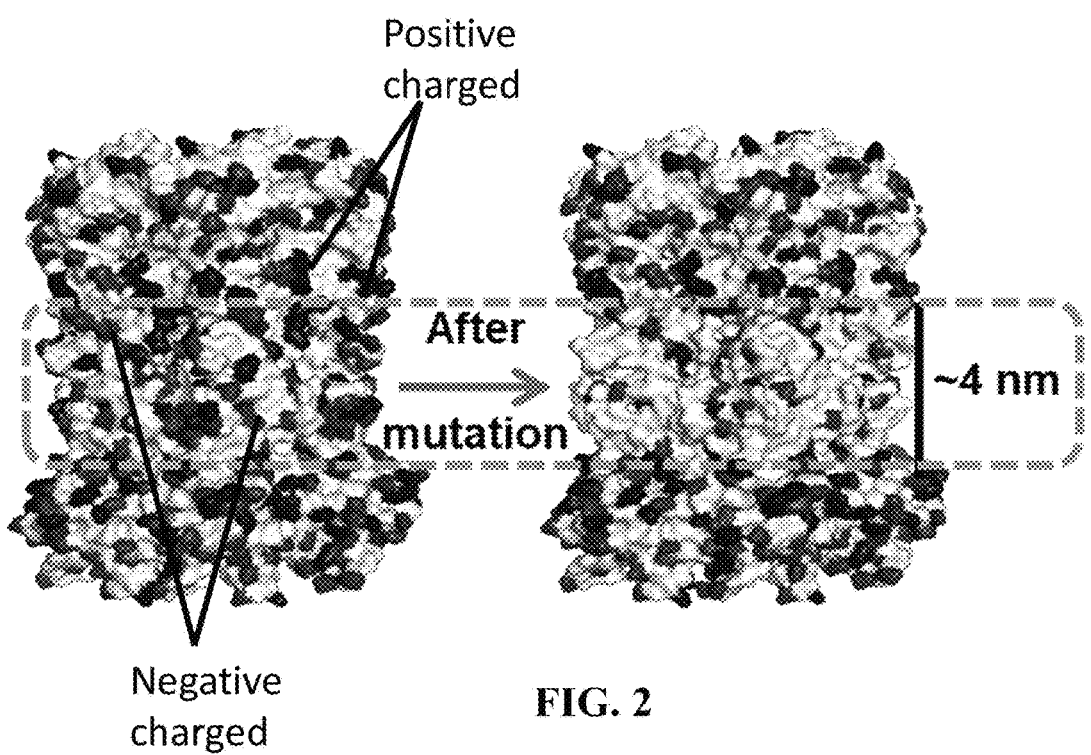

Positive charged

After mutation

~4 nm

Negative charged

FIG. 2

70 KDa

E595C

K321C

K358C

A.

B.

C283

P22BD    P22FL

85kDa
70kDa

1.  Before induction
2.  After induction
3.  Supernatant
4.  Beads after washing
5.  Elution

| | 1 | 2 | 3 | 4 |
|---|---|---|---|---|
| Methyltetrazine-protein | + | + | + | + |
| TCO-miR-21 probe | | | + | + |
| Target miR-21 | | + | | + |

FIG. 17A
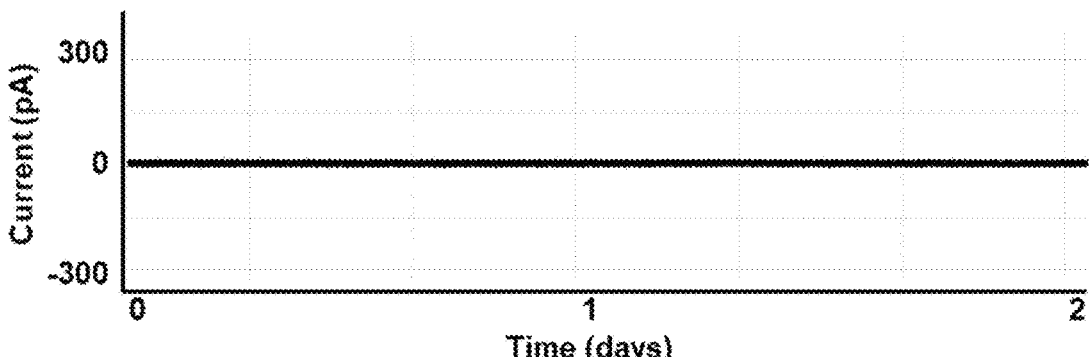
FIG. 17B
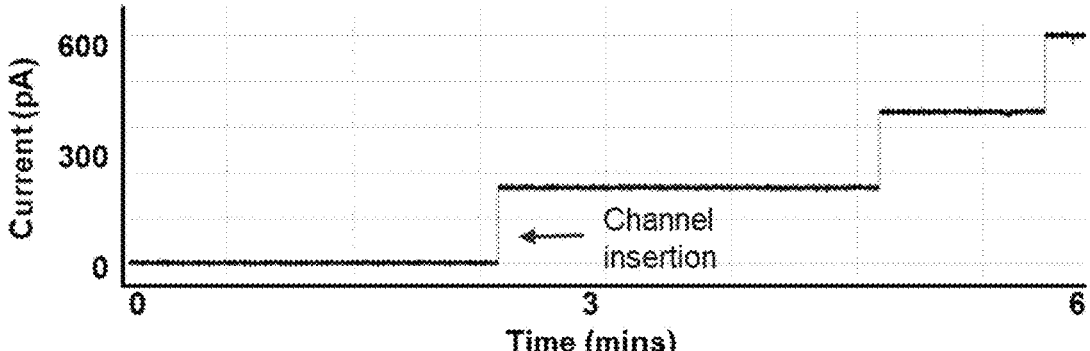
FIG. 17C
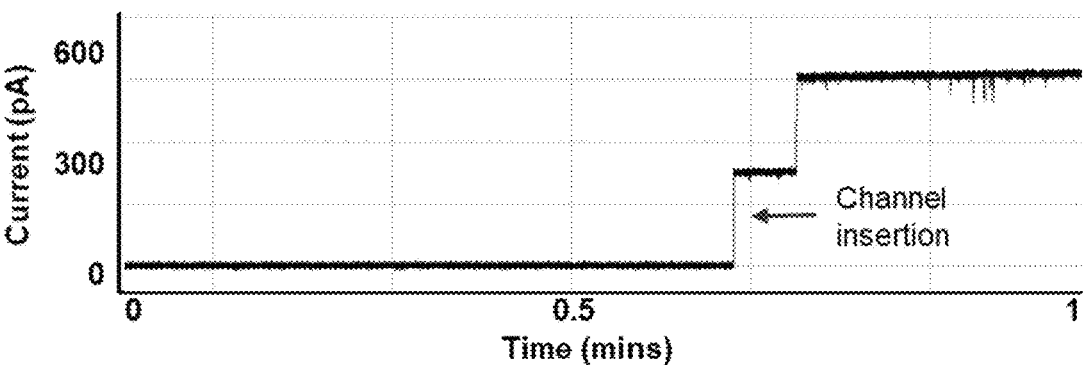
FIG. 17D

SEQUENCE LISTING

```
<160> NUMBER OF SEQ ID NOS: 93

<210> SEQ ID NO 1
<211> LENGTH: 725
<212> TYPE: PRT
<213> ORGANISM: Bacteriophage P22

<400> SEQUENCE: 1

Met Ala Asp Asn Glu Asn Arg Leu Glu Ser Ile Leu Ser Arg Phe Asp
1               5                   10                  15

Ala Asp Trp Thr Ala Ser Asp Glu Ala Arg Arg Glu Ala Lys Asn Asp
                20                  25                  30

Leu Phe Phe Ser Arg Val Ser Gln Trp Asp Asp Trp Leu Ser Gln Tyr
            35                  40                  45

Thr Thr Leu Gln Tyr Arg Gly Gln Phe Asp Val Val Arg Pro Val Val
        50                  55                  60

Arg Lys Leu Val Ser Glu Met Arg Gln Asn Pro Ile Asp Val Leu Tyr
65                  70                  75                  80

Arg Pro Lys Asp Gly Ala Arg Pro Asp Ala Ala Asp Val Leu Met Gly
                85                  90                  95

Met Tyr Arg Thr Asp Met Arg His Asn Thr Ala Lys Ile Ala Val Asn
            100                 105                 110

Ile Ala Val Arg Glu Gln Ile Glu Ala Gly Val Gly Ala Trp Arg Leu
            115                 120                 125

Val Thr Asp Tyr Glu Asp Gln Ser Pro Thr Ser Asn Asn Gln Val Ile
        130                 135                 140

Arg Arg Glu Pro Ile His Ser Ala Cys Ser His Val Ile Trp Asp Ser
145                 150                 155                 160

Asn Ser Lys Leu Met Asp Lys Ser Asp Ala Arg His Cys Thr Val Ile
                165                 170                 175

His Ser Met Ser Gln Asn Gly Trp Glu Asp Phe Ala Glu Lys Tyr Asp
            180                 185                 190

Leu Asp Ala Asp Asp Ile Pro Ser Phe Gln Asn Pro Asn Asp Trp Val
            195                 200                 205

Phe Pro Trp Leu Thr Gln Asp Thr Ile Gln Ile Ala Glu Phe Tyr Glu
        210                 215                 220

Val Val Glu Lys Lys Glu Thr Ala Phe Ile Tyr Gln Asp Pro Val Thr
225                 230                 235                 240

Gly Glu Pro Val Ser Tyr Phe Lys Arg Asp Ile Lys Asp Val Ile Asp
                245                 250                 255
```

-continued

```
Asp Leu Ala Asp Ser Gly Phe Ile Lys Ile Ala Glu Arg Gln Ile Lys
        260                 265                 270

Arg Arg Arg Val Tyr Lys Ser Ile Ile Thr Cys Thr Ala Val Leu Lys
        275                 280                 285

Asp Lys Gln Leu Ile Ala Gly Glu His Ile Pro Ile Val Pro Val Phe
        290                 295                 300

Gly Glu Trp Gly Phe Val Glu Asp Lys Glu Val Tyr Glu Gly Val Val
305                 310                 315                 320

Arg Leu Thr Lys Asp Gly Gln Arg Leu Arg Asn Met Ile Met Ser Phe
                325                 330                 335

Asn Ala Asp Ile Val Ala Arg Thr Pro Lys Lys Lys Pro Phe Phe Trp
                340                 345                 350

Pro Glu Gln Ile Ala Gly Phe Glu His Met Tyr Asp Gly Asn Asp Asp
        355                 360                 365

Tyr Pro Tyr Tyr Leu Leu Asn Arg Thr Asp Glu Asn Ser Gly Asp Leu
        370                 375                 380

Pro Thr Gln Pro Leu Ala Tyr Tyr Glu Asn Pro Glu Val Pro Gln Ala
385                 390                 395                 400

Asn Ala Tyr Met Leu Glu Ala Ala Thr Ser Ala Val Lys Glu Val Ala
                405                 410                 415

Thr Leu Gly Val Asp Thr Glu Ala Val Asn Gly Gly Gln Val Ala Phe
                420                 425                 430

Asp Thr Val Asn Gln Leu Asn Met Arg Ala Asp Leu Glu Thr Tyr Val
        435                 440                 445

Phe Gln Asp Asn Leu Ala Thr Ala Met Arg Arg Asp Gly Glu Ile Tyr
        450                 455                 460

Gln Ser Ile Val Asn Asp Ile Tyr Asp Val Pro Arg Asn Val Thr Ile
465                 470                 475                 480

Thr Leu Glu Asp Gly Ser Glu Lys Asp Val Gln Leu Met Ala Glu Val
                485                 490                 495

Val Asp Leu Ala Thr Gly Glu Lys Gln Val Leu Asn Asp Ile Arg Gly
                500                 505                 510

Arg Tyr Glu Cys Tyr Thr Asp Val Gly Pro Ser Phe Gln Ser Met Lys
        515                 520                 525

Gln Gln Asn Arg Ala Glu Ile Leu Glu Leu Leu Gly Lys Thr Pro Gln
        530                 535                 540

Gly Thr Pro Glu Tyr Gln Leu Leu Leu Leu Gln Tyr Phe Thr Leu Leu
545                 550                 555                 560

Asp Gly Lys Gly Val Glu Met Met Arg Asp Tyr Ala Asn Lys Gln Leu
                565                 570                 575

Ile Gln Met Gly Val Lys Lys Pro Glu Thr Pro Glu Glu Gln Gln Trp
                580                 585                 590

Leu Val Glu Ala Gln Gln Ala Lys Gln Gly Gln Gln Asp Pro Ala Met
        595                 600                 605

Val Gln Ala Gln Gly Val Leu Leu Gln Gly Gln Ala Glu Leu Ala Lys
        610                 615                 620

Ala Gln Asn Gln Thr Leu Ser Leu Gln Ile Asp Ala Ala Lys Val Glu
625                 630                 635                 640

Ala Gln Asn Gln Leu Asn Ala Ala Arg Ile Ala Glu Ile Phe Asn Asn
                645                 650                 655

Met Asp Leu Ser Lys Gln Ser Glu Phe Arg Glu Phe Leu Lys Thr Val
        660                 665                 670
```

-continued

```
Ala Ser Phe Gln Gln Asp Arg Ser Glu Asp Ala Arg Ala Asn Ala Glu
        675              680              685

Leu Leu Leu Lys Gly Asp Glu Gln Thr His Lys Gln Arg Met Asp Ile
        690              695              700

Ala Asn Ile Leu Gln Ser Gln Arg Gln Asn Gln Pro Ser Gly Ser Val
705              710              715              720

Ala Glu Thr Pro Gln
        725

<210> SEQ ID NO 2
<211> LENGTH: 601
<212> TYPE: PRT
<213> ORGANISM: Bacteriophage P22

<400> SEQUENCE: 2

Met Ala Asp Asn Glu Asn Arg Leu Glu Ser Ile Leu Ser Arg Phe Asp
1               5               10              15

Ala Asp Trp Thr Ala Ser Asp Glu Ala Arg Arg Glu Ala Lys Asn Asp
        20              25              30

Leu Phe Phe Ser Arg Val Ser Gln Trp Asp Asp Trp Leu Ser Gln Tyr
        35              40              45

Thr Thr Leu Gln Tyr Arg Gly Gln Phe Asp Val Val Arg Pro Val Val
        50              55              60

Arg Lys Leu Val Ser Glu Met Arg Gln Asn Pro Ile Asp Val Leu Tyr
65              70              75              80

Arg Pro Lys Asp Gly Ala Arg Pro Asp Ala Ala Asp Val Leu Met Gly
                85              90              95

Met Tyr Arg Thr Asp Met Arg His Asn Thr Ala Lys Ile Ala Val Asn
        100             105             110

Ile Ala Val Arg Glu Gln Ile Glu Ala Gly Val Gly Ala Trp Arg Leu
        115             120             125

Val Thr Asp Tyr Glu Asp Gln Ser Pro Thr Ser Asn Asn Gln Val Ile
        130             135             140

Arg Arg Glu Pro Ile His Ser Ala Cys Ser His Val Ile Trp Asp Ser
145             150             155             160

Asn Ser Lys Leu Met Asp Lys Ser Asp Ala Arg His Cys Thr Val Ile
        165             170             175

His Ser Met Ser Gln Asn Gly Trp Glu Asp Phe Ala Glu Lys Tyr Asp
        180             185             190

Leu Asp Ala Asp Asp Ile Pro Ser Phe Gln Asn Pro Asn Asp Trp Val
        195             200             205

Phe Pro Trp Leu Thr Gln Asp Thr Ile Gln Ile Ala Glu Phe Tyr Glu
        210             215             220

Val Val Glu Lys Lys Glu Thr Ala Phe Ile Tyr Gln Asp Pro Val Thr
225             230             235             240

Gly Glu Pro Val Ser Tyr Phe Lys Arg Asp Ile Lys Asp Val Ile Asp
                245             250             255

Asp Leu Ala Asp Ser Gly Phe Ile Lys Ile Ala Glu Arg Gln Ile Lys
        260             265             270

Arg Arg Arg Val Tyr Lys Ser Ile Ile Thr Cys Thr Ala Val Leu Lys
        275             280             285

Asp Lys Gln Leu Ile Ala Gly Glu His Ile Pro Ile Val Pro Val Phe
        290             295             300

Gly Glu Trp Gly Phe Val Glu Asp Lys Glu Val Tyr Glu Gly Val Val
305             310             315             320
```

-continued

```
Arg Leu Thr Lys Asp Gly Gln Arg Leu Arg Asn Met Ile Met Ser Phe
            325             330             335

Asn Ala Asp Ile Val Ala Arg Thr Pro Lys Lys Lys Pro Phe Phe Trp
            340             345             350

Pro Glu Gln Ile Ala Gly Phe Glu His Met Tyr Asp Gly Asn Asp Asp
            355             360             365

Tyr Pro Tyr Tyr Leu Leu Asn Arg Thr Asp Glu Asn Ser Gly Asp Leu
    370             375             380

Pro Thr Gln Pro Leu Ala Tyr Tyr Glu Asn Pro Glu Val Pro Gln Ala
385             390             395             400

Asn Ala Tyr Met Leu Glu Ala Ala Thr Ser Ala Val Lys Glu Val Ala
            405             410             415

Thr Leu Gly Val Asp Thr Glu Ala Val Asn Gly Gly Gln Val Ala Phe
            420             425             430

Asp Thr Val Asn Gln Leu Asn Met Arg Ala Asp Leu Glu Thr Tyr Val
            435             440             445

Phe Gln Asp Asn Leu Ala Thr Ala Met Arg Arg Asp Gly Glu Ile Tyr
    450             455             460

Gln Ser Ile Val Asn Asp Ile Tyr Asp Val Pro Arg Asn Val Thr Ile
465             470             475             480

Thr Leu Glu Asp Gly Ser Glu Lys Asp Val Gln Leu Met Ala Glu Val
            485             490             495

Val Asp Leu Ala Thr Gly Glu Lys Gln Val Leu Asn Asp Ile Arg Gly
            500             505             510

Arg Tyr Glu Cys Tyr Thr Asp Val Gly Pro Ser Phe Gln Ser Met Lys
            515             520             525

Gln Gln Asn Arg Ala Glu Ile Leu Glu Leu Leu Gly Lys Thr Pro Gln
    530             535             540

Gly Thr Pro Glu Tyr Gln Leu Leu Leu Leu Gln Tyr Phe Thr Leu Leu
545             550             555             560

Asp Gly Lys Gly Val Glu Met Met Arg Asp Tyr Ala Asn Lys Gln Leu
            565             570             575

Ile Gln Met Gly Val Lys Lys Pro Glu Thr Pro Glu Glu Gln Gln Trp
            580             585             590

Leu Val Glu Ala Gln Gln Ala Lys Gln
            595             600

<210> SEQ ID NO 3
<211> LENGTH: 599
<212> TYPE: PRT
<213> ORGANISM: Bacteriophage phi-29

<400> SEQUENCE: 3

Met Ala Tyr Val Pro Leu Ser Gly Thr Asn Val Arg Ile Leu Ala Asp
1               5               10              15

Val Pro Phe Ser Asn Asp Tyr Lys Asn Thr Arg Trp Phe Thr Ser Ser
            20              25              30

Ser Asn Gln Tyr Asn Trp Phe Asn Ser Lys Ser Arg Val Tyr Glu Met
        35              40              45

Ser Lys Val Thr Phe Met Gly Phe Arg Glu Asn Lys Pro Tyr Val Ser
    50              55              60

Val Ser Leu Pro Ile Asp Lys Leu Tyr Ser Ala Ser Tyr Ile Met Phe
65              70              75              80

Gln Asn Ala Asp Tyr Gly Asn Lys Trp Phe Tyr Ala Phe Val Thr Glu
```

-continued

```
                    85              90              95
Leu Glu Phe Lys Asn Ser Ala Val Thr Tyr Val His Phe Glu Ile Asp
            100             105             110

Val Leu Gln Thr Trp Met Phe Asp Ile Lys Phe Gln Glu Ser Phe Ile
            115             120             125

Val Arg Glu His Val Lys Leu Trp Asn Asp Asp Gly Thr Pro Thr Ile
        130             135             140

Asn Thr Ile Asp Glu Gly Leu Ser Tyr Gly Ser Glu Tyr Asp Ile Val
145             150             155             160

Ser Val Glu Asn His Lys Pro Tyr Asp Asp Met Met Phe Leu Val Ile
                165             170             175

Ile Ser Lys Ser Ile Met His Gly Thr Pro Gly Glu Glu Ser Arg
            180             185             190

Leu Asn Asp Ile Asn Ala Ser Leu Asn Gly Met Pro Gln Pro Leu Cys
            195             200             205

Tyr Tyr Ile His Pro Phe Tyr Lys Asp Gly Lys Val Pro Lys Thr Tyr
        210             215             220

Ile Gly Asp Asn Asn Ala Asn Leu Ser Pro Ile Val Asn Met Leu Thr
225             230             235             240

Asn Ile Phe Ser Gln Lys Ser Ala Val Asn Asp Ile Val Asn Met Tyr
                245             250             255

Val Thr Asp Tyr Ile Gly Leu Lys Leu Asp Tyr Lys Asn Gly Asp Lys
            260             265             270

Glu Leu Lys Leu Asp Lys Asp Met Phe Glu Gln Ala Gly Ile Ala Asp
            275             280             285

Asp Lys His Gly Asn Val Asp Thr Ile Phe Val Lys Lys Ile Pro Asp
        290             295             300

Tyr Glu Ala Leu Glu Ile Asp Thr Gly Asp Lys Trp Gly Gly Phe Thr
305             310             315             320

Lys Asp Gln Glu Ser Lys Leu Met Met Tyr Pro Tyr Cys Val Thr Glu
                325             330             335

Ile Thr Asp Phe Lys Gly Asn His Met Asn Leu Lys Thr Glu Tyr Ile
            340             345             350

Asn Asn Ser Lys Leu Lys Ile Gln Val Arg Gly Ser Leu Gly Val Ser
            355             360             365

Asn Lys Val Ala Tyr Ser Val Gln Asp Tyr Asn Ala Asp Ser Ala Leu
        370             375             380

Ser Gly Gly Asn Arg Leu Thr Ala Ser Leu Asp Ser Ser Leu Ile Asn
385             390             395             400

Asn Asn Pro Asn Asp Ile Ala Ile Leu Asn Asp Tyr Leu Ser Ala Tyr
                405             410             415

Leu Gln Gly Asn Lys Asn Ser Leu Glu Asn Gln Lys Ser Ser Ile Leu
            420             425             430

Phe Asn Gly Ile Met Gly Met Ile Gly Gly Gly Ile Ser Ala Gly Ala
            435             440             445

Ser Ala Ala Gly Gly Ser Ala Leu Gly Met Ala Ser Ser Val Thr Gly
        450             455             460

Met Thr Ser Thr Ala Gly Asn Ala Val Leu Gln Met Gln Ala Met Gln
465             470             475             480

Ala Lys Gln Ala Asp Ile Ala Asn Ile Pro Pro Gln Leu Thr Lys Met
                485             490             495

Gly Gly Asn Thr Ala Phe Asp Tyr Gly Asn Gly Tyr Arg Gly Val Tyr
            500             505             510
```

-continued

```
Val Ile Lys Lys Gln Leu Lys Ala Glu Tyr Arg Arg Ser Leu Ser Ser
    515                 520                 525

Phe Phe His Lys Tyr Gly Tyr Lys Ile Asn Arg Val Lys Lys Pro Asn
    530                 535                 540

Leu Arg Thr Arg Lys Ala Phe Asn Tyr Val Gln Thr Lys Asp Cys Phe
545                 550                 555                 560

Ile Ser Gly Asp Ile Asn Asn Asn Asp Leu Gln Glu Ile Arg Thr Ile
                565                 570                 575

Phe Asp Asn Gly Ile Thr Leu Trp His Thr Asp Asn Ile Gly Asn Tyr
                580                 585                 590

Ser Val Glu Asn Glu Leu Arg
        595

<210> SEQ ID NO 4
<211> LENGTH: 524
<212> TYPE: PRT
<213> ORGANISM: Bacteriophage phi-29

<400> SEQUENCE: 4

Met Ala Tyr Val Pro Leu Ser Gly Thr Asn Val Arg Ile Leu Ala Asp
1               5                   10                  15

Val Pro Phe Ser Asn Asp Tyr Lys Asn Thr Arg Trp Phe Thr Ser Ser
                20                  25                  30

Ser Asn Gln Tyr Asn Trp Phe Asn Ser Lys Ser Arg Val Tyr Glu Met
        35                  40                  45

Ser Lys Val Thr Phe Met Gly Phe Arg Glu Asn Lys Pro Tyr Val Ser
        50                  55                  60

Val Ser Leu Pro Ile Asp Lys Leu Tyr Ser Ala Ser Tyr Ile Met Phe
65                  70                  75                  80

Gln Asn Ala Asp Tyr Gly Asn Lys Trp Phe Tyr Ala Phe Val Thr Glu
                85                  90                  95

Leu Glu Phe Lys Asn Ser Ala Val Thr Tyr Val His Phe Glu Ile Asp
                100                 105                 110

Val Leu Gln Thr Trp Met Phe Asp Ile Lys Phe Gln Glu Ser Phe Ile
        115                 120                 125

Val Arg Glu His Val Lys Leu Trp Asn Asp Asp Gly Thr Pro Thr Ile
    130                 135                 140

Asn Thr Ile Asp Glu Gly Leu Ser Tyr Gly Ser Glu Tyr Asp Ile Val
145                 150                 155                 160

Ser Val Glu Asn His Lys Pro Tyr Asp Asp Met Met Phe Leu Val Ile
                165                 170                 175

Ile Ser Lys Ser Ile Met His Gly Thr Pro Gly Glu Glu Glu Ser Arg
                180                 185                 190

Leu Asn Asp Ile Asn Ala Ser Leu Asn Gly Met Pro Gln Pro Leu Cys
        195                 200                 205

Tyr Tyr Ile His Pro Phe Tyr Lys Asp Gly Lys Val Pro Lys Thr Tyr
    210                 215                 220

Ile Gly Asp Asn Asn Ala Asn Leu Ser Pro Ile Val Asn Met Leu Thr
225                 230                 235                 240

Asn Ile Phe Ser Gln Lys Ser Ala Val Asn Asp Ile Val Asn Met Tyr
                245                 250                 255

Val Thr Asp Tyr Ile Gly Leu Lys Leu Asp Tyr Lys Asn Gly Asp Lys
                260                 265                 270

Glu Leu Lys Leu Asp Lys Asp Met Phe Glu Gln Ala Gly Ile Ala Asp
```

```
                275                 280                 285

Asp Lys His Gly Asn Val Asp Thr Ile Phe Val Lys Lys Ile Pro Asp
    290                 295                 300

Tyr Glu Ala Leu Glu Ile Asp Thr Gly Asp Lys Trp Gly Gly Phe Thr
305                 310                 315                 320

Lys Asp Gln Glu Ser Lys Leu Met Met Tyr Pro Tyr Cys Val Thr Glu
                325                 330                 335

Ile Thr Asp Phe Lys Gly Asn His Met Asn Leu Lys Thr Glu Tyr Ile
                340                 345                 350

Asn Asn Ser Lys Leu Lys Ile Gln Val Arg Gly Ser Leu Gly Val Ser
                355                 360                 365

Asn Lys Val Ala Tyr Ser Val Gln Asp Tyr Asn Ala Asp Ser Ala Leu
    370                 375                 380

Ser Gly Gly Asn Arg Leu Thr Ala Ser Leu Asp Ser Ser Leu Ile Asn
385                 390                 395                 400

Asn Asn Pro Asn Asp Ile Ala Ile Leu Asn Asp Tyr Leu Ser Ala Tyr
                405                 410                 415

Gln Leu Thr Lys Met Gly Gly Asn Thr Ala Phe Asp Tyr Gly Asn Gly
                420                 425                 430

Tyr Arg Gly Val Tyr Val Ile Lys Lys Gln Leu Lys Ala Glu Tyr Arg
                435                 440                 445

Arg Ser Leu Ser Ser Phe Phe His Lys Tyr Gly Tyr Lys Ile Asn Arg
    450                 455                 460

Val Lys Lys Pro Asn Leu Arg Thr Arg Lys Ala Phe Asn Tyr Val Gln
465                 470                 475                 480

Thr Lys Asp Cys Phe Ile Ser Gly Asp Ile Asn Asn Asn Asp Leu Gln
                485                 490                 495

Glu Ile Arg Thr Ile Phe Asp Asn Gly Ile Thr Leu Trp His Thr Asp
                500                 505                 510

Asn Ile Gly Asn Tyr Ser Val Glu Asn Glu Leu Arg
    515                 520
```

<210> SEQ ID NO 5
<211> LENGTH: 524
<212> TYPE: PRT
<213> ORGANISM: Bacteriophage phi-29

<400> SEQUENCE: 5

```
Met Ala Tyr Val Pro Leu Ser Gly Thr Asn Val Arg Ile Leu Ala Asp
1               5                   10                  15

Val Pro Phe Ser Asn Asp Tyr Lys Asn Thr Arg Trp Phe Thr Ser Ser
                20                  25                  30

Ser Asn Gln Tyr Asn Trp Phe Asn Ser Lys Ser Arg Val Tyr Glu Met
            35                  40                  45

Ser Lys Val Thr Phe Met Gly Phe Arg Glu Asn Lys Pro Tyr Val Ser
    50                  55                  60

Val Ser Leu Pro Ile Asp Lys Leu Tyr Ser Ala Ser Tyr Ile Met Phe
65                  70                  75                  80

Gln Asn Ala Asp Tyr Gly Asn Lys Trp Phe Tyr Ala Phe Val Thr Glu
                85                  90                  95

Leu Glu Phe Lys Asn Ser Ala Val Thr Tyr Val His Phe Glu Ile Asp
            100                 105                 110

Val Leu Gln Thr Trp Met Phe Asp Ile Lys Phe Gln Glu Ser Phe Ile
            115                 120                 125
```

-continued

```
Val Arg Glu His Val Lys Leu Trp Asn Asp Asp Gly Thr Pro Thr Ile
    130                 135                 140

Asn Thr Ile Asp Glu Gly Leu Ser Tyr Gly Ser Glu Tyr Asp Ile Val
145                 150                 155                 160

Ser Val Glu Asn His Lys Pro Tyr Asp Met Met Phe Leu Val Ile
                165                 170                 175

Ile Ser Lys Ser Ile Met His Gly Thr Pro Gly Glu Glu Ser Arg
                180                 185                 190

Leu Asn Asp Ile Asn Ala Ser Leu Asn Gly Met Pro Gln Pro Leu Cys
                195                 200                 205

Tyr Tyr Ile His Pro Phe Tyr Lys Asp Gly Lys Val Pro Lys Thr Tyr
    210                 215                 220

Ile Gly Asp Asn Asn Ala Asn Leu Ser Pro Ile Val Asn Met Leu Thr
225                 230                 235                 240

Asn Ile Phe Ser Gln Lys Ser Ala Val Asn Asp Ile Val Asn Met Tyr
                245                 250                 255

Val Thr Asp Tyr Ile Gly Leu Lys Leu Asp Tyr Lys Asn Gly Asp Lys
                260                 265                 270

Glu Leu Lys Leu Asp Lys Asp Met Phe Glu Gln Ala Gly Ile Ala Asp
                275                 280                 285

Asp Lys His Gly Asn Val Asp Thr Ile Phe Val Lys Lys Ile Pro Asp
    290                 295                 300

Tyr Glu Ala Leu Glu Ile Asp Thr Gly Asp Lys Trp Gly Gly Phe Thr
305                 310                 315                 320

Lys Asp Gln Glu Ser Lys Leu Met Met Tyr Pro Tyr Cys Val Thr Glu
                325                 330                 335

Ile Thr Asp Phe Lys Gly Asn His Met Asn Leu Lys Thr Glu Tyr Ile
                340                 345                 350

Asn Asn Ser Lys Leu Cys Ile Gln Val Arg Gly Ser Leu Gly Val Ser
                355                 360                 365

Asn Lys Val Ala Tyr Ser Val Gln Asp Tyr Asn Ala Asp Ser Ala Leu
    370                 375                 380

Ser Gly Gly Asn Arg Leu Thr Ala Ser Leu Asp Ser Ser Leu Ile Asn
385                 390                 395                 400

Asn Asn Pro Asn Asp Ile Ala Ile Leu Asn Asp Tyr Leu Ser Ala Tyr
                405                 410                 415

Gln Leu Thr Lys Met Gly Gly Asn Thr Ala Phe Asp Tyr Gly Asn Gly
                420                 425                 430

Tyr Arg Gly Val Tyr Val Ile Lys Lys Gln Leu Lys Ala Glu Tyr Arg
    435                 440                 445

Arg Ser Leu Ser Ser Phe Phe His Lys Tyr Gly Tyr Lys Ile Asn Arg
    450                 455                 460

Val Lys Lys Pro Asn Leu Arg Thr Arg Lys Ala Phe Asn Tyr Val Gln
465                 470                 475                 480

Thr Lys Asp Cys Phe Ile Ser Gly Asp Ile Asn Asn Asn Asp Leu Gln
                485                 490                 495

Glu Ile Arg Thr Ile Phe Asp Asn Gly Ile Thr Leu Trp His Thr Asp
                500                 505                 510

Asn Ile Gly Asn Tyr Ser Val Glu Asn Glu Leu Arg
    515                 520
```

<210> SEQ ID NO 6
<211> LENGTH: 524
<212> TYPE: PRT

-continued

```
<213> ORGANISM: Bacteriophage phi-29

<400> SEQUENCE: 6

Met Ala Tyr Val Pro Leu Ser Gly Thr Asn Val Arg Ile Leu Ala Asp
1               5                   10                  15

Val Pro Phe Ser Asn Asp Tyr Lys Asn Thr Arg Trp Phe Thr Ser Ser
                20                  25                  30

Ser Asn Gln Tyr Asn Trp Phe Asn Ser Lys Ser Arg Val Tyr Glu Met
            35                  40                  45

Ser Lys Val Thr Phe Met Gly Phe Arg Glu Asn Lys Pro Tyr Val Ser
        50                  55                  60

Val Ser Leu Pro Ile Asp Lys Leu Tyr Ser Ala Ser Tyr Ile Met Phe
65                  70                  75                  80

Gln Asn Ala Asp Tyr Gly Asn Lys Trp Phe Tyr Ala Phe Val Thr Glu
                85                  90                  95

Leu Glu Phe Lys Asn Ser Ala Val Thr Tyr Val His Phe Glu Ile Asp
                100                 105                 110

Val Leu Gln Thr Trp Met Phe Asp Ile Lys Phe Gln Glu Ser Phe Ile
            115                 120                 125

Val Arg Glu His Val Ile Leu Trp Asn Leu Leu Gly Thr Pro Thr Ile
        130                 135                 140

Asn Thr Ile Asp Glu Gly Leu Ser Tyr Gly Ser Glu Tyr Asp Ile Val
145                 150                 155                 160

Ser Val Glu Asn His Lys Pro Tyr Asp Asp Met Met Phe Leu Val Ile
                165                 170                 175

Ile Ser Lys Ser Ile Met His Gly Thr Pro Gly Glu Glu Glu Ser Arg
                180                 185                 190

Leu Asn Asp Ile Asn Ala Ser Leu Asn Gly Met Pro Gln Pro Leu Cys
                195                 200                 205

Tyr Tyr Ile His Pro Phe Tyr Lys Asp Gly Lys Val Pro Lys Thr Tyr
        210                 215                 220

Ile Gly Asp Asn Asn Ala Asn Leu Ser Pro Ile Val Asn Met Leu Thr
225                 230                 235                 240

Asn Ile Phe Ser Gln Lys Ser Ala Val Asn Asp Ile Val Asn Met Tyr
                245                 250                 255

Val Thr Asp Tyr Ile Gly Leu Lys Leu Asp Tyr Lys Asn Gly Asp Lys
                260                 265                 270

Glu Leu Lys Leu Asp Lys Asp Met Phe Glu Gln Ala Gly Ile Ala Asp
        275                 280                 285

Asp Lys His Gly Asn Val Asp Thr Ile Phe Val Lys Lys Ile Pro Asp
        290                 295                 300

Tyr Glu Ala Leu Glu Ile Asp Thr Gly Asp Lys Trp Gly Gly Phe Thr
305                 310                 315                 320

Lys Asp Gln Glu Ser Lys Leu Met Met Tyr Pro Tyr Cys Val Thr Glu
                325                 330                 335

Ile Thr Asp Phe Lys Gly Asn His Met Asn Leu Lys Thr Glu Tyr Ile
                340                 345                 350

Asn Asn Ser Lys Leu Lys Ile Gln Val Arg Gly Ser Leu Gly Val Ser
            355                 360                 365

Asn Lys Val Ala Tyr Ser Val Gln Asp Tyr Asn Ala Asp Ser Ala Leu
        370                 375                 380

Ser Gly Gly Asn Arg Leu Thr Ala Ser Leu Asp Ser Ser Leu Ile Asn
385                 390                 395                 400
```

```
Asn Asn Pro Asn Asp Ile Ala Ile Leu Asn Asp Tyr Leu Ser Ala Tyr
            405             410             415

Gln Leu Thr Lys Met Gly Gly Asn Thr Ala Phe Asp Tyr Gly Asn Gly
            420             425             430

Tyr Arg Gly Val Tyr Val Ile Lys Lys Gln Leu Lys Ala Glu Tyr Arg
            435             440             445

Arg Ser Leu Ser Ser Phe Phe His Lys Tyr Gly Tyr Lys Ile Asn Arg
    450             455             460

Val Lys Lys Pro Asn Leu Arg Thr Arg Lys Ala Phe Asn Tyr Val Gln
465             470             475             480

Thr Lys Asp Cys Phe Ile Ser Gly Asp Ile Asn Asn Asn Asp Leu Gln
                485             490             495

Glu Ile Arg Thr Ile Phe Asp Asn Gly Ile Thr Leu Trp His Thr Asp
            500             505             510

Asn Ile Gly Asn Tyr Ser Val Glu Asn Glu Leu Arg
            515             520

<210> SEQ ID NO 7
<211> LENGTH: 524
<212> TYPE: PRT
<213> ORGANISM: Bacteriophage phi-29

<400> SEQUENCE: 7

Met Ala Tyr Val Pro Leu Ser Gly Thr Asn Val Arg Ile Leu Ala Asp
1               5               10              15

Val Pro Phe Ser Asn Asp Tyr Lys Asn Thr Arg Trp Phe Thr Ser Ser
            20              25              30

Ser Asn Gln Tyr Asn Trp Phe Asn Ser Lys Ser Arg Val Tyr Glu Met
        35              40              45

Ser Lys Val Thr Phe Met Gly Phe Arg Glu Asn Lys Pro Tyr Val Ser
    50              55              60

Val Ser Leu Pro Ile Asp Lys Leu Tyr Ser Ala Ser Tyr Ile Met Phe
65              70              75              80

Gln Asn Ala Asp Tyr Gly Asn Lys Trp Phe Tyr Ala Phe Val Thr Glu
                85              90              95

Leu Glu Phe Lys Asn Ser Ala Val Thr Tyr Val His Phe Glu Ile Asp
            100             105             110

Val Leu Gln Thr Trp Met Phe Asp Ile Lys Phe Gln Glu Ser Phe Ile
            115             120             125

Val Arg Glu His Val Ile Leu Trp Asn Leu Leu Gly Thr Pro Thr Ile
    130             135             140

Asn Thr Ile Asp Glu Gly Leu Ser Tyr Gly Ser Glu Tyr Leu Ile Val
145             150             155             160

Ser Val Val Asn His Lys Pro Tyr Asp Asp Met Met Phe Leu Val Ile
                165             170             175

Ile Ser Lys Ser Ile Met His Gly Thr Pro Gly Glu Glu Glu Ser Arg
            180             185             190

Leu Asn Asp Ile Asn Ala Ser Leu Asn Gly Met Pro Gln Pro Leu Cys
            195             200             205

Tyr Tyr Ile His Pro Phe Tyr Lys Asp Gly Lys Val Pro Lys Thr Tyr
    210             215             220

Ile Gly Asp Asn Asn Ala Asn Leu Ser Pro Ile Val Asn Met Leu Thr
225             230             235             240

Asn Ile Phe Ser Gln Lys Ser Ala Val Asn Asp Ile Val Asn Met Tyr
                245             250             255
```

```
Val Thr Asp Tyr Ile Gly Leu Lys Leu Asp Tyr Lys Asn Gly Asp Lys
            260             265             270

Glu Leu Lys Leu Asp Lys Asp Met Phe Glu Gln Ala Gly Ile Ala Asp
            275             280             285

Asp Lys His Gly Asn Val Asp Thr Ile Phe Val Lys Lys Ile Pro Asp
        290             295             300

Tyr Glu Ala Leu Glu Ile Asp Thr Gly Asp Lys Trp Gly Gly Phe Thr
305             310             315             320

Lys Asp Gln Glu Ser Lys Leu Met Met Tyr Pro Tyr Cys Val Thr Glu
            325             330             335

Ile Thr Asp Phe Lys Gly Asn His Met Asn Leu Lys Thr Glu Tyr Ile
            340             345             350

Asn Asn Ser Lys Leu Lys Ile Gln Val Arg Gly Ser Leu Gly Val Ser
            355             360             365

Asn Lys Val Ala Tyr Ser Val Gln Asp Tyr Asn Ala Asp Ser Ala Leu
        370             375             380

Ser Gly Gly Asn Arg Leu Thr Ala Ser Leu Asp Ser Ser Leu Ile Asn
385             390             395             400

Asn Asn Pro Asn Asp Ile Ala Ile Leu Asn Asp Tyr Leu Ser Ala Tyr
            405             410             415

Gln Leu Thr Lys Met Gly Gly Asn Thr Ala Phe Asp Tyr Gly Asn Gly
            420             425             430

Tyr Arg Gly Val Tyr Val Ile Lys Lys Gln Leu Lys Ala Glu Tyr Arg
            435             440             445

Arg Ser Leu Ser Ser Phe Phe His Lys Tyr Gly Tyr Lys Ile Asn Arg
        450             455             460

Val Lys Lys Pro Asn Leu Arg Thr Arg Lys Ala Phe Asn Tyr Val Gln
465             470             475             480

Thr Lys Asp Cys Phe Ile Ser Gly Asp Ile Asn Asn Asn Asp Leu Gln
            485             490             495

Glu Ile Arg Thr Ile Phe Asp Asn Gly Ile Thr Leu Trp His Thr Asp
            500             505             510

Asn Ile Gly Asn Tyr Ser Val Glu Asn Glu Leu Arg
            515             520
```

```
<210> SEQ ID NO 8
<211> LENGTH: 524
<212> TYPE: PRT
<213> ORGANISM: Bacteriophage phi-29

<400> SEQUENCE: 8

Met Ala Tyr Val Pro Leu Ser Gly Thr Asn Val Arg Ile Leu Ala Asp
1               5               10              15

Val Pro Phe Ser Asn Asp Tyr Lys Asn Thr Arg Trp Phe Thr Ser Ser
            20              25              30

Ser Asn Gln Tyr Asn Trp Phe Asn Ser Lys Ser Arg Val Tyr Glu Met
        35              40              45

Ser Lys Val Thr Phe Met Gly Phe Arg Glu Asn Lys Pro Tyr Val Ser
        50              55              60

Val Ser Leu Pro Ile Asp Lys Leu Tyr Ser Ala Ser Tyr Ile Met Phe
65              70              75              80

Gln Asn Ala Asp Tyr Gly Asn Lys Trp Phe Tyr Ala Phe Val Thr Glu
            85              90              95

Leu Glu Phe Lys Asn Ser Ala Val Thr Tyr Val His Phe Glu Ile Asp
```

```
              100                 105                 110
Val Leu Gln Thr Trp Met Phe Asp Ile Lys Phe Gln Glu Ser Phe Ile
        115                 120                 125

Val Arg Glu His Val Ile Leu Trp Asn Leu Leu Gly Thr Pro Thr Ile
        130                 135                 140

Asn Thr Ile Asp Glu Gly Leu Ser Tyr Gly Ser Glu Tyr Leu Ile Val
145                 150                 155                 160

Ser Val Val Asn His Lys Pro Tyr Asp Asp Met Met Phe Leu Val Ile
                165                 170                 175

Ile Ser Lys Ser Ile Met His Gly Thr Pro Gly Glu Glu Ser Arg
                180                 185                 190

Leu Asn Asp Ile Asn Ala Ser Leu Asn Gly Met Pro Gln Pro Leu Cys
        195                 200                 205

Tyr Tyr Ile His Pro Phe Tyr Lys Asp Gly Lys Val Pro Lys Thr Tyr
        210                 215                 220

Ile Gly Asp Asn Asn Ala Asn Leu Ser Pro Ile Val Asn Met Leu Thr
225                 230                 235                 240

Asn Ile Phe Ser Gln Lys Ser Ala Val Asn Asp Ile Val Asn Met Tyr
                245                 250                 255

Val Thr Asp Tyr Ile Gly Leu Lys Leu Asp Tyr Lys Asn Gly Asp Lys
                260                 265                 270

Glu Leu Lys Leu Asp Lys Asp Met Phe Glu Gln Ala Gly Ile Ala Asp
        275                 280                 285

Asp Lys His Gly Asn Val Asp Thr Ile Phe Val Lys Lys Ile Pro Asp
        290                 295                 300

Tyr Glu Ala Leu Val Ile Val Thr Gly Asp Lys Trp Gly Gly Phe Thr
305                 310                 315                 320

Lys Asp Gln Glu Ser Lys Leu Met Met Tyr Pro Tyr Cys Val Thr Glu
                325                 330                 335

Ile Thr Asp Phe Lys Gly Asn His Met Asn Leu Lys Thr Glu Tyr Ile
                340                 345                 350

Asn Asn Ser Lys Leu Lys Ile Gln Val Arg Gly Ser Leu Gly Val Ser
        355                 360                 365

Asn Lys Val Ala Tyr Ser Val Gln Asp Tyr Asn Ala Asp Ser Ala Leu
        370                 375                 380

Ser Gly Gly Asn Arg Leu Thr Ala Ser Leu Asp Ser Ser Leu Ile Asn
385                 390                 395                 400

Asn Asn Pro Asn Asp Ile Ala Ile Leu Asn Asp Tyr Leu Ser Ala Tyr
                405                 410                 415

Gln Leu Thr Lys Met Gly Gly Asn Thr Ala Phe Asp Tyr Gly Asn Gly
                420                 425                 430

Tyr Arg Gly Val Tyr Val Ile Lys Lys Gln Leu Lys Ala Glu Tyr Arg
        435                 440                 445

Arg Ser Leu Ser Ser Phe Phe His Lys Tyr Gly Tyr Lys Ile Asn Arg
        450                 455                 460

Val Lys Lys Pro Asn Leu Arg Thr Arg Lys Ala Phe Asn Tyr Val Gln
465                 470                 475                 480

Thr Lys Asp Cys Phe Ile Ser Gly Asp Ile Asn Asn Asn Asp Leu Gln
                485                 490                 495

Glu Ile Arg Thr Ile Phe Asp Asn Gly Ile Thr Leu Trp His Thr Asp
                500                 505                 510

Asn Ile Gly Asn Tyr Ser Val Glu Asn Glu Leu Arg
        515                 520
```

```
<210> SEQ ID NO 9
<211> LENGTH: 524
<212> TYPE: PRT
<213> ORGANISM: Bacteriophage phi-29

<400> SEQUENCE: 9

Met Ala Tyr Val Pro Leu Ser Gly Thr Asn Val Arg Ile Leu Ala Asp
1               5                   10                  15

Val Pro Phe Ser Asn Asp Tyr Lys Asn Thr Arg Trp Phe Thr Ser Ser
                20                  25                  30

Ser Asn Gln Tyr Asn Trp Phe Asn Ser Lys Ser Arg Val Tyr Glu Met
            35                  40                  45

Ser Lys Val Thr Phe Met Gly Phe Arg Glu Asn Lys Pro Tyr Val Ser
        50                  55                  60

Val Ser Leu Pro Ile Asp Lys Leu Tyr Ser Ala Ser Tyr Ile Met Phe
65                  70                  75                  80

Gln Asn Ala Asp Tyr Gly Asn Lys Trp Phe Tyr Ala Phe Val Thr Glu
                85                  90                  95

Leu Glu Phe Lys Asn Ser Ala Val Thr Tyr Val His Phe Glu Ile Asp
            100                 105                 110

Val Leu Gln Thr Trp Met Phe Asp Ile Lys Phe Gln Glu Ser Phe Ile
        115                 120                 125

Val Arg Glu His Val Lys Leu Trp Asn Asp Asp Gly Thr Pro Thr Ile
        130                 135                 140

Asn Thr Ile Asp Glu Gly Leu Ser Tyr Gly Ser Glu Tyr Asp Ile Val
145                 150                 155                 160

Ser Val Glu Asn His Lys Pro Tyr Asp Asp Met Met Phe Leu Val Ile
                165                 170                 175

Ile Ser Lys Ser Ile Met His Gly Thr Pro Gly Glu Glu Glu Ser Arg
            180                 185                 190

Leu Asn Asp Ile Asn Ala Ser Leu Asn Gly Met Pro Gln Pro Leu Cys
            195                 200                 205

Tyr Tyr Ile His Pro Phe Tyr Lys Asp Gly Lys Val Pro Lys Thr Tyr
        210                 215                 220

Ile Gly Asp Asn Asn Ala Asn Leu Ser Pro Ile Val Asn Met Leu Thr
225                 230                 235                 240

Asn Ile Phe Ser Gln Lys Ser Ala Val Asn Asp Ile Val Asn Met Tyr
                245                 250                 255

Val Thr Asp Tyr Ile Gly Leu Lys Leu Asp Tyr Lys Asn Gly Asp Lys
            260                 265                 270

Glu Leu Lys Leu Asp Lys Asp Met Phe Glu Gln Ala Gly Ile Ala Asp
            275                 280                 285

Asp Lys His Gly Asn Val Asp Thr Ile Phe Val Lys Lys Ile Pro Asp
        290                 295                 300

Tyr Glu Ala Leu Glu Ile Asp Thr Gly Asp Lys Trp Gly Gly Phe Thr
305                 310                 315                 320

Lys Asp Gln Glu Ser Lys Leu Met Met Tyr Pro Tyr Cys Val Thr Glu
                325                 330                 335

Ile Thr Asp Phe Lys Gly Asn His Met Asn Leu Lys Thr Glu Tyr Ile
            340                 345                 350

Asn Asn Ser Ala Leu Ala Ile Gln Val Arg Gly Ser Leu Gly Val Ser
        355                 360                 365

Asn Lys Val Ala Tyr Ser Val Gln Asp Tyr Asn Ala Asp Ser Ala Leu
```

-continued

```
          370               375               380

Ser Gly Gly Asn Arg Leu Thr Ala Ser Leu Asp Ser Ser Leu Ile Asn
385               390               395               400

Asn Asn Pro Asn Asp Ile Ala Ile Leu Asn Asp Tyr Leu Ser Ala Tyr
              405               410               415

Gln Leu Thr Lys Met Gly Gly Asn Thr Ala Phe Asp Tyr Gly Asn Gly
              420               425               430

Tyr Arg Gly Val Tyr Val Ile Lys Lys Gln Leu Lys Ala Glu Tyr Arg
              435               440               445

Arg Ser Leu Ser Ser Phe Phe His Lys Tyr Gly Tyr Lys Ile Asn Arg
              450               455               460

Val Lys Lys Pro Asn Leu Arg Thr Arg Lys Ala Phe Asn Tyr Val Gln
465               470               475               480

Thr Lys Asp Cys Phe Ile Ser Gly Asp Ile Asn Asn Asn Asp Leu Gln
              485               490               495

Glu Ile Arg Thr Ile Phe Asp Asn Gly Ile Thr Leu Trp His Thr Asp
              500               505               510

Asn Ile Gly Asn Tyr Ser Val Glu Asn Glu Leu Arg
              515               520
```

<210> SEQ ID NO 10
<211> LENGTH: 524
<212> TYPE: PRT
<213> ORGANISM: Bacteriophage phi-29

<400> SEQUENCE: 10

```
Met Ala Tyr Val Pro Leu Ser Gly Thr Asn Val Arg Ile Leu Ala Asp
1               5                10                15

Val Pro Phe Ser Asn Asp Tyr Lys Asn Thr Arg Trp Phe Thr Ser Ser
              20                25                30

Ser Asn Gln Tyr Asn Trp Phe Asn Ser Lys Ser Arg Val Tyr Glu Met
              35                40                45

Ser Lys Val Thr Phe Met Gly Phe Arg Glu Asn Lys Pro Tyr Val Ser
    50                55                60

Val Ser Leu Pro Ile Asp Lys Leu Tyr Ser Ala Ser Tyr Ile Met Phe
65                70                75                80

Gln Asn Ala Asp Tyr Gly Asn Lys Trp Phe Tyr Ala Phe Val Thr Glu
              85                90                95

Leu Glu Phe Lys Asn Ser Ala Val Thr Tyr Val His Phe Glu Ile Asp
              100               105               110

Val Leu Gln Thr Trp Met Phe Asp Ile Lys Phe Gln Glu Ser Phe Ile
              115               120               125

Val Arg Glu His Val Lys Leu Trp Asn Asp Asp Gly Thr Pro Thr Ile
              130               135               140

Asn Thr Ile Asp Glu Gly Leu Ser Tyr Gly Ser Glu Tyr Asp Ile Val
145               150               155               160

Ser Val Glu Asn His Lys Pro Tyr Asp Asp Met Met Phe Leu Val Ile
              165               170               175

Ile Ser Lys Ser Ile Met His Gly Thr Pro Gly Glu Glu Glu Ser Arg
              180               185               190

Leu Asn Asp Ile Asn Ala Ser Leu Asn Gly Met Pro Gln Pro Leu Cys
              195               200               205

Tyr Tyr Ile His Pro Phe Tyr Lys Asp Gly Lys Val Pro Lys Thr Tyr
    210               215               220
```

-continued

```
Ile Gly Asp Asn Asn Ala Asn Leu Ser Pro Ile Val Asn Met Leu Thr
225             230             235             240

Asn Ile Phe Ser Gln Lys Ser Ala Val Asn Asp Ile Val Asn Met Tyr
            245             250             255

Val Thr Asp Tyr Ile Gly Leu Lys Leu Asp Tyr Lys Asn Gly Asp Lys
            260             265             270

Glu Leu Lys Leu Asp Lys Asp Met Phe Glu Gln Ala Gly Ile Ala Asp
            275             280             285

Asp Lys His Gly Asn Val Asp Thr Ile Phe Val Lys Lys Ile Pro Asp
            290             295             300

Tyr Glu Ala Leu Glu Ile Asp Thr Gly Asp Lys Trp Gly Gly Phe Thr
305             310             315             320

Lys Asp Gln Glu Ser Lys Leu Met Met Tyr Pro Tyr Cys Val Thr Glu
            325             330             335

Ile Thr Asp Phe Lys Gly Asn His Met Asn Leu Lys Thr Glu Tyr Ile
            340             345             350

Asn Asn Ser Ala Leu Ala Ile Gln Val Arg Gly Ser Leu Gly Val Ser
            355             360             365

Asn Lys Val Ala Tyr Ser Val Gln Ala Tyr Asn Ala Val Ser Ala Leu
            370             375             380

Ser Gly Gly Leu Arg Leu Thr Ala Ser Leu Asp Ser Ser Leu Ile Asn
385             390             395             400

Asn Asn Pro Asn Asp Ile Ala Ile Leu Asn Asp Tyr Leu Ser Ala Tyr
            405             410             415

Gln Leu Thr Lys Met Gly Gly Asn Thr Ala Phe Asp Tyr Gly Asn Gly
            420             425             430

Tyr Arg Gly Val Tyr Val Ile Lys Lys Gln Leu Lys Ala Glu Tyr Arg
            435             440             445

Arg Ser Leu Ser Ser Phe Phe His Lys Tyr Gly Tyr Lys Ile Asn Arg
            450             455             460

Val Lys Lys Pro Asn Leu Arg Thr Arg Lys Ala Phe Asn Tyr Val Gln
465             470             475             480

Thr Lys Asp Cys Phe Ile Ser Gly Asp Ile Asn Asn Asn Asp Leu Gln
            485             490             495

Glu Ile Arg Thr Ile Phe Asp Asn Gly Ile Thr Leu Trp His Thr Asp
            500             505             510

Asn Ile Gly Asn Tyr Ser Val Glu Asn Glu Leu Arg
            515             520
```

<210> SEQ ID NO 11
<211> LENGTH: 524
<212> TYPE: PRT
<213> ORGANISM: Bacteriophage phi-29

<400> SEQUENCE: 11

```
Met Ala Tyr Val Pro Leu Ser Gly Thr Asn Val Arg Ile Leu Ala Asp
1               5               10              15

Val Pro Phe Ser Asn Asp Tyr Lys Asn Thr Arg Trp Phe Thr Ser Ser
            20              25              30

Ser Asn Gln Tyr Asn Trp Phe Asn Ser Lys Ser Arg Val Tyr Glu Met
            35              40              45

Ser Lys Val Thr Phe Met Gly Phe Arg Glu Asn Lys Pro Tyr Val Ser
            50              55              60

Val Ser Leu Pro Ile Asp Lys Leu Tyr Ser Ala Ser Tyr Ile Met Phe
65              70              75              80
```

-continued

```
Gln Asn Ala Asp Tyr Gly Asn Lys Trp Phe Tyr Ala Phe Val Thr Glu
                85              90                  95

Leu Glu Phe Lys Asn Ser Ala Val Thr Tyr Val His Phe Glu Ile Asp
            100             105                 110

Val Leu Gln Thr Trp Met Phe Asp Ile Lys Phe Gln Glu Ser Phe Ile
        115             120              125

Val Arg Glu His Val Lys Leu Trp Asn Asp Asp Gly Thr Pro Thr Ile
    130             135              140

Asn Thr Ile Asp Glu Gly Leu Ser Tyr Gly Ser Glu Tyr Asp Ile Val
145             150             155                 160

Ser Val Glu Asn His Lys Pro Tyr Asp Asp Met Met Phe Leu Val Ile
                165             170                 175

Ile Ser Lys Ser Ile Met His Gly Thr Pro Gly Glu Glu Glu Ser Arg
            180             185             190

Leu Asn Asp Ile Asn Ala Ser Leu Asn Gly Met Pro Gln Pro Leu Cys
            195             200             205

Tyr Tyr Ile His Pro Phe Tyr Lys Asp Gly Lys Val Pro Lys Thr Tyr
        210             215             220

Ile Gly Asp Asn Asn Ala Asn Leu Ser Pro Ile Val Asn Met Leu Thr
225             230             235                 240

Asn Ile Phe Ser Gln Lys Ser Ala Val Asn Asp Ile Val Asn Met Tyr
            245             250             255

Val Thr Asp Tyr Ile Gly Leu Lys Leu Asp Tyr Lys Asn Gly Asp Lys
            260             265             270

Glu Leu Lys Leu Asp Lys Asp Met Phe Glu Gln Ala Gly Ile Ala Asp
            275             280             285

Asp Lys His Gly Asn Val Asp Thr Ile Phe Val Lys Lys Ile Pro Asp
        290             295             300

Tyr Glu Ala Leu Glu Ile Asp Thr Gly Asp Lys Trp Gly Gly Phe Thr
305             310             315                 320

Lys Asp Gln Glu Ser Lys Leu Met Met Tyr Pro Tyr Cys Val Thr Glu
            325             330             335

Ile Thr Asp Phe Lys Gly Asn His Met Asn Leu Lys Thr Glu Tyr Ile
            340             345             350

Asn Asn Ser Ala Leu Ala Ile Gln Val Arg Gly Ser Leu Gly Val Ser
            355             360             365

Asn Lys Val Ala Tyr Ser Val Gln Ala Tyr Asn Ala Val Ser Ala Leu
        370             375             380

Ser Gly Gly Leu Arg Leu Thr Ala Ser Leu Asp Ser Ser Leu Ile Asn
385             390             395                 400

Asn Asn Pro Asn Asp Ile Ala Ile Leu Asn Asp Tyr Leu Ser Ala Tyr
            405             410             415

Gln Leu Thr Lys Met Gly Gly Asn Thr Ala Phe Asp Tyr Gly Asn Gly
            420             425             430

Tyr Arg Gly Val Tyr Val Ile Lys Lys Gln Leu Lys Ala Glu Tyr Arg
        435             440             445

Arg Ser Leu Ser Ser Phe Phe His Lys Tyr Gly Tyr Lys Ile Asn Arg
    450             455             460

Val Lys Lys Pro Asn Leu Arg Thr Arg Lys Ala Phe Asn Tyr Val Gln
465             470             475                 480

Thr Lys Asp Cys Phe Ile Ser Gly Asp Ile Asn Asn Asn Asp Leu Gln
            485             490             495
```

```
Glu Ile Arg Thr Ile Phe Asp Asn Gly Ile Thr Leu Trp His Thr Asp
        500                 505                 510

Asn Ile Gly Asn Tyr Ser Val Glu Asn Glu Leu Ile
        515                 520

<210> SEQ ID NO 12
<211> LENGTH: 548
<212> TYPE: PRT
<213> ORGANISM: Bacteriophage phi-29

<400> SEQUENCE: 12

Met Asn His Lys His His His His His His Ser Ser Gly Glu Asn Leu
1               5                   10                  15

Tyr Phe Gln Gly His Met Gly Ser Met Ala Tyr Val Pro Leu Ser Gly
                20                  25                  30

Thr Asn Val Arg Ile Leu Ala Asp Val Pro Phe Ser Asn Asp Tyr Lys
        35                  40                  45

Asn Thr Arg Trp Phe Thr Ser Ser Ser Asn Gln Tyr Asn Trp Phe Asn
    50                  55                  60

Ser Lys Ser Arg Val Tyr Glu Met Ser Lys Val Thr Phe Met Gly Phe
65                  70                  75                  80

Arg Glu Asn Lys Pro Tyr Val Ser Val Ser Leu Pro Ile Asp Lys Leu
                85                  90                  95

Tyr Ser Ala Ser Tyr Ile Met Phe Gln Asn Ala Asp Tyr Gly Asn Lys
            100                 105                 110

Trp Phe Tyr Ala Phe Val Thr Glu Leu Glu Phe Lys Asn Ser Ala Val
        115                 120                 125

Thr Tyr Val His Phe Glu Ile Asp Val Leu Gln Thr Trp Met Phe Asp
        130                 135                 140

Ile Lys Phe Gln Glu Ser Phe Ile Val Arg Glu His Val Lys Leu Trp
145                 150                 155                 160

Asn Asp Asp Gly Thr Pro Thr Ile Asn Thr Ile Asp Glu Gly Leu Ser
                165                 170                 175

Tyr Gly Ser Glu Tyr Asp Ile Val Ser Val Glu Asn His Lys Pro Tyr
            180                 185                 190

Asp Asp Met Met Phe Leu Val Ile Ile Ser Lys Ser Ile Met His Gly
            195                 200                 205

Thr Pro Gly Glu Glu Glu Ser Arg Leu Asn Asp Ile Asn Ala Ser Leu
        210                 215                 220

Asn Gly Met Pro Gln Pro Leu Cys Tyr Tyr Ile His Pro Phe Tyr Lys
225                 230                 235                 240

Asp Gly Lys Val Pro Lys Thr Tyr Ile Gly Asp Asn Asn Ala Asn Leu
                245                 250                 255

Ser Pro Ile Val Asn Met Leu Thr Asn Ile Phe Ser Gln Lys Ser Ala
            260                 265                 270

Val Asn Asp Ile Val Asn Met Tyr Val Thr Asp Tyr Ile Gly Leu Lys
        275                 280                 285

Leu Asp Tyr Lys Asn Gly Asp Lys Glu Leu Lys Leu Asp Lys Asp Met
        290                 295                 300

Phe Glu Gln Ala Gly Ile Ala Asp Asp Lys His Gly Asn Val Asp Thr
305                 310                 315                 320

Ile Phe Val Lys Lys Ile Pro Asp Tyr Glu Ala Leu Glu Ile Asp Thr
                325                 330                 335

Gly Asp Lys Trp Gly Gly Phe Thr Lys Asp Gln Glu Ser Lys Leu Met
                340                 345                 350
```

-continued

```
Met Tyr Pro Tyr Cys Val Thr Glu Ile Thr Asp Phe Lys Gly Asn His
        355                 360                 365

Met Asn Leu Lys Thr Glu Tyr Ile Asn Asn Ser Lys Leu Lys Ile Gln
    370                 375                 380

Val Arg Gly Ser Leu Gly Val Ser Asn Lys Val Ala Tyr Ser Val Gln
385                 390                 395                 400

Asp Tyr Asn Ala Asp Ser Ala Leu Ser Gly Gly Asn Arg Leu Thr Ala
                405                 410                 415

Ser Leu Asp Ser Ser Leu Ile Asn Asn Asn Pro Asn Asp Ile Ala Ile
                420                 425                 430

Leu Asn Asp Tyr Leu Ser Ala Tyr Gln Leu Thr Lys Met Gly Gly Asn
                435                 440                 445

Thr Ala Phe Asp Tyr Gly Asn Gly Tyr Arg Gly Val Tyr Val Ile Lys
    450                 455                 460

Lys Gln Leu Lys Ala Glu Tyr Arg Arg Ser Leu Ser Ser Phe Phe His
465                 470                 475                 480

Lys Tyr Gly Tyr Lys Ile Asn Arg Val Lys Lys Pro Asn Leu Arg Thr
                485                 490                 495

Arg Lys Ala Phe Asn Tyr Val Gln Thr Lys Asp Cys Phe Ile Ser Gly
                500                 505                 510

Asp Ile Asn Asn Asn Asp Leu Gln Glu Ile Arg Thr Ile Phe Asp Asn
                515                 520                 525

Gly Ile Thr Leu Trp His Thr Asp Asn Ile Gly Asn Tyr Ser Val Glu
    530                 535                 540

Asn Glu Leu Arg
545
```

```
<210> SEQ ID NO 13
<211> LENGTH: 599
<212> TYPE: PRT
<213> ORGANISM: Bacteriophage phi-29

<400> SEQUENCE: 13
```

```
Met Ala Tyr Val Pro Leu Ser Gly Thr Asn Val Arg Ile Leu Ala Asp
1                   5                   10                  15

Val Pro Phe Ser Asn Asp Tyr Lys Asn Thr Arg Trp Phe Thr Ser Ser
                20                  25                  30

Ser Asn Gln Tyr Asn Trp Phe Asn Ser Lys Ser Arg Val Tyr Glu Met
        35                  40                  45

Ser Lys Val Thr Phe Met Gly Phe Arg Glu Asn Lys Pro Tyr Val Ser
    50                  55                  60

Val Ser Leu Pro Ile Asp Lys Leu Tyr Ser Ala Ser Tyr Ile Met Phe
65                  70                  75                  80

Gln Asn Ala Asp Tyr Gly Asn Lys Trp Phe Tyr Ala Phe Val Thr Glu
                85                  90                  95

Leu Glu Phe Lys Asn Ser Ala Val Thr Tyr Val His Phe Glu Ile Asp
            100                 105                 110

Val Leu Gln Thr Trp Met Phe Asp Ile Lys Phe Gln Glu Ser Phe Ile
            115                 120                 125

Val Arg Glu His Val Lys Leu Trp Asn Asp Asp Gly Thr Pro Thr Ile
        130                 135                 140

Asn Thr Ile Asp Glu Gly Leu Ser Tyr Gly Ser Glu Tyr Asp Ile Val
145                 150                 155                 160

Ser Val Glu Asn His Lys Pro Tyr Asp Asp Met Met Phe Leu Val Ile
```

-continued

```
                165                 170                 175
Ile Ser Lys Ser Ile Met His Gly Thr Pro Gly Glu Glu Glu Ser Arg
        180                 185                 190

Leu Asn Asp Ile Asn Ala Ser Leu Asn Gly Met Pro Gln Pro Leu Cys
        195                 200                 205

Tyr Tyr Ile His Pro Phe Tyr Lys Asp Gly Lys Val Pro Lys Thr Tyr
    210                 215                 220

Ile Gly Asp Asn Asn Ala Asn Leu Ser Pro Ile Val Asn Met Leu Thr
225                 230                 235                 240

Asn Ile Phe Ser Gln Lys Ser Ala Val Asn Asp Ile Val Asn Met Tyr
                245                 250                 255

Val Thr Asp Tyr Ile Gly Leu Lys Leu Asp Tyr Lys Asn Gly Asp Lys
                260                 265                 270

Glu Leu Lys Leu Asp Lys Asp Met Phe Glu Gln Ala Gly Ile Ala Asp
        275                 280                 285

Asp Lys His Gly Asn Val Asp Thr Ile Phe Val Lys Lys Ile Pro Asp
        290                 295                 300

Tyr Glu Ala Leu Glu Ile Asp Thr Gly Asp Lys Trp Gly Gly Phe Thr
305                 310                 315                 320

Cys Asp Gln Glu Ser Lys Leu Met Met Tyr Pro Tyr Cys Val Thr Glu
                325                 330                 335

Ile Thr Asp Phe Lys Gly Asn His Met Asn Leu Lys Thr Glu Tyr Ile
                340                 345                 350

Asn Asn Ser Lys Leu Lys Ile Gln Val Arg Gly Ser Leu Gly Val Ser
                355                 360                 365

Asn Lys Val Ala Tyr Ser Val Gln Asp Tyr Asn Ala Asp Ser Ala Leu
        370                 375                 380

Ser Gly Gly Asn Arg Leu Thr Ala Ser Leu Asp Ser Ser Leu Ile Asn
385                 390                 395                 400

Asn Asn Pro Asn Asp Ile Ala Ile Leu Asn Asp Tyr Leu Ser Ala Tyr
                405                 410                 415

Leu Gln Gly Asn Lys Asn Ser Leu Glu Asn Gln Lys Ser Ser Ile Leu
        420                 425                 430

Phe Asn Gly Ile Met Gly Met Ile Gly Gly Gly Ile Ser Ala Gly Ala
        435                 440                 445

Ser Ala Ala Gly Gly Ser Ala Leu Gly Met Ala Ser Ser Val Thr Gly
    450                 455                 460

Met Thr Ser Thr Ala Gly Asn Ala Val Leu Gln Met Gln Ala Met Gln
465                 470                 475                 480

Ala Lys Gln Ala Asp Ile Ala Asn Ile Pro Pro Gln Leu Thr Lys Met
                485                 490                 495

Gly Gly Asn Thr Ala Phe Asp Tyr Gly Asn Gly Tyr Arg Gly Val Tyr
                500                 505                 510

Val Ile Lys Lys Gln Leu Lys Ala Glu Tyr Arg Arg Ser Leu Ser Ser
        515                 520                 525

Phe Phe His Lys Tyr Gly Tyr Lys Ile Asn Arg Val Lys Lys Pro Asn
        530                 535                 540

Leu Arg Thr Arg Lys Ala Phe Asn Tyr Val Gln Thr Lys Asp Cys Phe
545                 550                 555                 560

Ile Ser Gly Asp Ile Asn Asn Asn Asp Leu Gln Glu Ile Arg Thr Ile
                565                 570                 575

Phe Asp Asn Gly Ile Thr Leu Trp His Thr Asp Asn Ile Gly Asn Tyr
        580                 585                 590
```

Ser Val Glu Asn Glu Leu Arg
        595

<210> SEQ ID NO 14
<211> LENGTH: 599
<212> TYPE: PRT
<213> ORGANISM: Bacteriophage phi-29

<400> SEQUENCE: 14

Met Ala Tyr Val Pro Leu Ser Gly Thr Asn Val Arg Ile Leu Ala Asp
1               5                   10                  15

Val Pro Phe Ser Asn Asp Tyr Lys Asn Thr Arg Trp Phe Thr Ser Ser
            20                  25                  30

Ser Asn Gln Tyr Asn Trp Phe Asn Ser Lys Ser Arg Val Tyr Glu Met
        35                  40                  45

Ser Lys Val Thr Phe Met Gly Phe Arg Glu Asn Lys Pro Tyr Val Ser
    50                  55                  60

Val Ser Leu Pro Ile Asp Lys Leu Tyr Ser Ala Ser Tyr Ile Met Phe
65                  70                  75                  80

Gln Asn Ala Asp Tyr Gly Asn Lys Trp Phe Tyr Ala Phe Val Thr Glu
                85                  90                  95

Leu Glu Phe Lys Asn Ser Ala Val Thr Tyr Val His Phe Glu Ile Asp
            100                 105                 110

Val Leu Gln Thr Trp Met Phe Asp Ile Lys Phe Gln Glu Ser Phe Ile
        115                 120                 125

Val Arg Glu His Val Lys Leu Trp Asn Asp Asp Gly Thr Pro Thr Ile
    130                 135                 140

Asn Thr Ile Asp Glu Gly Leu Ser Tyr Gly Ser Glu Tyr Asp Ile Val
145                 150                 155                 160

Ser Val Glu Asn His Lys Pro Tyr Asp Asp Met Met Phe Leu Val Ile
                165                 170                 175

Ile Ser Lys Ser Ile Met His Gly Thr Pro Gly Glu Glu Glu Ser Arg
            180                 185                 190

Leu Asn Asp Ile Asn Ala Ser Leu Asn Gly Met Pro Gln Pro Leu Cys
        195                 200                 205

Tyr Tyr Ile His Pro Phe Tyr Lys Asp Gly Lys Val Pro Lys Thr Tyr
    210                 215                 220

Ile Gly Asp Asn Asn Ala Asn Leu Ser Pro Ile Val Asn Met Leu Thr
225                 230                 235                 240

Asn Ile Phe Ser Gln Lys Ser Ala Val Asn Asp Ile Val Asn Met Tyr
                245                 250                 255

Val Thr Asp Tyr Ile Gly Leu Lys Leu Asp Tyr Lys Asn Gly Asp Lys
            260                 265                 270

Glu Leu Lys Leu Asp Lys Asp Met Phe Glu Gln Ala Gly Ile Ala Asp
        275                 280                 285

Asp Lys His Gly Asn Val Asp Thr Ile Phe Val Lys Lys Ile Pro Asp
    290                 295                 300

Tyr Glu Ala Leu Glu Ile Asp Thr Gly Asp Lys Trp Gly Gly Phe Thr
305                 310                 315                 320

Lys Asp Gln Glu Ser Lys Leu Met Met Tyr Pro Tyr Cys Val Thr Glu
                325                 330                 335

Ile Thr Asp Phe Lys Gly Asn His Met Asn Leu Lys Thr Glu Tyr Ile
            340                 345                 350

Asn Asn Ser Lys Leu Cys Ile Gln Val Arg Gly Ser Leu Gly Val Ser

-continued

```
              355                  360                  365

Asn Lys Val Ala Tyr Ser Val Gln Asp Tyr Asn Ala Asp Ser Ala Leu
    370                  375                  380

Ser Gly Gly Asn Arg Leu Thr Ala Ser Leu Asp Ser Ser Leu Ile Asn
385                  390                  395                  400

Asn Asn Pro Asn Asp Ile Ala Ile Leu Asn Asp Tyr Leu Ser Ala Tyr
                405                  410                  415

Leu Gln Gly Asn Lys Asn Ser Leu Glu Asn Gln Lys Ser Ser Ile Leu
                420                  425                  430

Phe Asn Gly Ile Met Gly Met Ile Gly Gly Gly Ile Ser Ala Gly Ala
                435                  440                  445

Ser Ala Ala Gly Gly Ser Ala Leu Gly Met Ala Ser Ser Val Thr Gly
    450                  455                  460

Met Thr Ser Thr Ala Gly Asn Ala Val Leu Gln Met Gln Ala Met Gln
465                  470                  475                  480

Ala Lys Gln Ala Asp Ile Ala Asn Ile Pro Pro Gln Leu Thr Lys Met
                485                  490                  495

Gly Gly Asn Thr Ala Phe Asp Tyr Gly Asn Gly Tyr Arg Gly Val Tyr
                500                  505                  510

Val Ile Lys Lys Gln Leu Lys Ala Glu Tyr Arg Arg Ser Leu Ser Ser
                515                  520                  525

Phe Phe His Lys Tyr Gly Tyr Lys Ile Asn Arg Val Lys Lys Pro Asn
    530                  535                  540

Leu Arg Thr Arg Lys Ala Phe Asn Tyr Val Gln Thr Lys Asp Cys Phe
545                  550                  555                  560

Ile Ser Gly Asp Ile Asn Asn Asn Asp Leu Gln Glu Ile Arg Thr Ile
                565                  570                  575

Phe Asp Asn Gly Ile Thr Leu Trp His Thr Asp Asn Ile Gly Asn Tyr
                580                  585                  590

Ser Val Glu Asn Glu Leu Arg
        595

<210> SEQ ID NO 15
<211> LENGTH: 599
<212> TYPE: PRT
<213> ORGANISM: Bacteriophage phi-29

<400> SEQUENCE: 15

Met Ala Tyr Val Pro Leu Ser Gly Thr Asn Val Arg Ile Leu Ala Asp
1                    5                   10                   15

Val Pro Phe Ser Asn Asp Tyr Lys Asn Thr Arg Trp Phe Thr Ser Ser
                20                   25                   30

Ser Asn Gln Tyr Asn Trp Phe Asn Ser Lys Ser Arg Val Tyr Glu Met
        35                   40                   45

Ser Lys Val Thr Phe Met Gly Phe Arg Glu Asn Lys Pro Tyr Val Ser
        50                   55                   60

Val Ser Leu Pro Ile Asp Lys Leu Tyr Ser Ala Ser Tyr Ile Met Phe
65                   70                   75                   80

Gln Asn Ala Asp Tyr Gly Asn Lys Trp Phe Tyr Ala Phe Val Thr Glu
                85                   90                   95

Leu Glu Phe Lys Asn Ser Ala Val Thr Tyr Val His Phe Glu Ile Asp
                100                  105                  110

Val Leu Gln Thr Trp Met Phe Asp Ile Lys Phe Gln Glu Ser Phe Ile
        115                  120                  125
```

-continued

```
Val Arg Glu His Val Lys Leu Trp Asn Asp Asp Gly Thr Pro Thr Ile
    130             135             140

Asn Thr Ile Asp Glu Gly Leu Ser Tyr Gly Ser Glu Tyr Asp Ile Val
145             150             155             160

Ser Val Glu Asn His Lys Pro Tyr Asp Met Met Phe Leu Val Ile
            165             170             175

Ile Ser Lys Ser Ile Met His Gly Thr Pro Gly Glu Glu Ser Arg
            180             185             190

Leu Asn Asp Ile Asn Ala Ser Leu Asn Gly Met Pro Gln Pro Leu Cys
            195             200             205

Tyr Tyr Ile His Pro Phe Tyr Lys Asp Gly Lys Val Pro Lys Thr Tyr
    210             215             220

Ile Gly Asp Asn Asn Ala Asn Leu Ser Pro Ile Val Asn Met Leu Thr
225             230             235             240

Asn Ile Phe Ser Gln Lys Ser Ala Val Asn Asp Ile Val Asn Met Tyr
            245             250             255

Val Thr Asp Tyr Ile Gly Leu Lys Leu Asp Tyr Lys Asn Gly Asp Lys
            260             265             270

Glu Leu Lys Leu Asp Lys Asp Met Phe Glu Gln Ala Gly Ile Ala Asp
            275             280             285

Asp Lys His Gly Asn Val Asp Thr Ile Phe Val Lys Lys Ile Pro Asp
    290             295             300

Tyr Glu Ala Leu Glu Ile Asp Thr Gly Asp Lys Trp Gly Gly Phe Thr
305             310             315             320

Lys Asp Gln Glu Ser Lys Leu Met Met Tyr Pro Tyr Cys Val Thr Glu
            325             330             335

Ile Thr Asp Phe Lys Gly Asn His Met Asn Leu Lys Thr Glu Tyr Ile
            340             345             350

Asn Asn Ser Lys Leu Lys Ile Gln Val Arg Gly Ser Leu Gly Val Ser
            355             360             365

Asn Lys Val Ala Tyr Ser Val Gln Asp Tyr Asn Ala Asp Ser Ala Leu
    370             375             380

Ser Gly Gly Asn Arg Leu Thr Ala Ser Leu Asp Ser Ser Leu Ile Asn
385             390             395             400

Asn Asn Pro Asn Asp Ile Ala Ile Leu Asn Asp Tyr Leu Ser Ala Tyr
            405             410             415

Leu Gln Gly Asn Lys Asn Ser Leu Glu Asn Gln Lys Ser Ser Ile Leu
            420             425             430

Phe Asn Gly Ile Met Gly Met Ile Gly Gly Gly Ile Ser Ala Gly Ala
            435             440             445

Ser Ala Ala Gly Gly Ser Ala Leu Gly Met Ala Ser Ser Val Thr Gly
    450             455             460

Met Thr Ser Thr Ala Gly Asn Ala Val Leu Gln Met Gln Ala Met Gln
465             470             475             480

Ala Lys Gln Ala Asp Ile Ala Asn Ile Pro Pro Gln Leu Thr Lys Met
            485             490             495

Gly Gly Asn Thr Ala Phe Asp Tyr Gly Asn Gly Tyr Arg Gly Val Tyr
            500             505             510

Val Ile Lys Lys Gln Leu Lys Ala Glu Tyr Arg Arg Ser Leu Ser Ser
            515             520             525

Phe Phe His Lys Tyr Gly Tyr Lys Ile Asn Arg Val Lys Lys Pro Asn
    530             535             540

Leu Arg Thr Arg Lys Ala Phe Asn Tyr Val Gln Thr Lys Asp Cys Phe
```

-continued

```
545              550              555              560

Ile Ser Gly Asp Ile Asn Asn Asn Asp Leu Gln Glu Ile Arg Thr Ile
             565              570              575

Phe Asp Asn Gly Ile Thr Leu Trp His Thr Asp Asn Ile Gly Asn Tyr
             580              585              590

Ser Val Cys Asn Glu Leu Arg
         595

<210> SEQ ID NO 16
<211> LENGTH: 583
<212> TYPE: PRT
<213> ORGANISM: Bacteriophage C1

<400> SEQUENCE: 16

Met Thr Leu Ser Lys Ile Lys Leu Phe Tyr Asn Thr Pro Phe Asn Asn
1               5               10              15

Met Gln Asn Thr Leu His Phe Asn Ser Asn Glu Glu Arg Asp Ala Tyr
             20              25              30

Phe Asn Ser Lys Phe Asp Val His Glu Phe Thr Ser Thr Phe Asn Tyr
         35              40              45

Arg Asn Met Lys Gly Val Leu Arg Val Thr Ile Asp Leu Val Ser Asp
     50              55              60

Arg Ser Cys Phe Glu Gln Leu Met Gly Val Asn Tyr Cys Gln Val Gln
65              70              75              80

Tyr Ile Gln Ser Asn Arg Val Glu Tyr Leu Phe Val Thr Asp Ile Gln
             85              90              95

Gln Leu Asn Asp Lys Val Cys Glu Leu Ser Leu Val Pro Asp Val Val
             100             105             110

Met Thr Tyr Thr Gln Gly Asn Val Leu Asn Thr Leu Asn Asn Val Asn
         115             120             125

Val Ile Arg Gln His Tyr Thr Gln Thr Glu Tyr Glu Gln Asn Leu Glu
     130             135             140

Gln Ile Arg Ser Asn Asn Asp Val Leu Ala Thr Ser Thr Met Arg Val
145             150             155             160

His Ala Ile Lys Ser Glu Leu Phe Thr Gln Leu Glu Tyr Ile Leu Thr
             165             170             175

Ile Gly Ala Asn Leu Arg Lys Ser Phe Gly Thr Ala Glu Lys Pro Lys
         180             185             190

Phe Pro Ser Ser Ser Gly Ser Thr His Asp Gly Ile Tyr Asn Pro Tyr
     195             200             205

Asp Met Tyr Trp Phe Asn Asp Tyr Glu Ser Leu Lys Glu Val Met Asp
     210             215             220

Tyr Leu Thr Gly Tyr Pro Trp Ile Gln Gln Ser Ile Lys Asn Val Thr
225             230             235             240

Ile Ile Pro Ser Gly Phe Ile Lys Gln Glu Ser Leu Asn Asp His Glu
             245             250             255

Pro Val Asn Gly Gly Asp Leu Ser Val Arg Lys Leu Gly Lys Gln Gly
             260             265             270

Val Ser Asn Gln Lys Asp Phe Asn Ala Ile Ser Leu Asp Tyr Gln Ser
         275             280             285

Leu Met Phe Thr Leu Gly Leu Asn Pro Ile Asn Asp Lys His Leu Leu
     290             295             300

Arg Pro Asn Ile Val Thr Ala Glu Leu Thr Asp Tyr Ala Gly Asn Arg
305             310             315             320
```

```
Leu Pro Ile Asp Leu Ser Leu Ile Glu Thr Asn Leu Glu Phe Asp Ser
            325                 330                 335

Phe Val Thr Met Gly Ala Lys Asn Glu Ile Lys Val Tyr Val Lys Asn
            340                 345                 350

Tyr Asn Ala Arg Gly Asn Asn Val Gly Gln Tyr Ile Asp Asn Ala Leu
            355                 360                 365

Thr Ile Asn Asn Phe Asp Thr Ile Gly Phe Ser Val Asp Ser Gly Glu
            370                 375                 380

Leu Gly Lys Ala Asn Ser Ala Tyr Ser Arg Glu Leu Ser Asn Ser Arg
385                 390                 395                 400

Gln Met Ser Ser Arg Ile Asn Thr Val Leu Asp Asn Asp Ala Ser Val
            405                 410                 415

Lys Asp Arg Leu Phe Asn Ala Ile Ser Leu Ser Gly Gly Leu Ser Ile
            420                 425                 430

Lys Ser Ala Leu Ser Gly Phe Asn Asn Glu Tyr Glu His Tyr Arg Asp
            435                 440                 445

Gln Lys Ala Gln Phe Lys Gln Met Asp Ala Leu Pro Asn Ala Ile Thr
            450                 455                 460

Glu Gly His Val Gly Tyr Ala Pro Leu Phe Lys Gln Asp Lys Phe Gly
465                 470                 475                 480

Val His Leu Arg Leu Gly Arg Ile Ser Gln Asp Glu Leu Asn Asn Val
            485                 490                 495

Lys Lys Tyr Tyr Asn Met Phe Gly Tyr Glu Cys Asn Asp Tyr Ser Thr
            500                 505                 510

Lys Leu Ser Asp Ile Thr Ser Met Ser Ile Cys Asn Trp Val Gln Phe
            515                 520                 525

Lys Gly Ile Trp Thr Leu Pro Asn Val Asp Thr Gly His Met Asn Met
            530                 535                 540

Leu Arg Ala Leu Phe Glu Ala Gly Val Arg Leu Trp His Lys Glu Ser
545                 550                 555                 560

Asp Met Ile Asn Asn Thr Val Val Asn Asn Val Ile Ile Lys Ser Leu
            565                 570                 575

Glu His His His His His His
            580
```

```
<210> SEQ ID NO 17
<211> LENGTH: 381
<212> TYPE: PRT
<213> ORGANISM: Neisseria meningitidis (group B)

<400> SEQUENCE: 17

Met Gln Asn Asn Ser Tyr Gly Tyr Ala Val Ser Val Arg Val Gly Gly
1                   5                   10                  15

Lys Glu His Arg His Trp Glu Arg Tyr Asp Ile Asp Ser Asp Phe Leu
            20                  25                  30

Ile Pro Ala Asp Ser Phe Asp Phe Val Ile Gly Arg Leu Gly Pro Glu
            35                  40                  45

Ala Ala Ile Pro Asp Leu Ser Gly Glu Ser Cys Glu Val Val Ile Asp
            50                  55                  60

Gly Gln Ile Val Met Thr Gly Ile Ile Gly Ser Gln Arg His Gly Lys
65                  70                  75                  80

Ser Lys Gly Ser Arg Glu Leu Ser Leu Ser Gly Arg Asp Leu Ala Gly
            85                  90                  95

Phe Leu Val Asp Cys Ser Ala Pro Gln Leu Asn Val Lys Gly Met Thr
            100                 105                 110
```

-continued

```
Val Leu Asp Ala Ala Lys Lys Leu Ala Ala Pro Trp Pro Gln Ile Lys
        115                 120                 125

Ala Val Val Leu Lys Ala Glu Asn Asn Pro Ala Leu Gly Lys Ile Asp
        130                 135                 140

Ile Glu Pro Gly Glu Thr Val Trp Gln Ala Leu Thr His Ile Ala Asn
145                 150                 155                 160

Ser Val Gly Leu His Pro Trp Leu Glu Pro Asp Gly Thr Leu Val Val
                165                 170                 175

Gly Gly Ala Asp Tyr Ser Ser Pro Pro Val Ala Thr Leu Cys Trp Ser
                180                 185                 190

Arg Thr Asp Ser Arg Cys Asn Ile Glu Arg Met Asp Ile Glu Trp Asp
        195                 200                 205

Thr Asp Asn Arg Phe Ser Glu Val Thr Phe Leu Ala Gln Ser His Gly
        210                 215                 220

Arg Ser Gly Asp Ser Ala Lys His Asp Leu Lys Trp Val Tyr Lys Asp
225                 230                 235                 240

Pro Thr Met Thr Leu His Arg Pro Lys Thr Val Val Val Ser Asp Ala
                245                 250                 255

Asp Asn Leu Ala Ala Leu Gln Lys Gln Ala Lys Lys Gln Leu Ala Asp
                260                 265                 270

Trp Arg Leu Glu Gly Phe Thr Leu Thr Ile Thr Val Gly Gly His Lys
        275                 280                 285

Thr Arg Asp Gly Val Leu Trp Gln Pro Gly Leu Arg Val His Val Ile
        290                 295                 300

Asp Asp Glu His Gly Ile Asp Ala Val Phe Phe Leu Met Gly Arg Arg
305                 310                 315                 320

Phe Met Leu Ser Arg Met Asp Gly Thr Gln Thr Glu Leu Arg Leu Lys
                325                 330                 335

Glu Asp Gly Ile Trp Thr Pro Asp Ala Tyr Pro Lys Lys Ala Glu Ala
                340                 345                 350

Ala Arg Lys Arg Lys Gly Lys Arg Lys Gly Val Ser His Lys Gly Lys
        355                 360                 365

Lys Gly Gly Lys Lys Gln Ala Glu Thr Ala Val Phe Glu
        370                 375                 380
```

```
<210> SEQ ID NO 18
<211> LENGTH: 163
<212> TYPE: PRT
<213> ORGANISM: Bacteriophage T4

<400> SEQUENCE: 18
```

```
Met Phe Val Asp Asp Val Thr Arg Ala Phe Glu Ser Gly Asp Phe Ala
1               5                   10                  15

Arg Pro Asn Leu Phe Gln Val Glu Ile Ser Tyr Leu Gly Gln Asn Phe
                20                  25                  30

Thr Phe Gln Cys Lys Ala Thr Ala Leu Pro Ala Gly Ile Val Glu Lys
        35                  40                  45

Ile Pro Val Gly Phe Met Asn Arg Lys Ile Asn Val Ala Gly Asp Arg
        50                  55                  60

Thr Phe Asp Asp Trp Thr Val Thr Val Met Asn Asp Glu Ala His Asp
65                  70                  75                  80

Ala Arg Gln Lys Phe Val Asp Trp Gln Ser Ile Ala Ala Gly Gln Gly
                85                  90                  95

Asn Glu Ile Thr Gly Gly Lys Pro Ala Glu Tyr Lys Lys Ser Ala Ile
```

-continued

```
              100                 105                 110

Val Arg Gln Tyr Ala Arg Asp Ala Lys Thr Val Thr Lys Glu Ile Glu
          115                 120                 125

Ile Lys Gly Leu Trp Pro Thr Asn Val Gly Glu Leu Gln Leu Asp Trp
      130                 135                 140

Asp Ser Asn Asn Glu Ile Gln Thr Phe Glu Val Thr Leu Ala Leu Asp
145                 150                 155                 160

Tyr Trp Glu

<210> SEQ ID NO 19
<211> LENGTH: 140
<212> TYPE: PRT
<213> ORGANISM: Bacteriophage phi-X174

<400> SEQUENCE: 19

Met Val Asp Ala Gly Phe Glu Asn Gln Lys Glu Leu Thr Lys Met Gln
1                 5                  10                 15

Leu Asp Asn Gln Lys Glu Ile Ala Glu Met Gln Asn Glu Thr Gln Lys
          20                 25                 30

Glu Ile Ala Gly Ile Gln Ser Ala Thr Ser Arg Gln Asn Thr Lys Asp
      35                 40                 45

Gln Val Tyr Ala Gln Asn Glu Met Leu Ala Tyr Gln Gln Lys Glu Ser
      50                 55                 60

Thr Ala Arg Val Ala Ser Ile Met Glu Asn Thr Asn Leu Ser Lys Gln
65                 70                 75                 80

Gln Gln Val Ser Glu Ile Met Arg Gln Met Leu Thr Gln Ala Gln Thr
                  85                 90                 95

Ala Gly Gln Tyr Phe Thr Asn Asp Gln Ile Lys Glu Met Thr Arg Lys
          100                 105                 110

Val Ser Ala Glu Val Asp Leu Val His Gln Gln Thr Gln Asn Gln Arg
          115                 120                 125

Tyr Gly Ser Ser His Ile Gly Ala Thr Ala Lys Asp
      130                 135                 140

<210> SEQ ID NO 20
<211> LENGTH: 246
<212> TYPE: PRT
<213> ORGANISM: Bacteriophage lambda

<400> SEQUENCE: 20

Met Pro Val Pro Asn Pro Thr Met Pro Val Lys Gly Ala Gly Thr Thr
1                 5                  10                 15

Leu Trp Val Tyr Lys Gly Ser Gly Asp Pro Tyr Ala Asn Pro Leu Ser
          20                 25                 30

Asp Val Asp Trp Ser Arg Leu Ala Lys Val Lys Asp Leu Thr Pro Gly
          35                 40                 45

Glu Leu Thr Ala Glu Ser Tyr Asp Asp Ser Tyr Leu Asp Asp Glu Asp
      50                 55                 60

Ala Asp Trp Thr Ala Thr Gly Gln Gly Gln Lys Ser Ala Gly Asp Thr
65                 70                 75                 80

Ser Phe Thr Leu Ala Trp Met Pro Gly Glu Gln Gly Gln Gln Ala Leu
                  85                 90                 95

Leu Ala Trp Phe Asn Glu Gly Asp Thr Arg Ala Tyr Lys Ile Arg Phe
          100                 105                 110

Pro Asn Gly Thr Val Asp Val Phe Arg Gly Trp Val Ser Ser Ile Gly
          115                 120                 125
```

```
Lys Ala Val Thr Ala Lys Glu Val Ile Thr Arg Thr Val Lys Val Thr
    130                 135                 140

Asn Val Gly Arg Pro Ser Met Ala Glu Asp Arg Ser Thr Val Thr Ala
145                 150                 155                 160

Ala Thr Gly Met Thr Val Thr Pro Ala Ser Thr Ser Val Val Lys Gly
                165                 170                 175

Gln Ser Thr Thr Leu Thr Val Ala Phe Gln Pro Glu Gly Val Thr Asp
                180                 185                 190

Lys Ser Phe Arg Ala Val Ser Ala Asp Lys Thr Lys Ala Thr Val Ser
            195                 200                 205

Val Ser Gly Met Thr Ile Thr Val Asn Gly Val Ala Ala Gly Lys Val
        210                 215                 220

Asn Ile Pro Val Val Ser Gly Asn Gly Glu Phe Ala Ala Val Ala Glu
225                 230                 235                 240

Ile Thr Val Thr Ala Ser
                245

<210> SEQ ID NO 21
<211> LENGTH: 252
<212> TYPE: PRT
<213> ORGANISM: Bacteriophage SPP1

<400> SEQUENCE: 21

Asn Ile Tyr Asp Ile Leu Asp Lys Val Phe Thr Met Met Tyr Asp Gly
1                   5                   10                  15

Gln Asp Leu Thr Asp Tyr Phe Leu Val Gln Glu Val Arg Gly Arg Ser
                20                  25                  30

Val Tyr Ser Ile Glu Met Gly Lys Arg Thr Ile Ala Gly Val Asp Gly
            35                  40                  45

Gly Val Ile Thr Thr Glu Ser Leu Pro Ala Arg Glu Leu Glu Val Asp
        50                  55                  60

Ala Ile Val Phe Gly Asp Gly Thr Glu Thr Asp Leu Arg Arg Arg Ile
65                  70                  75                  80

Glu Tyr Leu Asn Phe Leu Leu His Arg Asp Thr Asp Val Pro Ile Thr
                85                  90                  95

Phe Ser Asp Glu Pro Ser Arg Thr Tyr Tyr Gly Arg Tyr Glu Phe Ala
                100                 105                 110

Thr Glu Gly Asp Glu Lys Gly Gly Phe His Lys Val Thr Leu Asn Phe
            115                 120                 125

Tyr Cys Gln Asp Pro Leu Lys Tyr Gly Pro Glu Val Thr Thr Asp Val
        130                 135                 140

Thr Thr Ala Ser Thr Pro Val Lys Asn Thr Gly Leu Ala Val Thr Asn
145                 150                 155                 160

Pro Thr Ile Arg Cys Val Phe Ser Thr Ser Ala Thr Glu Tyr Glu Met
                165                 170                 175

Gln Leu Leu Asp Gly Ser Thr Val Val Lys Phe Leu Lys Val Val Tyr
                180                 185                 190

Gly Phe Asn Thr Gly Asp Thr Leu Val Ile Asp Cys His Glu Arg Ser
            195                 200                 205

Val Thr Leu Asn Gly Gln Asp Ile Met Pro Ala Leu Leu Ile Gln Ser
        210                 215                 220

Asp Trp Ile Gln Leu Lys Pro Gln Val Asn Thr Tyr Leu Lys Ala Thr
225                 230                 235                 240

Gln Pro Ser Thr Ile Val Phe Thr Glu Lys Phe Leu
```

-continued

```
                      245                  250

<210> SEQ ID NO 22
<211> LENGTH: 464
<212> TYPE: PRT
<213> ORGANISM: Escherichia phage T5

<400> SEQUENCE: 22

Met Ser Leu Gln Leu Leu Arg Asn Thr Arg Ile Phe Val Ser Thr Val
1               5                   10                  15

Lys Thr Gly His Asn Lys Thr Asn Thr Gln Glu Ile Leu Val Gln Asp
                20                  25                  30

Asp Ile Ser Trp Gly Gln Asp Ser Asn Ser Thr Asp Ile Thr Val Asn
            35                  40                  45

Glu Ala Gly Pro Arg Pro Thr Arg Gly Ser Lys Arg Phe Asn Asp Ser
    50                  55                  60

Leu Asn Ala Ala Glu Trp Ser Phe Ser Thr Tyr Ile Leu Pro Tyr Lys
65                  70                  75                  80

Asp Lys Asn Thr Ser Lys Gln Ile Val Pro Asp Tyr Met Leu Trp His
                85                  90                  95

Ala Leu Ser Ser Gly Arg Ala Ile Asn Leu Glu Gly Thr Thr Gly Ala
            100                 105                 110

His Asn Asn Ala Thr Asn Phe Met Val Asn Phe Lys Asp Asn Ser Tyr
            115                 120                 125

His Glu Leu Ala Met Leu His Ile Tyr Ile Leu Thr Asp Lys Thr Trp
        130                 135                 140

Ser Tyr Ile Asp Ser Cys Gln Ile Asn Gln Ala Glu Val Asn Val Asp
145                 150                 155                 160

Ile Glu Asp Ile Gly Arg Val Thr Trp Ser Gly Asn Gly Asn Gln Leu
                165                 170                 175

Ile Pro Leu Asp Glu Gln Pro Phe Asp Pro Asp Gln Ile Gly Ile Asp
            180                 185                 190

Asp Glu Thr Tyr Met Thr Ile Gln Gly Ser Tyr Ile Lys Asn Lys Leu
            195                 200                 205

Thr Ile Leu Lys Ile Lys Asp Met Asp Thr Asn Lys Ser Tyr Asp Ile
        210                 215                 220

Pro Ile Thr Gly Gly Thr Phe Thr Ile Asn Asn Asn Ile Thr Tyr Leu
225                 230                 235                 240

Thr Pro Asn Val Met Ser Arg Val Thr Ile Pro Ile Gly Ser Phe Thr
            245                 250                 255

Gly Ala Phe Glu Leu Thr Gly Ser Leu Thr Ala Tyr Leu Asn Asp Lys
            260                 265                 270

Ser Leu Gly Ser Met Glu Leu Tyr Lys Asp Leu Ile Lys Thr Leu Lys
            275                 280                 285

Val Val Asn Arg Phe Glu Ile Ala Leu Val Leu Gly Gly Glu Tyr Asp
        290                 295                 300

Asp Glu Arg Pro Ala Ala Ile Leu Val Ala Lys Gln Ala His Val Asn
305                 310                 315                 320

Ile Pro Thr Ile Glu Thr Asp Asp Val Leu Gly Thr Ser Val Glu Phe
                325                 330                 335

Lys Ala Ile Pro Ser Asp Leu Asp Ala Gly Asp Glu Gly Tyr Leu Gly
            340                 345                 350

Phe Ser Ser Lys Tyr Thr Arg Thr Thr Ile Asn Asn Leu Ile Val Asn
            355                 360                 365
```

```
Gly Asp Gly Ala Thr Asp Ala Val Thr Ala Ile Thr Val Lys Ser Ala
    370             375                 380

Gly Asn Val Thr Thr Leu Asn Arg Ser Ala Thr Leu Gln Met Ser Val
385             390                 395                 400

Glu Val Thr Pro Ser Ser Ala Arg Asn Lys Glu Val Thr Trp Ala Ile
            405                 410                 415

Thr Ala Gly Asp Ala Ala Thr Ile Asn Ala Thr Gly Leu Leu Arg Ala
            420                 425                 430

Asp Ala Ser Lys Thr Gly Ala Val Thr Val Glu Ala Thr Ala Lys Asp
            435                 440                 445

Gly Ser Gly Val Lys Gly Thr Lys Val Ile Thr Val Thr Ala Gly Gly
    450                 455                 460

<210> SEQ ID NO 23
<211> LENGTH: 118
<212> TYPE: PRT
<213> ORGANISM: Escherichia phage Mu

<400> SEQUENCE: 23

Met Ala Gly Asn Gln Arg Gln Gly Val Ala Phe Ile Arg Val Asn Gly
1               5                   10                  15

Met Glu Leu Glu Ser Met Glu Gly Ala Ser Phe Thr Pro Ser Gly Ile
            20                  25                  30

Thr Arg Glu Glu Val Thr Gly Ser Arg Val Tyr Gly Trp Lys Gly Lys
            35                  40                  45

Pro Arg Ala Ala Lys Val Glu Cys Lys Ile Pro Gly Gly Gly Pro Ile
    50                  55                  60

Gly Leu Asp Glu Ile Ile Asp Trp Glu Asn Ile Thr Val Glu Phe Gln
65                  70                  75                  80

Ala Asp Thr Gly Glu Thr Trp Met Leu Ala Asn Ala Trp Gln Ala Asp
                85                  90                  95

Glu Pro Lys Asn Asp Gly Gly Glu Ile Ser Leu Val Leu Met Ala Lys
            100                 105                 110

Gln Ser Lys Arg Ile Ala
        115

<210> SEQ ID NO 24
<211> LENGTH: 246
<212> TYPE: PRT
<213> ORGANISM: Bacteriophage lambda

<400> SEQUENCE: 24

Met Pro Val Pro Asn Pro Thr Met Pro Val Lys Gly Ala Gly Thr Thr
1               5                   10                  15

Leu Trp Val Tyr Lys Gly Ser Gly Asp Pro Tyr Ala Asn Pro Leu Ser
            20                  25                  30

Asp Val Asp Trp Ser Arg Leu Ala Lys Val Lys Asp Leu Thr Pro Gly
            35                  40                  45

Glu Leu Thr Ala Glu Ser Tyr Asp Asp Ser Tyr Leu Asp Asp Glu Asp
    50                  55                  60

Ala Asp Trp Thr Ala Thr Gly Gln Gly Gln Lys Ser Ala Gly Asp Thr
65                  70                  75                  80

Ser Phe Thr Leu Ala Trp Met Pro Gly Glu Gln Gly Gln Gln Ala Leu
                85                  90                  95

Leu Ala Trp Phe Asn Glu Gly Asp Thr Arg Ala Tyr Lys Ile Arg Phe
            100                 105                 110
```

-continued

```
Pro Asn Gly Thr Val Asp Val Phe Arg Gly Trp Val Ser Ser Ile Gly
        115             120             125

Lys Ala Val Thr Ala Lys Glu Val Ile Thr Arg Thr Val Lys Val Thr
    130             135             140

Asn Val Gly Arg Pro Ser Met Ala Glu Asp Arg Ser Thr Val Thr Ala
145             150             155             160

Ala Thr Gly Met Thr Val Thr Pro Ala Ser Thr Ser Val Val Lys Gly
                165             170             175

Gln Ser Thr Thr Leu Thr Val Ala Phe Gln Pro Glu Gly Val Thr Asp
            180             185             190

Lys Ser Phe Arg Ala Val Ser Ala Asp Lys Thr Lys Ala Thr Val Ser
            195             200             205

Val Ser Gly Met Thr Ile Thr Val Asn Gly Val Ala Ala Gly Lys Val
        210             215             220

Asn Ile Pro Val Val Ser Gly Asn Gly Glu Phe Ala Ala Val Ala Glu
225             230             235             240

Ile Thr Val Thr Ala Ser
                245

<210> SEQ ID NO 25
<211> LENGTH: 301
<212> TYPE: PRT
<213> ORGANISM: Lactococcus phage F4-1

<400> SEQUENCE: 25

Met Lys Leu Asp Tyr Asn Ser Arg Glu Ile Phe Phe Gly Asn Glu Ala
1               5               10              15

Leu Ile Val Ala Asp Met Thr Lys Gly Ser Asn Gly Lys Pro Glu Phe
                20              25              30

Thr Asn His Lys Ile Val Thr Gly Leu Val Ser Val Gly Ser Met Glu
            35              40              45

Asp Gln Ala Glu Thr Asn Ser Tyr Pro Ala Asp Val Pro Asp His
        50              55              60

Gly Val Lys Lys Gly Ala Thr Leu Leu Gln Gly Glu Met Val Phe Ile
65              70              75              80

Gln Thr Asp Gln Ala Leu Lys Glu Asp Met Leu Gly Gln Gln Arg Thr
                85              90              95

Glu Asn Gly Leu Gly Trp Ser Pro Thr Gly Asn Trp Lys Thr Lys Cys
            100             105             110

Val Gln Tyr Leu Ile Lys Gly Arg Lys Arg Asp Lys Val Thr Gly Glu
            115             120             125

Phe Val Asp Gly Tyr Arg Val Val Val Tyr Pro His Leu Thr Pro Thr
        130             135             140

Ala Glu Ala Thr Lys Glu Ser Glu Thr Asp Ser Val Asp Gly Val Asp
145             150             155             160

Pro Ile Gln Trp Thr Leu Ala Val Gln Ala Thr Glu Ser Asp Ile Tyr
                165             170             175

Ser Asn Gly Gly Lys Lys Val Pro Ala Ile Glu Tyr Glu Ile Trp Gly
            180             185             190

Glu Gln Ala Lys Asp Phe Ala Lys Lys Met Glu Ser Gly Leu Phe Ile
            195             200             205

Met Gln Pro Asp Thr Val Leu Ala Gly Ala Ile Thr Leu Val Ala Pro
        210             215             220

Val Ile Pro Asn Val Thr Thr Ala Thr Lys Gly Asn Asn Asp Gly Thr
225             230             235             240
```

-continued

```
Ile Val Val Pro Asp Thr Leu Lys Asp Ser Lys Gly Gly Thr Val Lys
                245                 250                 255

Val Thr Ser Val Ile Lys Asp Ala His Gly Lys Val Ala Thr Asn Gly
                260                 265                 270

Gln Leu Ala Pro Gly Val Tyr Ile Val Thr Phe Ser Ala Asp Gly Tyr
            275                 280                 285

Glu Asp Val Thr Ala Gly Val Ser Val Thr Asp His Ser
    290                 295                 300

<210> SEQ ID NO 26
<211> LENGTH: 172
<212> TYPE: PRT
<213> ORGANISM: Bacteriophage P2

<400> SEQUENCE: 26

Met Ala Met Pro Arg Lys Leu Lys Leu Met Asn Val Phe Leu Asn Gly
1               5                   10                  15

Tyr Ser Tyr Gln Gly Val Ala Lys Ser Val Thr Leu Pro Lys Leu Thr
                20                  25                  30

Arg Lys Leu Glu Asn Tyr Arg Gly Ala Gly Met Asn Gly Ser Ala Pro
            35                  40                  45

Val Asp Leu Gly Leu Asp Asp Asp Ala Leu Ser Met Glu Trp Ser Leu
    50                  55                  60

Gly Gly Phe Pro Asp Ser Val Ile Trp Glu Leu Tyr Ala Ala Thr Gly
65                  70                  75                  80

Val Asp Ala Val Pro Ile Arg Phe Ala Gly Ser Tyr Gln Arg Asp Asp
                85                  90                  95

Thr Gly Glu Thr Val Ala Val Glu Val Val Met Arg Gly Arg Gln Lys
                100                 105                 110

Glu Ile Asp Thr Gly Glu Gly Lys Gln Gly Glu Asp Thr Glu Ser Lys
            115                 120                 125

Ile Ser Val Val Cys Thr Tyr Phe Arg Leu Thr Met Asp Gly Lys Glu
    130                 135                 140

Leu Val Glu Ile Asp Thr Ile Asn Met Ile Glu Lys Val Asn Gly Val
145                 150                 155                 160

Asp Arg Leu Glu Gln His Arg Arg Asn Ile Gly Leu
                165                 170

<210> SEQ ID NO 27
<211> LENGTH: 177
<212> TYPE: PRT
<213> ORGANISM: Serratia phage KSP90

<400> SEQUENCE: 27

Met Ala Thr Val Asn Glu Phe Arg Gly Ala Met Ser Arg Gly Gly Gly
1               5                   10                  15

Val Gln Arg Gln His Arg Trp Arg Val Thr Ile Ser Phe Pro Ser Phe
                20                  25                  30

Ala Ala Ser Ala Asp Gln Thr Arg Asp Val Cys Leu Leu Ala Val Thr
            35                  40                  45

Thr Asn Thr Pro Thr Gly Gln Leu Gly Glu Ile Leu Val Pro Trp Gly
    50                  55                  60

Gly Arg Glu Leu Pro Phe Pro Gly Asp Arg Arg Phe Glu Ala Leu Pro
65                  70                  75                  80

Ile Thr Phe Ile Asn Val Val Asn Asn Gly Pro Tyr Asn Ser Met Glu
                85                  90                  95
```

```
Val Trp Gln Gln Tyr Ile Asn Gly Ser Glu Ser Asn Arg Ala Ser Ala
                100                 105                 110

Asn Pro Asp Glu Tyr Phe Arg Asp Val Val Leu Glu Leu Leu Asp Ala
                115                 120                 125

Asn Asp Asn Val Thr Lys Thr Trp Thr Leu Gln Gly Ala Trp Pro Gln
            130                 135                 140

Asn Leu Gly Gln Leu Glu Leu Asp Met Ser Ala Met Asp Ser Tyr Thr
145                 150                 155                 160

Gln Phe Thr Cys Asp Leu Arg Tyr Phe Gln Ala Val Ser Asp Arg Ser
                    165                 170                 175

Arg
```

<210> SEQ ID NO 28
<211> LENGTH: 196
<212> TYPE: PRT
<213> ORGANISM: Enterobacteria phage T7M

<400> SEQUENCE: 28

```
Met Arg Ser Tyr Glu Met Asn Ile Glu Thr Ala Glu Glu Leu Ser Ala
1               5                   10                  15

Val Asn Asp Ile Leu Ala Ser Ile Gly Glu Pro Pro Val Ser Thr Leu
                20                  25                  30

Glu Gly Asp Ala Asn Ala Asp Val Ala Asn Ala Arg Arg Val Leu Asn
            35                  40                  45

Lys Ile Asn Arg Gln Ile Gln Ser Arg Gly Trp Thr Phe Asn Ile Glu
        50                  55                  60

Glu Gly Val Thr Leu Leu Pro Asp Ala Phe Ser Gly Met Ile Pro Phe
65                  70                  75                  80

Ser Ser Asp Tyr Leu Ser Val Met Ala Thr Ser Gly Gln Thr Gln Tyr
                    85                  90                  95

Val Asn Arg Gly Gly Tyr Leu Tyr Asp Arg Ser Ala Lys Thr Asp Arg
                100                 105                 110

Phe Pro Ser Gly Val Gln Val Asn Leu Ile Arg Leu Arg Glu Phe Asp
                115                 120                 125

Glu Met Pro Glu Cys Phe Arg Asn Tyr Ile Val Thr Lys Ala Ser Arg
            130                 135                 140

Gln Phe Asn Asn Arg Phe Phe Gly Ala Pro Glu Val Asp Gly Val Leu
145                 150                 155                 160

Gln Glu Glu Glu Gln Glu Ala Trp Ser Ala Cys Phe Glu Tyr Glu Leu
                    165                 170                 175

Asp Tyr Gly Asn Tyr Asn Met Leu Asp Gly Asp Ala Phe Thr Ser Gly
                180                 185                 190

Leu Leu Asn Arg
            195
```

<210> SEQ ID NO 29
<211> LENGTH: 108
<212> TYPE: PRT
<213> ORGANISM: Bacteriophage HK97

<400> SEQUENCE: 29

```
Met Ala Ile Asp Val Leu Asp Val Ile Ser Leu Ser Leu Phe Lys Gln
1               5                   10                  15

Gln Ile Glu Phe Glu Glu Asp Asp Arg Asp Glu Leu Ile Thr Leu Tyr
                20                  25                  30
```

```
Ala Gln Ala Ala Phe Asp Tyr Cys Met Arg Trp Cys Asp Glu Pro Ala
        35              40              45

Trp Lys Val Ala Ala Asp Ile Pro Ala Ala Val Lys Gly Ala Val Leu
    50              55              60

Leu Val Phe Ala Asp Met Phe Glu His Arg Thr Ala Gln Ser Glu Val
65              70              75              80

Gln Leu Tyr Glu Asn Ala Ala Ala Glu Arg Met Met Phe Ile His Arg
                85              90              95

Asn Trp Arg Gly Lys Ala Glu Ser Glu Glu Gly Ser
            100             105

<210> SEQ ID NO 30
<211> LENGTH: 309
<212> TYPE: PRT
<213> ORGANISM: Bacteriophage phi-29

<400> SEQUENCE: 30

Met Ala Arg Lys Arg Ser Asn Thr Tyr Arg Ser Ile Asn Glu Ile Gln
1               5               10              15

Arg Gln Lys Arg Asn Arg Trp Phe Ile His Tyr Leu Asn Tyr Leu Gln
            20              25              30

Ser Leu Ala Tyr Gln Leu Phe Glu Trp Glu Asn Leu Pro Pro Thr Ile
        35              40              45

Asn Pro Ser Phe Leu Glu Lys Ser Ile His Gln Phe Gly Tyr Val Gly
        50              55              60

Phe Tyr Lys Asp Pro Val Ile Ser Tyr Ile Ala Cys Asn Gly Ala Leu
65              70              75              80

Ser Gly Gln Arg Asp Val Tyr Asn Gln Ala Thr Val Phe Arg Ala Ala
                85              90              95

Ser Pro Val Tyr Gln Lys Glu Phe Lys Leu Tyr Asn Tyr Arg Asp Met
            100             105             110

Lys Glu Glu Asp Met Gly Val Val Ile Tyr Asn Asn Asp Met Ala Phe
            115             120             125

Pro Thr Thr Pro Thr Leu Glu Leu Phe Ala Ala Glu Leu Ala Glu Leu
        130             135             140

Lys Glu Ile Ile Ser Val Asn Gln Asn Ala Gln Lys Thr Pro Val Leu
145             150             155             160

Ile Arg Ala Asn Asp Asn Asn Gln Leu Ser Leu Lys Gln Val Tyr Asn
            165             170             175

Gln Tyr Glu Gly Asn Ala Pro Val Ile Phe Ala His Glu Ala Leu Asp
            180             185             190

Ser Asp Ser Ile Glu Val Phe Lys Thr Asp Ala Pro Tyr Val Val Asp
            195             200             205

Lys Leu Asn Ala Gln Lys Asn Ala Val Trp Asn Glu Met Met Thr Phe
        210             215             220

Leu Gly Ile Lys Asn Ala Asn Leu Glu Lys Lys Glu Arg Met Val Thr
225             230             235             240

Asp Glu Val Ser Ser Asn Asp Glu Gln Ile Glu Ser Ser Gly Thr Val
            245             250             255

Phe Leu Lys Ser Arg Glu Glu Ala Cys Glu Lys Ile Asn Glu Leu Tyr
            260             265             270

Gly Leu Asn Val Lys Val Lys Phe Arg Tyr Asp Ile Val Glu Gln Met
        275             280             285

Arg Arg Glu Leu Gln Gln Ile Glu Asn Val Ser Arg Gly Thr Ser Asp
        290             295             300
```

```
Gly Glu Thr Asn Glu
305

<210> SEQ ID NO 31
<211> LENGTH: 315
<212> TYPE: PRT
<213> ORGANISM: Bacteriophage phi-29

<400> SEQUENCE: 31

Thr Tyr Arg Ser Ile Asn Glu Ile Gln Arg Gln Lys Arg Asn Arg Trp
1               5                   10                  15

Phe Ile His Tyr Leu Asn Tyr Leu Gln Ser Leu Ala Tyr Gln Leu Phe
            20                  25                  30

Glu Trp Glu Asn Leu Pro Pro Thr Ile Asn Pro Ser Phe Leu Glu Lys
        35                  40                  45

Ser Ile His Gln Phe Gly Tyr Val Gly Phe Tyr Lys Asp Pro Val Ile
    50                  55                  60

Ser Tyr Ile Ala Cys Asn Gly Ala Leu Ser Gly Gln Arg Asp Val Tyr
65                  70                  75                  80

Asn Gln Ala Thr Val Phe Arg Ala Ala Ser Pro Val Tyr Gln Lys Glu
                85                  90                  95

Phe Lys Leu Tyr Asn Tyr Arg Asp Met Lys Glu Glu Asp Met Gly Val
            100                 105                 110

Val Ile Tyr Asn Asn Asp Met Ala Phe Pro Thr Thr Pro Thr Leu Glu
            115                 120                 125

Leu Phe Ala Ala Glu Leu Ala Glu Leu Lys Glu Ile Ile Ser Val Asn
        130                 135                 140

Gln Asn Ala Gln Lys Thr Pro Val Leu Ile Arg Ala Asn Asp Asn Asn
145                 150                 155                 160

Gln Leu Ser Leu Lys Gln Val Tyr Asn Gln Tyr Glu Gly Asn Ala Pro
                165                 170                 175

Val Ile Phe Ala His Glu Ala Leu Asp Ser Asp Ser Ile Glu Val Phe
            180                 185                 190

Lys Thr Asp Ala Pro Tyr Val Val Asp Lys Leu Asn Ala Gln Lys Asn
            195                 200                 205

Ala Val Trp Asn Glu Met Met Thr Phe Leu Gly Ile Lys Asn Ala Asn
        210                 215                 220

Leu Glu Lys Lys Glu Arg Met Val Thr Asp Glu Val Ser Ser Asn Asp
225                 230                 235                 240

Glu Gln Ile Glu Ser Ser Gly Thr Val Phe Leu Lys Ser Arg Glu Glu
                245                 250                 255

Ala Cys Glu Lys Ile Asn Glu Leu Tyr Gly Leu Asn Val Lys Val Lys
            260                 265                 270

Phe Arg Tyr Asp Ile Val Glu Gln Met Arg Arg Glu Leu Gln Gln Ile
            275                 280                 285

Glu Asn Val Ser Arg Gly Thr Ser Asp Gly Glu Thr Asn Glu Ala His
        290                 295                 300

Ile Val Met Val Asp Ala Tyr Lys Pro Thr Lys
305                 310                 315

<210> SEQ ID NO 32
<211> LENGTH: 315
<212> TYPE: PRT
<213> ORGANISM: Bacteriophage phi-29

<400> SEQUENCE: 32
```

-continued

```
Thr Tyr Leu Ser Ile Asn Val Ile Gln Leu Gln Lys Arg Asn Arg Trp
1               5                   10                  15

Phe Ile His Tyr Leu Asn Tyr Leu Gln Ser Leu Ala Tyr Gln Leu Phe
            20                  25                  30

Glu Trp Glu Asn Leu Pro Pro Thr Ile Asn Pro Ser Phe Leu Glu Lys
        35                  40                  45

Ser Ile His Gln Phe Gly Tyr Val Gly Phe Tyr Lys Asp Pro Val Ile
    50                  55                  60

Ser Tyr Ile Ala Cys Asn Gly Ala Leu Ser Gly Gln Arg Asp Val Tyr
65                  70                  75                  80

Asn Gln Ala Thr Val Phe Arg Ala Ala Ser Pro Val Tyr Gln Lys Glu
                85                  90                  95

Phe Lys Leu Tyr Asn Tyr Arg Asp Met Lys Glu Glu Asp Met Gly Val
            100                 105                 110

Val Ile Tyr Asn Asn Asp Met Ala Phe Pro Thr Thr Pro Thr Leu Glu
            115                 120                 125

Leu Phe Ala Ala Glu Leu Ala Glu Leu Lys Glu Ile Ile Ser Val Asn
    130                 135                 140

Gln Asn Ala Gln Lys Thr Pro Val Leu Ile Arg Ala Asn Asp Asn Asn
145                 150                 155                 160

Gln Leu Ser Leu Lys Gln Val Tyr Asn Gln Tyr Glu Gly Asn Ala Pro
            165                 170                 175

Val Ile Phe Ala His Glu Ala Leu Asp Ser Asp Ser Ile Glu Val Phe
            180                 185                 190

Lys Thr Asp Ala Pro Tyr Val Val Asp Lys Leu Asn Ala Gln Lys Asn
            195                 200                 205

Ala Val Trp Asn Glu Met Met Thr Phe Leu Gly Ile Lys Asn Ala Asn
    210                 215                 220

Leu Glu Lys Lys Glu Arg Met Val Thr Asp Glu Val Ser Ser Asn Asp
225                 230                 235                 240

Glu Gln Ile Glu Ser Ser Gly Thr Val Phe Leu Lys Ser Arg Glu Glu
            245                 250                 255

Ala Cys Glu Lys Ile Asn Glu Leu Tyr Gly Leu Asn Val Lys Val Lys
            260                 265                 270

Phe Arg Tyr Asp Ile Val Glu Gln Met Arg Arg Glu Leu Gln Gln Ile
            275                 280                 285

Glu Asn Val Ser Arg Gly Thr Ser Asp Gly Glu Thr Asn Glu Ala His
    290                 295                 300

Ile Val Met Val Asp Ala Tyr Lys Pro Thr Lys
305                 310                 315
```

```
<210> SEQ ID NO 33
<211> LENGTH: 317
<212> TYPE: PRT
<213> ORGANISM: Bacteriophage phi-29

<400> SEQUENCE: 33

Ile Leu Thr Tyr Leu Ser Ile Asn Val Ile Gln Leu Gln Lys Arg Asn
1               5                   10                  15

Arg Trp Phe Ile His Tyr Leu Asn Tyr Leu Gln Ser Leu Ala Tyr Gln
            20                  25                  30

Leu Phe Glu Trp Glu Asn Leu Pro Pro Thr Ile Asn Pro Ser Phe Leu
        35                  40                  45

Glu Lys Ser Ile His Gln Phe Gly Tyr Val Gly Phe Tyr Lys Asp Pro
```

-continued

```
         50                55                60

Val Ile Ser Tyr Ile Ala Cys Asn Gly Ala Leu Ser Gly Gln Arg Asp
65                70                75                80

Val Tyr Asn Gln Ala Thr Val Phe Arg Ala Ala Ser Pro Val Tyr Gln
                85                90                95

Lys Glu Phe Lys Leu Tyr Asn Tyr Arg Asp Met Lys Glu Glu Asp Met
             100               105               110

Gly Val Val Ile Tyr Asn Asn Asp Met Ala Phe Pro Thr Thr Pro Thr
         115               120               125

Leu Glu Leu Phe Ala Ala Glu Leu Ala Glu Leu Lys Glu Ile Ile Ser
         130               135               140

Val Asn Gln Asn Ala Gln Lys Thr Pro Val Leu Ile Arg Ala Asn Asp
145               150               155               160

Asn Asn Gln Leu Ser Leu Lys Gln Val Tyr Asn Gln Tyr Glu Gly Asn
             165               170               175

Ala Pro Val Ile Phe Ala His Glu Ala Leu Asp Ser Asp Ser Ile Glu
             180               185               190

Val Phe Lys Thr Asp Ala Pro Tyr Val Val Asp Lys Leu Asn Ala Gln
             195               200               205

Lys Asn Ala Val Trp Asn Glu Met Met Thr Phe Leu Gly Ile Lys Asn
         210               215               220

Ala Asn Leu Glu Lys Lys Glu Arg Met Val Thr Asp Glu Val Ser Ser
225               230               235               240

Asn Asp Glu Gln Ile Glu Ser Ser Gly Thr Val Phe Leu Lys Ser Arg
             245               250               255

Glu Glu Ala Cys Glu Lys Ile Asn Glu Leu Tyr Gly Leu Asn Val Lys
             260               265               270

Val Lys Phe Arg Tyr Asp Ile Val Glu Gln Met Arg Arg Glu Leu Gln
             275               280               285

Gln Ile Glu Asn Val Ser Arg Gly Thr Ser Asp Gly Glu Thr Asn Glu
         290               295               300

Ala His Ile Val Met Val Asp Ala Tyr Lys Pro Thr Lys
305               310               315

<210> SEQ ID NO 34
<211> LENGTH: 321
<212> TYPE: PRT
<213> ORGANISM: Bacteriophage phi-29

<400> SEQUENCE: 34

Ile Leu Val Ala Ile Leu Thr Tyr Leu Ser Ile Asn Val Ile Gln Leu
1                 5                 10                15

Gln Lys Arg Asn Arg Trp Phe Ile His Tyr Leu Asn Tyr Leu Gln Ser
             20                25                30

Leu Ala Tyr Gln Leu Phe Glu Trp Glu Asn Leu Pro Pro Thr Ile Asn
         35                40                45

Pro Ser Phe Leu Glu Lys Ser Ile His Gln Phe Gly Tyr Val Gly Phe
         50                55                60

Tyr Lys Asp Pro Val Ile Ser Tyr Ile Ala Cys Asn Gly Ala Leu Ser
65                70                75                80

Gly Gln Arg Asp Val Tyr Asn Gln Ala Thr Val Phe Arg Ala Ala Ser
             85                90                95

Pro Val Tyr Gln Lys Glu Phe Lys Leu Tyr Asn Tyr Arg Asp Met Lys
             100               105               110
```

-continued

```
Glu Glu Asp Met Gly Val Val Ile Tyr Asn Asn Asp Met Ala Phe Pro
    115                 120                 125

Thr Thr Pro Thr Leu Glu Leu Phe Ala Ala Glu Leu Ala Glu Leu Lys
    130                 135                 140

Glu Ile Ile Ser Val Asn Gln Asn Ala Gln Lys Thr Pro Val Leu Ile
145                 150                 155                 160

Arg Ala Asn Asp Asn Asn Gln Leu Ser Leu Lys Gln Val Tyr Asn Gln
                165                 170                 175

Tyr Glu Gly Asn Ala Pro Val Ile Phe Ala His Glu Ala Leu Asp Ser
                180                 185                 190

Asp Ser Ile Glu Val Phe Lys Thr Asp Ala Pro Tyr Val Val Asp Lys
                195                 200                 205

Leu Asn Ala Gln Lys Asn Ala Val Trp Asn Glu Met Met Thr Phe Leu
    210                 215                 220

Gly Ile Lys Asn Ala Asn Leu Glu Lys Lys Glu Arg Met Val Thr Asp
225                 230                 235                 240

Glu Val Ser Ser Asn Asp Glu Gln Ile Glu Ser Ser Gly Thr Val Phe
                245                 250                 255

Leu Lys Ser Arg Glu Glu Ala Cys Glu Lys Ile Asn Glu Leu Tyr Gly
                260                 265                 270

Leu Asn Val Lys Val Lys Phe Arg Tyr Asp Ile Val Glu Gln Met Arg
                275                 280                 285

Arg Glu Leu Gln Gln Ile Glu Asn Val Ser Arg Gly Thr Ser Asp Gly
    290                 295                 300

Glu Thr Asn Glu Ala His Ile Val Met Val Asp Ala Tyr Lys Pro Thr
305                 310                 315                 320

Lys
```

```
<210> SEQ ID NO 35
<211> LENGTH: 309
<212> TYPE: PRT
<213> ORGANISM: Bacteriophage phi-29

<400> SEQUENCE: 35
```

```
Met Ala Arg Lys Arg Ser Asn Thr Tyr Arg Ser Ile Asn Glu Ile Gln
1                   5                   10                  15

Arg Gln Lys Arg Asn Arg Trp Phe Ile His Tyr Leu Asn Tyr Leu Gln
                20                  25                  30

Ser Leu Ala Tyr Gln Leu Phe Glu Trp Glu Asn Leu Pro Pro Thr Ile
        35                  40                  45

Asn Pro Ser Phe Leu Glu Lys Ser Ile His Gln Phe Gly Tyr Val Gly
    50                  55                  60

Phe Tyr Lys Asp Pro Val Ile Ser Tyr Ile Ala Cys Asn Gly Cys Leu
65                  70                  75                  80

Ser Gly Gln Arg Asp Val Tyr Asn Gln Ala Thr Val Phe Arg Ala Ala
                85                  90                  95

Ser Pro Val Tyr Gln Lys Glu Phe Lys Leu Tyr Asn Tyr Arg Asp Met
                100                 105                 110

Lys Glu Glu Asp Met Gly Val Val Ile Tyr Asn Asn Asp Met Ala Phe
    115                 120                 125

Pro Thr Thr Pro Thr Leu Cys Leu Phe Ala Ala Glu Leu Ala Glu Leu
    130                 135                 140

Lys Glu Ile Ile Ser Val Asn Gln Asn Ala Gln Lys Thr Pro Val Leu
145                 150                 155                 160
```

```
Ile Arg Ala Asn Asp Asn Asn Cys Leu Ser Leu Lys Gln Val Tyr Asn
            165                 170                 175

Gln Tyr Glu Gly Asn Ala Pro Val Ile Phe Ala His Glu Ala Leu Asp
            180                 185                 190

Ser Asp Ser Ile Glu Val Phe Lys Thr Asp Ala Pro Tyr Val Val Asp
            195                 200                 205

Lys Leu Asn Ala Gln Lys Asn Ala Val Trp Asn Glu Met Met Thr Phe
    210                 215                 220

Leu Gly Ile Lys Asn Ala Asn Leu Glu Lys Lys Glu Arg Met Val Thr
225                 230                 235                 240

Asp Glu Val Ser Ser Asn Asp Glu Gln Ile Glu Ser Ser Gly Thr Val
            245                 250                 255

Phe Leu Lys Ser Arg Glu Glu Ala Cys Glu Lys Ile Asn Glu Leu Tyr
            260                 265                 270

Gly Leu Asn Val Lys Val Lys Phe Arg Tyr Asp Ile Val Glu Gln Met
            275                 280                 285

Arg Arg Glu Leu Gln Gln Ile Glu Asn Val Ser Arg Gly Thr Ser Asp
    290                 295                 300

Gly Glu Thr Asn Glu
305

<210> SEQ ID NO 36
<211> LENGTH: 13
<212> TYPE: PRT
<213> ORGANISM: Artificial
<220> FEATURE:
<223> OTHER INFORMATION: Synthetic

<400> SEQUENCE: 36

Ala His Ile Val Met Val Asp Ala Tyr Lys Pro Thr Lys
1               5                   10

<210> SEQ ID NO 37
<211> LENGTH: 129
<212> TYPE: PRT
<213> ORGANISM: Artificial
<220> FEATURE:
<223> OTHER INFORMATION: Synthetic

<400> SEQUENCE: 37

Asp Tyr Asp Ile Pro Thr Thr Glu Asn Leu Tyr Phe Gln Gly Ala Met
1               5                   10                  15

Val Asp Thr Leu Ser Gly Leu Ser Ser Glu Gln Gly Gln Ser Gly Asp
            20                  25                  30

Met Thr Ile Glu Glu Asp Ser Ala Thr His Ile Lys Phe Ser Lys Arg
            35                  40                  45

Asp Glu Asp Gly Lys Glu Leu Ala Gly Ala Thr Met Glu Leu Arg Asp
    50                  55                  60

Ser Ser Gly Lys Thr Ile Ser Thr Trp Ile Ser Asp Gly Gln Val Lys
65                  70                  75                  80

Asp Phe Tyr Leu Tyr Pro Gly Lys Tyr Thr Phe Val Glu Thr Ala Ala
            85                  90                  95

Pro Asp Gly Tyr Glu Val Ala Thr Ala Ile Thr Phe Thr Val Asn Glu
            100                 105                 110

Gln Gly Gln Val Thr Val Asn Gly Lys Ala Thr Lys Gly Asp Ala His
            115                 120                 125

Ile
```

-continued

<210> SEQ ID NO 38
<211> LENGTH: 249
<212> TYPE: PRT
<213> ORGANISM: Artificial
<220> FEATURE:
<223> OTHER INFORMATION: Synthetic

<400> SEQUENCE: 38

Met Ala Leu Thr Gln Pro Ser Ser Val Ser Ala Asn Pro Gly Glu Thr
1               5                   10                  15

Val Lys Ile Thr Cys Ser Gly Ser Ser Gly Ser Tyr Gly Trp Tyr Gln
            20                  25                  30

Gln Lys Ser Pro Asp Ser Ala Pro Val Thr Val Ile Tyr Gln Ser Asn
        35                  40                  45

Gln Arg Pro Ser Asp Ile Pro Ser Arg Phe Ser Gly Ser Lys Ser Gly
    50                  55                  60

Ser Thr Gly Thr Leu Thr Ile Thr Gly Val Gln Ala Glu Asp Glu Ala
65                  70                  75                  80

Val Tyr Tyr Cys Gly Gly Trp Gly Ser Ser Val Gly Met Phe Gly Ala
                85                  90                  95

Gly Thr Thr Leu Thr Val Leu Gly Gln Ser Ser Arg Ser Ser Gly Gly
            100                 105                 110

Gly Gly Ser Ser Gly Gly Gly Gly Ser Ala Val Thr Leu Asp Glu Ser
        115                 120                 125

Gly Gly Gly Leu Gln Thr Pro Gly Gly Ala Leu Ser Leu Val Cys Lys
    130                 135                 140

Ala Ser Gly Phe Thr Phe Ser Ser Tyr Ala Met Gly Trp Val Arg Gln
145                 150                 155                 160

Ala Pro Gly Lys Gly Leu Glu Trp Val Ala Gly Ile Ser Asp Asp Gly
            165                 170                 175

Asp Ser Tyr Ile Ser Tyr Ala Thr Ala Val Lys Gly Arg Ala Thr Ile
            180                 185                 190

Ser Arg Asp Asn Gly Gln Ser Thr Val Arg Leu Gln Leu Asn Asn Leu
        195                 200                 205

Arg Ala Glu Asp Thr Ala Thr Tyr Tyr Cys Ala Arg Ser His Cys Ser
    210                 215                 220

Gly Cys Arg Asn Ala Ala Leu Ile Asp Ala Trp Gly His Gly Thr Glu
225                 230                 235                 240

Val Ile Val Ser Ser Met Ser Tyr Tyr
                245

<210> SEQ ID NO 39
<211> LENGTH: 7
<212> TYPE: PRT
<213> ORGANISM: Artificial
<220> FEATURE:
<223> OTHER INFORMATION: Synthetic

<400> SEQUENCE: 39

Val His Ser Pro Asn Lys Lys
1               5

<210> SEQ ID NO 40
<211> LENGTH: 241
<212> TYPE: PRT
<213> ORGANISM: Artificial
<220> FEATURE:
<223> OTHER INFORMATION: Synthetic -continued

<400> SEQUENCE: 40

```
Glu Val His Leu Gln Gln Ser Leu Ala Glu Leu Val Arg Ser Gly Ala
1               5                   10                  15

Ser Val Lys Leu Ser Cys Thr Ala Ser Gly Phe Asn Ile Lys His Tyr
            20                  25                  30

Tyr Met His Trp Val Lys Gln Arg Pro Glu Gln Gly Leu Glu Trp Ile
        35                  40                  45

Gly Trp Ile Asn Pro Glu Asn Val Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn His Tyr Arg Tyr Ala Val Gly Gly Ala Leu Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Asp Ile Glu Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Ser Val Ser Tyr Ile His Trp Tyr Gln Gln Lys Ser Gly Thr
                165                 170                 175

Ser Pro Lys Arg Trp Val Tyr Asp Thr Ser Lys Leu Ala Ser Gly Val
            180                 185                 190

Pro Ala Arg Phe Ser Gly Ser Gly Ser Gly Thr Ser Tyr Ser Leu Thr
        195                 200                 205

Ile Ser Thr Met Glu Ala Glu Val Ala Ala Thr Tyr Tyr Cys Gln Gln
    210                 215                 220

Trp Asn Asn Asn Pro Tyr Thr Phe Gly Gly Gly Thr Lys Leu Glu Ile
225                 230                 235                 240

Lys
```

<210> SEQ ID NO 41
<211> LENGTH: 116
<212> TYPE: PRT
<213> ORGANISM: Artificial
<220> FEATURE:
<223> OTHER INFORMATION: Synthetic

<400> SEQUENCE: 41

```
Val Lys Leu Gln Glu Ser Gly Pro Gly Leu Val Ala Pro Ser Gln Ser
1               5                   10                  15

Leu Ser Met Ser Cys Thr Val Ser Gly Phe Ser Leu Ser Ser Tyr Gly
            20                  25                  30

Val His Trp Val Arg Gln Pro Pro Gly Lys Gly Leu Glu Trp Leu Gly
        35                  40                  45

Val Ile Trp Ala Gly Gly Thr Thr Asn Tyr Asn Ser Ala Leu Met Ser
    50                  55                  60

Arg Leu Ser Ile Ser Lys Asp Asn Ser Lys Ser Gln Val Leu Leu Lys
65                  70                  75                  80

Met Asn Ser Leu Gln Thr Asp Asp Thr Ala Met Tyr Tyr Cys Ala Thr
                85                  90                  95

Thr Thr Met Ile Thr Leu Met Asp Tyr Trp Gly Gln Gly Thr Thr Val
            100                 105                 110
```

```
Thr Val Ser Ser
        115

<210> SEQ ID NO 42
<211> LENGTH: 106
<212> TYPE: PRT
<213> ORGANISM: Artificial
<220> FEATURE:
<223> OTHER INFORMATION: Synthetic

<400> SEQUENCE: 42

Asp Val Gln Leu Asn Gln Ala Lys Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Pro Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Val Pro Trp
                85                  90                  95

Thr Phe Gly Gly Gly Thr Lys Leu Glu Ile
            100                 105

<210> SEQ ID NO 43
<211> LENGTH: 6
<212> TYPE: PRT
<213> ORGANISM: Artificial
<220> FEATURE:
<223> OTHER INFORMATION: Synthetic

<400> SEQUENCE: 43

Met Ala Arg Ser Gly Leu
1               5

<210> SEQ ID NO 44
<211> LENGTH: 6
<212> TYPE: PRT
<213> ORGANISM: Artificial
<220> FEATURE:
<223> OTHER INFORMATION: Synthetic

<400> SEQUENCE: 44

Met Ala Arg Ala Lys Glu
1               5

<210> SEQ ID NO 45
<211> LENGTH: 6
<212> TYPE: PRT
<213> ORGANISM: Artificial
<220> FEATURE:
<223> OTHER INFORMATION: Synthetic

<400> SEQUENCE: 45

Met Ser Arg Thr Met Ser
1               5

<210> SEQ ID NO 46
<211> LENGTH: 6
<212> TYPE: PRT
<213> ORGANISM: Artificial
```

```
<220> FEATURE:
<223> OTHER INFORMATION: Synthetic

<400> SEQUENCE: 46

Lys Cys Cys Tyr Ser Leu
1               5

<210> SEQ ID NO 47
<211> LENGTH: 8
<212> TYPE: PRT
<213> ORGANISM: Artificial
<220> FEATURE:
<223> OTHER INFORMATION: Synthetic

<400> SEQUENCE: 47

Trp Ile Phe Pro Trp Ile Gln Leu
1               5

<210> SEQ ID NO 48
<211> LENGTH: 12
<212> TYPE: PRT
<213> ORGANISM: Artificial
<220> FEATURE:
<223> OTHER INFORMATION: Synthetic

<400> SEQUENCE: 48

Trp Asp Leu Ala Trp Met Phe Arg Leu Pro Val Gly
1               5                   10

<210> SEQ ID NO 49
<211> LENGTH: 13
<212> TYPE: PRT
<213> ORGANISM: Artificial
<220> FEATURE:
<223> OTHER INFORMATION: Synthetic

<400> SEQUENCE: 49

Cys Thr Val Ala Leu Pro Gly Gly Tyr Val Arg Val Cys
1               5                   10

<210> SEQ ID NO 50
<211> LENGTH: 12
<212> TYPE: PRT
<213> ORGANISM: Artificial
<220> FEATURE:
<223> OTHER INFORMATION: Synthetic

<400> SEQUENCE: 50

Ile Pro Leu Val Val Pro Leu Gly Gly Ser Cys Lys
1               5                   10

<210> SEQ ID NO 51
<211> LENGTH: 7
<212> TYPE: PRT
<213> ORGANISM: Artificial
<220> FEATURE:
<223> OTHER INFORMATION: Synthetic

<400> SEQUENCE: 51

Lys Thr Leu Leu Pro Thr Pro
1               5

<210> SEQ ID NO 52
<211> LENGTH: 13
<212> TYPE: PRT
<213> ORGANISM: Artificial
<220> FEATURE:
```

```
<223> OTHER INFORMATION: Synthetic

<400> SEQUENCE: 52

Cys Val Ala Tyr Cys Ile Glu His His Cys Trp Thr Cys
1               5                   10

<210> SEQ ID NO 53
<211> LENGTH: 12
<212> TYPE: PRT
<213> ORGANISM: Artificial
<220> FEATURE:
<223> OTHER INFORMATION: Synthetic

<400> SEQUENCE: 53

Cys Val Phe Ala His Asn Tyr Asp Tyr Leu Val Cys
1               5                   10

<210> SEQ ID NO 54
<211> LENGTH: 10
<212> TYPE: PRT
<213> ORGANISM: Artificial
<220> FEATURE:
<223> OTHER INFORMATION: Synthetic

<400> SEQUENCE: 54

Cys Val Phe Thr Ser Asn Tyr Ala Phe Cys
1               5                   10

<210> SEQ ID NO 55
<211> LENGTH: 5
<212> TYPE: PRT
<213> ORGANISM: Artificial
<220> FEATURE:
<223> OTHER INFORMATION: Synthetic

<400> SEQUENCE: 55

Ser Gly Arg Ser Ala
1               5

<210> SEQ ID NO 56
<211> LENGTH: 4
<212> TYPE: PRT
<213> ORGANISM: Artificial
<220> FEATURE:
<223> OTHER INFORMATION: Synthetic

<400> SEQUENCE: 56

Trp Gly Phe Pro
1

<210> SEQ ID NO 57
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 57

Xaa Phe Xaa Xaa Tyr Leu Trp
1               5
```

```
<210> SEQ ID NO 58
<211> LENGTH: 17
<212> TYPE: PRT
<213> ORGANISM: Artificial
<220> FEATURE:
<223> OTHER INFORMATION: Synthetic

<400> SEQUENCE: 58

Ala Glu Pro Met Pro His Ser Leu Asn Phe Ser Gln Tyr Leu Trp Tyr
1               5                   10                  15

Thr

<210> SEQ ID NO 59
<211> LENGTH: 7
<212> TYPE: PRT
<213> ORGANISM: Artificial
<220> FEATURE:
<223> OTHER INFORMATION: Synthetic

<400> SEQUENCE: 59

Phe Ser Arg Tyr Leu Trp Ser
1               5

<210> SEQ ID NO 60
<211> LENGTH: 7
<212> TYPE: PRT
<213> ORGANISM: Artificial
<220> FEATURE:
<223> OTHER INFORMATION: Synthetic

<400> SEQUENCE: 60

Ile Glu Leu Leu Gln Ala Arg
1               5

<210> SEQ ID NO 61
<211> LENGTH: 12
<212> TYPE: PRT
<213> ORGANISM: Artificial
<220> FEATURE:
<223> OTHER INFORMATION: Synthetic

<400> SEQUENCE: 61

Asp Ile Thr Trp Asp Gln Leu Trp Asp Leu Met Lys
1               5                   10

<210> SEQ ID NO 62
<211> LENGTH: 16
<212> TYPE: PRT
<213> ORGANISM: Artificial
<220> FEATURE:
<223> OTHER INFORMATION: Synthetic

<400> SEQUENCE: 62

Ala Tyr Thr Lys Cys Ser Arg Gln Trp Arg Thr Cys Met Thr Thr His
1               5                   10                  15

<210> SEQ ID NO 63
<211> LENGTH: 15
<212> TYPE: PRT
<213> ORGANISM: Artificial
<220> FEATURE:
<223> OTHER INFORMATION: Synthetic

<400> SEQUENCE: 63

Pro Gln Asn Ser Lys Ile Pro Gly Pro Thr Phe Leu Asp Pro His
```

-continued

```
1               5               10              15

<210> SEQ ID NO 64
<211> LENGTH: 15
<212> TYPE: PRT
<213> ORGANISM: Artificial
<220> FEATURE:
<223> OTHER INFORMATION: Synthetic

<400> SEQUENCE: 64

Ser Met Glu Pro Ala Leu Pro Asp Trp Trp Trp Lys Met Phe Lys
1               5               10              15

<210> SEQ ID NO 65
<211> LENGTH: 13
<212> TYPE: PRT
<213> ORGANISM: Artificial
<220> FEATURE:
<223> OTHER INFORMATION: Synthetic

<400> SEQUENCE: 65

Ala Asn Thr Pro Cys Gly Pro Tyr Thr His Asp Cys Pro
1               5               10

<210> SEQ ID NO 66
<211> LENGTH: 7
<212> TYPE: PRT
<213> ORGANISM: Artificial
<220> FEATURE:
<223> OTHER INFORMATION: Synthetic

<400> SEQUENCE: 66

Phe Gln His Pro Ser Phe Ile
1               5

<210> SEQ ID NO 67
<211> LENGTH: 9
<212> TYPE: PRT
<213> ORGANISM: Artificial
<220> FEATURE:
<223> OTHER INFORMATION: Synthetic

<400> SEQUENCE: 67

Cys Val Pro Glu Leu Gly His Glu Cys
1               5

<210> SEQ ID NO 68
<211> LENGTH: 24
<212> TYPE: RNA
<213> ORGANISM: Artificial
<220> FEATURE:
<223> OTHER INFORMATION: Synthetic

<400> SEQUENCE: 68
aaccccuauc acgauuagca uuaa                                       24

<210> SEQ ID NO 69
<211> LENGTH: 24
<212> TYPE: RNA
<213> ORGANISM: Artificial
<220> FEATURE:
<223> OTHER INFORMATION: Synthetic

<400> SEQUENCE: 69
agucaacauc agucugauaa gcua                                       24
```

```
<210> SEQ ID NO 70
<211> LENGTH: 22
<212> TYPE: RNA
<213> ORGANISM: Artificial
<220> FEATURE:
<223> OTHER INFORMATION: Synthetic

<400> SEQUENCE: 70
acaguucuuc aacuggcagc uu                                          22

<210> SEQ ID NO 71
<211> LENGTH: 24
<212> TYPE: RNA
<213> ORGANISM: Artificial
<220> FEATURE:
<223> OTHER INFORMATION: Synthetic

<400> SEQUENCE: 71
aacaacaaaa ucacuagucu ucca                                        24

<210> SEQ ID NO 72
<211> LENGTH: 22
<212> TYPE: RNA
<213> ORGANISM: Artificial
<220> FEATURE:
<223> OTHER INFORMATION: Synthetic

<400> SEQUENCE: 72
acaggccggg acaagugcaa ua                                          22

<210> SEQ ID NO 73
<211> LENGTH: 22
<212> TYPE: RNA
<213> ORGANISM: Artificial
<220> FEATURE:
<223> OTHER INFORMATION: Synthetic

<400> SEQUENCE: 73
caaacaccau ugucacacuc ca                                          22

<210> SEQ ID NO 74
<211> LENGTH: 21
<212> TYPE: RNA
<213> ORGANISM: Artificial
<220> FEATURE:
<223> OTHER INFORMATION: Synthetic

<400> SEQUENCE: 74
ggcugucaau ucauagguca g                                           21

<210> SEQ ID NO 75
<211> LENGTH: 22
<212> TYPE: RNA
<213> ORGANISM: Artificial
<220> FEATURE:
<223> OTHER INFORMATION: Synthetic

<400> SEQUENCE: 75
ugggguauuu gacaaacuga ca                                          22

<210> SEQ ID NO 76
<211> LENGTH: 22
<212> TYPE: RNA
<213> ORGANISM: Artificial
<220> FEATURE:
<223> OTHER INFORMATION: Synthetic
```

```
<400> SEQUENCE: 76
agccuauccu ggauuacuug aa                                                22

<210> SEQ ID NO 77
<211> LENGTH: 21
<212> TYPE: RNA
<213> ORGANISM: Artificial
<220> FEATURE:
<223> OTHER INFORMATION: Synthetic

<400> SEQUENCE: 77
gcggaacuua gccacuguga a                                                 21

<210> SEQ ID NO 78
<211> LENGTH: 23
<212> TYPE: RNA
<213> ORGANISM: Artificial
<220> FEATURE:
<223> OTHER INFORMATION: Synthetic

<400> SEQUENCE: 78
acaaggauga aucuuuguua cug                                               23

<210> SEQ ID NO 79
<211> LENGTH: 1155
<212> TYPE: DNA
<213> ORGANISM: Artificial
<220> FEATURE:
<223> OTHER INFORMATION: Synthetic

<400> SEQUENCE: 79
atggcgttaa cccaacctag cagcgttagc gcgaatcctg gcgaaaccgt gaaaattacc      60
tgcagcggca gcagcggtag ctatggctgg tatcagcaga aaagcccgga ttcagcgcct     120
gtgaccgtga tttatcagag caaccagcgc ccgagcgata ttcctagccg ctttagcggc     180
agcaaaagcg gtagcaccgg caccttaacc attaccggtg tgcaggcgga agatgaagcg     240
gtgtattatt gcggcggttg gggttcaagc gttggcatgt ttggtgcggg taccacctta     300
accgtgttag gtcagagcag ccgttcaagc ggtggcggtg gtagcagcgg tggtggtggt     360
agcgcagtta ccctggatga aagcggtggc ggcttacaaa ctcctggtgg tgcgctgagc     420
ttagtttgta aagcgagcgg ctttaccttt agcagctatg cgatgggttg ggtgcgtcag     480
gcgcctggta aaggcttaga atgggtggcg ggcattagcg atgatggcga tagctatatt     540
agctatgcga ccgcggttaa aggtcgtgcg accattagcc gtgataacgg ccagagcacc     600
gttcgtctgc agctgaataa cctgcgcgcg gaagataccg cgacctatta ttgcgcgcgc     660
agccattgta gcggttgtcg taacgcggcg ctgattgatg catggggcca tggcaccgaa     720
gtgattgtga gcagcatgtc gtactaccat caccatcacc atcacgatta cgacatccca     780
acgaccgaaa acctgtattt tcagggcgcc atggttgata ccttatcagg tttatcaagt     840
gagcaaggtc agtccggtga tatgacaatt gaagaagata gtgctaccca tattaaattc     900
tcaaaacgtg atgaggacgg caaagagtta gctggtgcaa ctatggagtt gcgtgattca     960
tctggtaaaa ctattagtac atggatttca gatggacaag tgaaagattt ctacctgtat    1020
ccaggaaaat atacatttgt cgaaaccgca gcaccagacg gttatgaggt agcaactgct    1080 attacctttta cagttaatga gcaaggtcag gttactgtaa atggcaaagc aactaaaggt    1140
gacgctcata tttaa                                                     1155
```

-continued

```
<210> SEQ ID NO 80
<211> LENGTH: 2631
<212> TYPE: DNA
<213> ORGANISM: Bacteriophage P22

<400> SEQUENCE: 80
atgaatcata aacatcatca tcatcatcac agcagcggcg aaaacctgta ttttcagggc      60
catatgggat ccgccgacaa tgaaaacagg ctggagagca tcctgtcgcg ctttgatgcg     120
gactggacag ccagtgatga agccagacga gaggcaaaga atgatctctt cttctcccgc     180
gtatctcagt gggatgactg gctatcacaa tacacaaccc tgcagtatcg cgggcagttc     240
gatgttgtac gtccagtggt gcgcaagctc gtttctgaga tgcgtcagaa ccctattgat     300
gttctgtatc gtccaaagga cggagcaaga cctgatgccg ctgatgtgct tatgggtatg     360
tatcgcacag acatgcggca taacacggct aaaatcgcgg ttaacatcgc tgttcgtgag     420
cagattgaag ctggagttgg tgcgtggcgt ctggtcactg actacgaaga ccaaagtccg     480
acgagcaaca atcaggttat ccgtcgagag cctatccata gtgcctgctc ccatgttatc     540
tgggacagca acagcaaact gatggataag tctgacgccc gtcactgcac agttatccac     600
tcaatgagcc agaatggttg ggaggatttc gcagaaaaat acgacctcga tgcggatgat     660
attccatcat tccagaaccc caacgattgg gtatttccat ggctgacgca ggacacaatt     720
cagatcgctg agtttttacga agtggtcgag aagaaagaga cggcgtttat ctaccaagac     780
ccggttacgg gtgagccggt aagctacttt aagcgcgata ttaaagacgt catcgatgac     840
ctggctgata gtggatttat caaaattgca gagcgccaga ttaagcgtcg ccgggtatac     900
aaatcgatta tcacctgcac tgctgtactc aaagacaagc agctcattgc tggcgagcat     960
atccccattg ttccggtgtt cggagagtgg ggcttcgttg aagataaaga agtgtatgag    1020
ggtgtcgtcc gcctgacaaa agacggccag cgtctgcgca acatgattat gtcgttcaac    1080
gccgacatcg tggcccgcac tccgaagaag aagccgttct tctggcctga gcagattgca    1140
ggctttgagc atatgtacga cggtaacgac gattacccat actacctgct caatcgcact    1200
gacgaaaata gtggagacct tccgactcag ccgctggcat attatgaaaa cccggaagtg    1260
ccgcaagcca acgcctacat gctggaagca gcaaccagcg cagtaaaaga ggttgccact    1320
ctcggagttg atacagaagc ggtaaatggc ggacaggttg cgtttgatac cgtcaatcaa    1380
ctgaatatga gggctgacct tgagacatac gtgtttcagg ataatctggc taccgccatg    1440
cgccgtgacg gagagattta ccagtcgata gttaatgaca tctacgatgt tcctcgcaac    1500
gttacgatta cccttgagga tggcagcgag aaagatgttc agctaatggc tgaggttgtt    1560
gaccttgcta ctggagaaaa gcaggtacta acgatatca ggggggcgcta tgagtgctac    1620 acggatgttg gaccatcatt ccagtccatg aagcagcaaa accgcgcaga aattcttgag    1680
ttgctcggca gacgccaca gggaacgcca gaatatcaac tgctgttgct tcagtacttc    1740
accctgcttg atggtaaagg tgttgagatg atgcgtgact atgccaacaa gcagcttatt    1800
cagatgggcg ttaagaagcc agaaacgccc gaagagcagc aatggttagt agaggcgcaa    1860
caagccaaac aaggtggagg aggaggagga aagcttgcgt taacccaacc tagcagcgtt    1920
agcgcgaatc ctggcgaaac cgtgaaaatt acctgcagcg gcagcagcgg tagctatggc    1980
tggtatcagc agaaaagccc ggattcagcg cctgtgaccg tgatttatca gagcaaccag    2040
cgcccgagcg atattcctag ccgctttagc ggcagcaaaa gcggtagcac cggcaccta    2100 accattaccg gtgtgcaggc ggaagatgaa gcggtgtatt attgcggcgg ttggggttca    2160
```

-continued

```
agcgttggca tgtttggtgc gggtaccacc ttaaccgtgt taggtcagag cagccgttca      2220
agcggtggcg gtggtagcag cggtggtggt ggtagcgcag ttaccctgga tgaaagcggt      2280
ggcggcttac aaactcctgg tggtgcgctg agcttagttt gtaaagcgag cggctttacc      2340
tttagcagct atgcgatggg ttgggtgcgt caggcgcctg gtaaaggctt agaatgggtg      2400
gcgggcatta gcgatgatgg cgatagctat attagctatg cgaccgcggt taaaggtcgt      2460
gcgaccatta gccgtgataa cggccagagc accgttcgtc tgcagctgaa taacctgcgc      2520
gcggaagata ccgcgaccta ttattgcgcg cgcagccatt gtagcggttg tcgtaacgcg      2580
gcgctgattg atgcatgggg ccatggcacc gaagtgattg tgagcagcta a               2631

<210> SEQ ID NO 81
<211> LENGTH: 1905
<212> TYPE: DNA
<213> ORGANISM: Bacteriophage P22

<400> SEQUENCE: 81
atgaatcata aacatcatca tcatcatcac agcagcggcg aaaacctgta ttttcagggc        60
catatgggat ccgccgacaa tgaaaacagg ctggagagca tcctgtcgcg ctttgatgcg       120
gactggacag ccagtgatga agccagacga gaggcaaaga atgatctctt cttctcccgc       180
gtatctcagt gggatgactg gctatcacaa tacacaaccc tgcagtatcg cgggcagttc       240
gatgttgtac gtccagtggt gcgcaagctc gtttctgaga tgcgtcagaa ccctattgat       300
gttctgtatc gtccaaagga cggagcaaga cctgatgccg ctgatgtgct tatgggtatg       360
tatcgcacag acatgcggca taacacggct aaaatcgcgg ttaacatcgc tgttcgtgag       420
cagattgaag ctggagttgg tgcgtggcgt ctggtcactg actacgaaga ccaaagtccg       480
acgagcaaca atcaggttat ccgtcgagag cctatccata tgcctgctc ccatgttatc       540 tgggacagca acagcaaact gatggataag tctgacgccc gtcactgcac agttatccac       600
tcaatgagcc agaatggttg ggaggatttc gcagaaaaat acgacctcga tgcggatgat       660
attccatcat tccagaaccc caacgattgg gtatttccat ggctgacgca ggacacaatt       720
cagatcgctg agtttttacga agtggtcgag aagaaagaga cggcgtttat ctaccaagac      780
ccggttacgg gtgagccggt aagctacttt aagcgcgata ttaaagacgt catcgatgac       840
ctggctgata gtggatttat caaaattgca gagcgccaga ttaagcgtcg ccgggtatac       900
aaatcgatta tcacctgcac tgctgtactc aaagacaagc agctcattgc tggcgagcat       960
atccccattg ttccggtgtt cggagagtgg ggcttcgttg aagataaaga agtgtatgag      1020
ggtgtcgtcc gcctgacaaa agacggccag cgtctgcgca acatgattat gtcgttcaac      1080
gccgacatcg tggcccgcac tccgaagaag aagccgttct tctggcctga gcagattgca      1140
ggctttgagc atatgtacga cggtaacgac gattacccat actacctgct caatcgcact      1200
gacgaaaata gtggagacct tccgactcag ccgctggcat attatgaaaa cccggaagtg      1260
ccgcaagcca acgcctacat gctggaagca gcaaccagcg cagtaaaaga ggttgccact      1320
ctcggagttg atacagaagc ggtaaatggc ggacaggttg cgtttgatac cgtcaatcaa      1380
ctgaatatga gggctgacct tgagacatac gtgtttcagg ataatctggc taccgccatg      1440
cgccgtgacg gagagattta ccagtcgata gttaatgaca tctacgatgt tcctcgcaac      1500
gttacgatta cccttgagga tggcagcgag aaagatgttc agctaatggc tgaggttgtt      1560
gaccttgcta ctggagaaaa gcaggtacta acgatatca gggggcgcta tgagtgctac      1620
acggatgttg gaccatcatt ccagtccatg aagcagcaaa accgcgcaga aattcttgag     1680
```

-continued

```
ttgctcggca agacgccaca gggaacgcca gaatatcaac tgctgttgct tcagtacttc     1740
accctgcttg atggtaaagg tgttgagatg atgcgtgact atgccaacaa gcagcttatt     1800
cagatgggcg ttaagaagcc agaaacgccc gaagagcagc aatggttagt agaggcgcaa     1860
caagccaaac aaggtggtgg cgtacattcg cctaacaaga agtaa                     1905

<210> SEQ ID NO 82
<211> LENGTH: 2274
<212> TYPE: DNA
<213> ORGANISM: Bacteriophage P22

<400> SEQUENCE: 82
atgaatcata acatcatca tcatcatcac agcagcggcg aaaacctgta ttttcagggc       60
catatgggat ccgccgacaa tgaaaacagg ctggagagca tcctgtcgcg ctttgatgcg     120
gactggacag ccagtgatga agccagacga gaggcaaaga atgatctctt cttctcccgc     180
gtatctcagt gggatgactg gctatcacaa tacacaaccc tgcagtatcg cgggcagttc     240
gatgttgtac gtccagtggt gcgcaagctc gtttctgaga tgcgtcagaa ccctattgat     300
gttctgtatc gtccaaagga cggagcaaga cctgatgccg ctgatgtgct tatgggtatg     360
tatcgcacag acatgcggca taacacggct aaaatcgcgg ttaacatcgc tgttcgtgag     420
cagattgaag ctggagttgg tgcgtggcgt ctggtcactg actacgaaga ccaaagtccg     480
acgagcaaca atcaggttat ccgtcgagag cctatccata gtgcctgctc ccatgttatc     540
tgggacagca acagcaaact gatggataag tctgacgccc gtcactgcac agttatccac     600
tcaatgagcc agaatggttg ggaggatttc gcagaaaaat acgacctcga tgcggatgat     660
attccatcat tccagaaccc caacgattgg gtatttccat ggctgacgca ggacacaatt     720
cagatcgctg agttttacga agtggtcgag aagaaagaga cggcgtttat ctaccaagac     780
ccggttacgg gtgagccggt aagctacttt aagcgcgata ttaaagacgt catcgatgac     840
ctggctgata gtggatttat caaaattgca gagcgccaga ttaagcgtcg ccgggtatac     900
aaatcgatta tcacctgcac tgctgtactc aaagacaagc agctcattgc tggcgagcat     960
atccccattg ttccggtgtt cggagagtgg ggcttcgttg aagataaaga agtgtatgag    1020
ggtgtcgtcc gcctgacaaa agacggccag cgtctgcgca acatgattat gtcgttcaac    1080
gccgacatcg tggcccgcac tccgaagaag aagccgttct tctggcctga gcagattgca    1140
ggctttgagc atatgtacga cggtaacgac gattacccat actacctgct caatcgcact    1200
gacgaaaata gtggagacct tccgactcag ccgctggcat attatgaaaa cccggaagtg    1260
ccgcaagcca acgcctacat gctggaagca gcaaccagcg cagtaaaaga ggttgccact    1320
ctcggagtta atacagaagc ggtaaatggc ggacaggttg cgtttgatac cgtcaatcaa    1380
ctgaatatga gggctgacct tgagacatac gtgtttcagg ataatctggc taccgccatg    1440
cgccgtgacg agagagattta ccagtcgata gttaatgaca tctacgatgt tcctcgcaac    1500
gttacgatta cccttgagga tggcagcgag aaagatgttc agctaatggc tgaggttgtt    1560
gaccttgcta ctggagaaaa gcaggtacta aacgatatca ggggcgcta tgagtgctac    1620 acggatgttg gaccatcatt ccagtccatg aagcagcaaa accgcgcaga aattcttgag    1680
ttgctcggca agacgccaca gggaacgcca gaatatcaac tgctgttgct tcagtacttc    1740
accctgcttg atggtaaagg tgttgagatg atgcgtgact atgccaacaa gcagcttatt    1800
cagatgggcg ttaagaagcc agaaacgccc gaagagcagc aatggttagt agaggcgcaa    1860
```

```
caagccaaac aaggtcaaca agacccggca atggttcagg ctcagggcgt actcctgcag    1920
gggcaggctg aactggctaa agctcagaac cagacgctgt ccctgcaaat cgatgcagct    1980
aaagtcgaag cgcagaacca gcttaacgct gccagaatcg cagaaatctt caacaacatg    2040
gacctcagta aacaatctga gtttagagag ttccttaaaa ccgttgcttc attccagcag    2100
gaccgcagcg aagacgctcg cgcaaatgct gagttactcc ttaaaggcga tgaacagacg    2160
cacaagcagc gaatggacat tgccaacatc ctgcaatcgc agagacaaaa tcaaccttcc    2220
ggcagtgtag ccgagacacc tcaaggtggc gtacattcgc ctaacaagaa gtaa          2274
```

```
<210> SEQ ID NO 83
<211> LENGTH: 1026
<212> TYPE: DNA
<213> ORGANISM: Bacteriophage phi-29

<400> SEQUENCE: 83
atgaatcata aacatcatca tcatcatcac agcagcggcg aaaacctgta ttttcagggc      60
catatgattc tgacatacct gtctatcaat gtgatacagc ttcaaaaacg gaatagatgg     120
tttattcact atctgaacta ccttcaatct ctagcctatc agctatttga gtgggagaac     180
ctaccgccta cgataaaccc tagtttctta gaaaagtcta ttcatcaatt cgggtacgtg     240
gggttctata aagaccctgt catcagttat atcgcttgta atggcgctct atcgggtcag     300
agagacgttt acaaccaagc tacagttttt agagccgcat ctcctgtgta tcaaaaagaa     360
ttcaagctat acaactatag agatatgaag gaagaagata tgggtgttgt tatctacaac     420
aatgacatgc ctttccctac cacgccaacg ctagaattgt ttgcggctga attggctgaa     480
ttaaaagaaa tcatatcggt caaccaaaac gctcaaaaga cacccgtctt aattagagca     540
aatgacaata accaactgag cttaaaacaa gtgtataacc agtatgaagg taatgcccct     600
gttatcttcg ctcacgaagc tctcgacagt gactctatag aagtgtttaa gactgatgct     660
ccctatgtgg tggacaagtt aaacgctcag aaaaatgcag tatggaatga gatgatgact     720
ttccttggca ttaagaacgc taacctagag aagaaagagc gcatggttac ggatgaagtt     780
tccagtaacg atgaacagat cgagtctagc ggcactgtat ttttgaagtc gagggaagaa     840
gcatgtgaga agattaatga gctatatggt ctcaatgtta aagttaaatt cagatatgac     900
atcgtggaac aaatgagacg tgagctacag caaatagaaa atgtttcacg tggaacatcg     960
gacggtgaaa caaatgaggc gcatattgtg atggtggatg cgtataaacc gaccaaataa    1020
ctcgag                                                              1026
```

```
<210> SEQ ID NO 84
<211> LENGTH: 942
<212> TYPE: DNA
<213> ORGANISM: Bacteriophage phi-29

<400> SEQUENCE: 84
atgattctga catacctgtc tatcaatgtg atacagcttc aaaaacggaa tagatggttt      60
attcactatc tgaactacct tcaatctcta gcctatcagc tatttgagtg ggagaaccta     120
ccgcctacga taaaccctag tttcttagaa aagtctattc atcaattcgg gtacgtgggg     180
ttctataaag accctgtcat cagttatatc gcttgtaatg gcgctctatc gggtcagaga     240
gacgtttaca accaagctac agtttttaga gccgcatctc ctgtgtatca aaaagaattc     300
aagctataca actatagaga tatgaaggaa gaagatatgg gtgttgttat ctacaacaat     360
gacatggctt tccctaccac gccaacgcta gaattgtttg cggctgaatt ggctgaatta     420
```

-continued

```
aaagaaatca tatcggtcaa ccaaaacgct caaaagacac ccgtcttaat tagagcaaat        480
gacaataacc aactgagctt aaaacaagtg tataaccagt atgaaggtaa tgcccctgtt        540
atcttcgctc acgaagctct cgacagtgac tctatagaag tgtttaagac tgatgctccc        600
tatgtggtgg acaagttaaa cgctcagaaa aatgcagtat ggaatgagat gatgactttc        660
cttggcatta agaacgctaa cctagagaag aaagagcgca tggttacgga tgaagtttcc        720
agtaacgatg aacagatcga gtctagcggc actgtatttt tgaagtcgag ggaagaagca        780
tgtgagaaga ttaatgagct atatggtctc aatgttaaag ttaaattcag atatgacatc        840
gtggaacaaa tgagacgtga gctacagcaa atagaaaatg tttcacgtgg aacatcggac        900
ggtgaaacaa atgagctcga gcaccaccac caccaccact ga                          942
```

<210> SEQ ID NO 85
<211> LENGTH: 927
<212> TYPE: DNA
<213> ORGANISM: Bacteriophage phi-29

<400> SEQUENCE: 85

```
atggcacgta aacgcagtaa cacataccga tctatcaatg agatacagcg tcaaaaacgg         60
aatagatggt ttattcacta tctgaactac cttcaatctc tagcctatca gctatttgag        120
tgggagaacc taccgcctac gataaaccct agtttcttag aaaagtctat tcatcaattc        180
gggtacgtgg ggttctataa agaccctgtc atcagttata tcgcttgtaa tggcgctcta        240
tcgggtcaga gagacgttta caaccaagct acagtttta gagccgcatc tcctgtgtat         300
caaaaagaat tcaagctata caactataga gatatgaagg aagaagatat gggtgttgtt        360
atctacaaca atgacatggc tttccctacc acgccaacgc tagaattgtt tgcggctgaa        420
ttggctgaat taaaagaaat catatcggtc aaccaaaacg ctcaaaagac accgtctta         480 attagagcca atgacaataa ctgcctgagc ttaaaacaag tgtataacca gtatgaaggt        540
aatgcccctg ttatcttcgc tcacgaagct ctcgacagtg actctataga agtgtttaag        600
actgatgctc cctatgtggt ggacaagtta aacgctcaga aaaatgcagt atggaatgag        660
atgatgactt tccttggcat taagaacgct aacctagaga agaaagagcg catggttacg        720
gatgaagttt ccagtaacga tgaacagatc gagtctagcg gcactgtatt tttgaagtcg        780
agggaagaag catgtgagaa gattaatgag ctatatggtc tcaatgttaa agttaaattc        840
agatatgaca tcgtggaaca aatgagacgt gagctacagc aaatagaaaa tgtttcacgt        900
ggaacatcgg acggtgaaac aaatgag                                            927
```

<210> SEQ ID NO 86
<211> LENGTH: 927
<212> TYPE: DNA
<213> ORGANISM: Bacteriophage phi-29

<400> SEQUENCE: 86

```
atggcacgta aacgcagtaa cacataccga tctatcaatg agatacagcg tcaaaaacgg         60
aatagatggt ttattcacta tctgaactac cttcaatctc tagcctatca gctatttgag        120
tgggagaacc taccgcctac gataaaccct agtttcttag aaaagtctat tcatcaattc        180
gggtacgtgg ggttctataa agaccctgtc atcagttata tcgcttgtaa tggcgctcta        240
tcgggtcaga gagacgttta caaccaagct acagtttta gagccgcatc tcctgtgtat         300
caaaaagaat tcaagctata caactataga gatatgaagg aagaagatat gggtgttgtt        360
```

-continued

```
atctacaaca atgacatggc tttccctacc acgccaacgc tatgcttgtt tgcggctgaa       420
ttggctgaat taaaagaaat catatcggtc aaccaaaacg ctcaaaagac acccgtctta       480
attagagcca atgacaataa ccaactgagc ttaaaacaag tgtataacca gtatgaaggt       540
aatgcccctg ttatcttcgc tcacgaagct ctcgacagtg actctataga agtgtttaag       600
actgatgctc cctatgtggt ggacaagtta aacgctcaga aaaatgcagt atggaatgag       660
atgatgactt tccttggcat taagaacgct aacctagaga agaaagagcg catggttacg       720
gatgaagttt ccagtaacga tgaacagatc gagtctagcg gcactgtatt tttgaagtcg       780
agggaagaag catgtgagaa gattaatgag ctatatggtc tcaatgttaa agttaaattc       840
agatatgaca tcgtggaaca aatgagacgt gagctacagc aaatagaaaa tgtttcacgt       900
ggaacatcgg acggtgaaac aaatgag                                          927
```

<210> SEQ ID NO 87
<211> LENGTH: 927
<212> TYPE: DNA
<213> ORGANISM: Bacteriophage phi-29

<400> SEQUENCE: 87

```
atggcacgta aacgcagtaa cacataccga tctatcaatg agatacagcg tcaaaaacgg        60
aatagatggt ttattcacta tctgaactac cttcaatctc tagcctatca gctatttgag       120
tgggagaacc taccgcctac gataaaccct agtttcttag aaaagtctat tcatcaattc       180
gggtacgtgg ggttctataa agaccctgtc atcagttata tcgcttgtaa tggctgtcta       240
tcgggtcaga gagacgttta caaccaagct acagttttta gagccgcatc tcctgtgtat       300
caaaaagaat tcaagctata caactataga gatatgaagg aagaagatat gggtgttgtt       360
atctacaaca atgacatggc tttccctacc acgccaacgc tagaattgtt tgcggctgaa       420
ttggctgaat taaaagaaat catatcggtc aaccaaaacg ctcaaaagac acccgtctta       480
attagagcca atgacaataa ccaactgagc ttaaaacaag tgtataacca gtatgaaggt       540
aatgcccctg ttatcttcgc tcacgaagct ctcgacagtg actctataga agtgtttaag       600
actgatgctc cctatgtggt ggacaagtta aacgctcaga aaaatgcagt atggaatgag       660
atgatgactt tccttggcat taagaacgct aacctagaga agaaagagcg catggttacg       720
gatgaagttt ccagtaacga tgaacagatc gagtctagcg gcactgtatt tttgaagtcg       780
agggaagaag catgtgagaa gattaatgag ctatatggtc tcaatgttaa agttaaattc       840
agatatgaca tcgtggaaca aatgagacgt gagctacagc aaatagaaaa tgtttcacgt       900
ggaacatcgg acggtgaaac aaatgag                                          927
```

<210> SEQ ID NO 88
<211> LENGTH: 1575
<212> TYPE: DNA
<213> ORGANISM: Bacteriophage phi-29

<400> SEQUENCE: 88

```
atggcatatg taccattatc aggaacgaac gtcaggattt tagctgacgt tcctttctct        60
aatgattata aaaacacgag atggttcaca tcttcaagta atcagtataa ctggtttaac       120
agcaaatcac gtgtgtatga atgagtaaa gtaacattca tggggtttag agaaaataaa       180
ccatatgttt cggttagtct tcccatagat aagctttaca gtgcgtcata tattatgttt       240
caaaatgcag actacggtaa caagtggttt tatgcatttg taaccgagtt agaatttaaa       300
aatagtgctg ttacctacgt tcactttgaa attgatgttc tccaaacatg gatgttcgat       360
```

-continued

```
attaaatttc aagaatcatt cattgtgagg gagcacgtta aattatggaa tgacgacggg      420
acaccgacta tcaacacaat tgatgagggt ctcagctacg gaagtgaata cgacatagtt      480
tctgtagaaa accataaacc atacgacgac atgatgtttc tcgtgattat ttccaaaagc      540
attatgcatg ggacgccggg agaagaggaa agcaggctaa atgacataaa cgcaagcctg      600
aacggcatgc cgcaacctct ctgctactat attcacccat tctacaaaga tggtaaagtt      660
cctaaaacgt atatcggaga taacaacgct aacttgtctc ctattgtcaa tatgctcacc      720
aatatctttt cacagaagag cgctgttaac gatattgtca atatgtatgt gactgattat      780
attggtttga agcttgacta taaaaatggt gataaagaat tgaagctcga taaagacatg      840
tttgaacagg cgggtatagc tgacgataaa cacggtaacg ttgacaccat ctttgtgaag      900
aaaatacctg attatgaagc cctagaaata gacacaggtg ataaatgggg tggcttcaca      960
aaagaccaag aaagcaaact gatgatgtac ccttactgcg ttacggaaat aactgacttt     1020
aaaggcaacc atatgaatct gaaaaccgag tacatcaata acagtaaact atgtatacag     1080
gttaggggtt cactaggggt cagtaacaag gttgcctaca gtgttcagga ttataacgca     1140
gatagcgcat tgagtggcgg caatagattg actgcgtctc tagattcatc cttaatcaac     1200
aacaacccaa atgacatagc aatactaaat gactatctat ctgcttatca gttaacgaaa     1260
atgggcggca acacagcgtt tgattacggg aatgggtaca gaggtgtgta cgtcatcaaa     1320
aagcaattga aggctgaata cagacgaagt ctatcaagtt tcttccataa atacggatac     1380
aagattaaca gggtaaagaa accaaattta agaacacgaa aagcatttaa ctatgttcag     1440
acaaaagact gtttcatttc aggggacatc aataacaatg acttacagga aataagaaca     1500
attttcgata atggtattac tctttggcat actgacaaca tcggaaatta cagcgtcgag     1560
aatgaattga ggtga                                                       1575
```

<210> SEQ ID NO 89
<211> LENGTH: 1575
<212> TYPE: DNA
<213> ORGANISM: Bacteriophage phi-29

<400> SEQUENCE: 89

```
atggcatatg taccattatc aggaacgaac gtcaggattt tagctgacgt tcctttctct       60
aatgattata aaaacacgag atggttcaca tcttcaagta atcagtataa ctggtttaac      120
agcaaatcac gtgtgtatga aatgagtaaa gtaacattca tggggtttag agaaaataaa      180
ccatatgttt cggttagtct tcccatagat aagctttaca gtgcgtcata tattatgttt      240
caaaatgcag actacggtaa caagtggttt tatgcatttg taaccgagtt agaatttaaa      300
aatagtgctg ttacctacgt tcactttgaa attgatgttc tccaaacatg gatgttcgat      360
attaaatttc aagaatcatt cattgtgagg gagcacgtta ttttatggaa tctgctgggg      420
acaccgacta tcaacacaat tgatgagggt ctcagctacg gaagtgaata cgacatagtt      480
tctgtagaaa accataaacc atacgacgac atgatgtttc tcgtgattat ttccaaaagc      540
attatgcatg ggacgccggg agaagaggaa agcaggctaa atgacataaa cgcaagcctg      600
aacggcatgc cgcaacctct ctgctactat attcacccat tctacaaaga tggtaaagtt      660
cctaaaacgt atatcggaga taacaacgct aacttgtctc ctattgtcaa tatgctcacc      720
aatatctttt cacagaagag cgctgttaac gatattgtca atatgtatgt gactgattat      780
attggtttga agcttgacta taaaaatggt gataaagaat tgaagctcga taaagacatg      840
```

-continued

```
tttgaacagg cgggtatagc tgacgataaa cacggtaacg ttgacaccat ctttgtgaag        900
aaaatacctg attatgaagc cctagaaata gacacaggtg ataaatgggg tggcttcaca        960
aaagaccaag aaagcaaact gatgatgtac ccttactgcg ttacggaaat aactgacttt       1020
aaaggcaacc atatgaatct gaaaaccgag tacatcaata acagtaaact aaaagatacag      1080 gttaggggtt cactaggggt cagtaacaag gttgcctaca gtgttcagga ttataacgca       1140
gatagcgcat tgagtggcgg caatagattg actgcgtctc tagattcatc cttaatcaac       1200
aacaacccaa atgacatagc aatactaaat gactatctat ctgcttatca gttaacgaaa       1260
atgggcggca acacagcgtt tgattacggg aatgggtaca gaggtgtgta cgtcatcaaa       1320
aagcaattga aggctgaata cagacgaagt ctatcaagtt tcttccataa atacggatac       1380
aagattaaca gggtaaagaa accaaattta agaacacgaa aagcatttaa ctatgttcag       1440
acaaaagact gtttcatttc aggggacatc aataacaatg acttacagga aataagaaca       1500
attttcgata atggtattac tctttggcat actgacaaca tcggaaatta cagcgtcgag       1560
aatgaattga ggtga                                                        1575

<210> SEQ ID NO 90
<211> LENGTH: 1575
<212> TYPE: DNA
<213> ORGANISM: Bacteriophage phi-29

<400> SEQUENCE: 90
atggcatatg taccattatc aggaacgaac gtcaggattt tagctgacgt tcctttctct         60
aatgattata aaaacacgag atggttcaca tcttcaagta atcagtataa ctggtttaac        120
agcaaatcac gtgtgtatga aatgagtaaa gtaacattca tggggtttag agaaaataaa        180
ccatatgttt cggttagtct tcccatagat aagctttaca gtgcgtcata tattatgttt        240
caaaatgcag actacggtaa caagtggttt tatgcatttg taaccgagtt agaatttaaa        300
aatagtgctg ttacctacgt tcactttgaa attgatgttc tccaaacatg gatgttcgat        360
attaaatttc aagaatcatt cattgtgagg gagcacgtta ttttatggaa tctgctgggg        420
acaccgacta tcaacacaat tgatgagggt ctcagctacg gaagtgaata cctgatagtt        480
tctgtagtta accataaacc atacgacgac atgatgtttc tcgtgattat ttccaaaagc        540
attatgcatg ggacgccggg agaagaggaa agcaggctaa atgacataaa cgcaagcctg        600
aacggcatgc cgcaacctct ctgctactat attcacccat tctacaaaga tggtaaagtt        660
cctaaaacgt atatcggaga taacaacgct aacttgtctc ctattgtcaa tatgctcacc        720
aatatctttt cacagaagag cgctgttaac gatattgtca atatgtatgt gactgattat        780
attggtttga agcttgacta taaaaatggt gataaagaat tgaagctcga taaagacatg        840
tttgaacagg cgggtatagc tgacgataaa cacggtaacg ttgacaccat ctttgtgaag        900
aaaatacctg attatgaagc cctagaaata gacacaggtg ataaatgggg tggcttcaca        960
aaagaccaag aaagcaaact gatgatgtac ccttactgcg ttacggaaat aactgacttt       1020
aaaggcaacc atatgaatct gaaaaccgag tacatcaata acagtaaact aaaagatacag      1080 gttaggggtt cactaggggt cagtaacaag gttgcctaca gtgttcagga ttataacgca       1140
gatagcgcat tgagtggcgg caatagattg actgcgtctc tagattcatc cttaatcaac       1200
aacaacccaa atgacatagc aatactaaat gactatctat ctgcttatca gttaacgaaa       1260
atgggcggca acacagcgtt tgattacggg aatgggtaca gaggtgtgta cgtcatcaaa       1320
aagcaattga aggctgaata cagacgaagt ctatcaagtt tcttccataa atacggatac       1380
```

-continued

```
aagattaaca gggtaaagaa accaaattta agaacacgaa aagcatttaa ctatgttcag    1440
acaaaagact gtttcatttc aggggacatc aataacaatg acttacagga aataagaaca    1500
attttcgata atggtattac tctttggcat actgacaaca tcggaaatta cagcgtcgag    1560
aatgaattga ggtga                                                     1575

<210> SEQ ID NO 91
<211> LENGTH: 1575
<212> TYPE: DNA
<213> ORGANISM: Bacteriophage phi-29

<400> SEQUENCE: 91
atggcatatg taccattatc aggaacgaac gtcaggattt tagctgacgt tcctttctct      60
aatgattata aaaacacgag atggttcaca tcttcaagta atcagtataa ctggtttaac     120
agcaaatcac gtgtgtatga aatgagtaaa gtaacattca tggggtttag agaaaataaa     180
ccatatgttt cggttagtct tcccatagat aagctttaca gtgcgtcata tattatgttt     240
caaaatgcag actacggtaa caagtggttt tatgcatttg taaccgagtt agaatttaaa     300
aatagtgctg ttacctacgt tcactttgaa attgatgttc tccaaacatg gatgttcgat     360
attaaatttc aagaatcatt cattgtgagg gagcacgtta ttttatggaa tctgctgggg     420
acaccgacta tcaacacaat tgatgagggt ctcagctacg gaagtgaata cctgatagtt     480
tctgtagtta accataaacc atacgacgac atgatgtttc tcgtgattat ttccaaaagc     540
attatgcatg ggacgccggg agaagaggaa agcaggctaa atgacataaa cgcaagcctg     600
aacggcatgc cgcaacctct ctgctactat attcacccat tctacaaaga tggtaaagtt     660
cctaaaacgt atatcggaga taacaacgct aacttgtctc ctattgtcaa tatgctcacc     720
aatatctttt cacagaagag cgctgttaac gatattgtca atatgtatgt gactgattat     780
attggtttga agcttgacta taaaaatggt gataaagaat tgaagctcga taaagacatg     840
tttgaacagg cgggtatagc tgacgataaa cacggtaacg ttgacaccat ctttgtgaag     900
aaaatacctg attatgaagc cctagttata gttacaggtg ataaatgggg tggcttcaca     960
aaagaccaag aaagcaaact gatgatgtac ccttactgcg ttacggaaat aactgacttt    1020
aaaggcaacc atatgaatct gaaaaccgag tacatcaata acagtaaact aaagatacag    1080
gttaggggtt cactaggggt cagtaacaag gttgcctaca gtgttcagga ttataacgca    1140
gatagcgcat tgagtggcgg caatagattg actgcgtctc tagattcatc cttaatcaac    1200
aacaacccaa atgacatagc aatactaaat gactatctat ctgcttatca gttaacgaaa    1260
atgggcggca acacagcgtt tgattacggg aatgggtaca gaggtgtgta cgtcatcaaa    1320
aagcaattga ggctgaata cagacgaagt ctatcaagtt tcttccataa atacggatac    1380
aagattaaca gggtaaagaa accaaattta agaacacgaa aagcatttaa ctatgttcag    1440
acaaaagact gtttcatttc aggggacatc aataacaatg acttacagga aataagaaca    1500
attttcgata atggtattac tctttggcat actgacaaca tcggaaatta cagcgtcgag    1560
aatgaattga ggtga                                                     1575

<210> SEQ ID NO 92
<211> LENGTH: 1647
<212> TYPE: DNA
<213> ORGANISM: Bacteriophage phi-29

<400> SEQUENCE: 92
```

-continued

```
atgaatcata aacatcatca tcatcatcac agcagcggcg aaaacctgta ttttcagggc      60
catatgggat ccatggcata tgtaccatta tcaggaacga acgtcaggat tttagctgac     120
gttcctttct ctaatgatta taaaaacacg agatggttca catcttcaag taatcagtat     180
aactggttta acagcaaatc acgtgtgtat gaaatgagta aagtaacatt catggggttt     240
agagaaaata aaccatatgt ttcggttagt cttcccatag ataagcttta cagtgcgtca     300
tatattatgt ttcaaaatgc agactacggt aacaagtggt tttatgcatt tgtaaccgag     360
ttagaattta aaaatagtgc tgttacctac gttcactttg aaattgatgt tctccaaaca     420
tggatgttcg atattaaatt tcaagaatca ttcattgtga gggagcacgt taaattatgg     480
aatgacgacg ggacaccgac tatcaacaca attgatgagg gtctcagcta cggaagtgaa     540
tacgacatag tttctgtaga aaaccataaa ccatacgacg acatgatgtt tctcgtgatt     600
atttccaaaa gcattatgca tgggacgccg ggagaagagg aaagcaggct aaatgacata     660
aacgcaagcc tgaacggcat gccgcaacct ctctgctact atattcaccc attctacaaa     720
gatggtaaag ttcctaaaac gtatatcgga gataacaacg ctaacttgtc tcctattgtc     780
aatatgctca ccaatatctt ttcacagaag agcgctgtta acgatattgt caatatgtat     840
gtgactgatt atattggttt gaagcttgac tataaaaatg gtgataaaga attgaagctc     900
gataaagaca tgtttgaaca ggcgggtata gctgacgata acacggtaa cgttgacacc     960 atctttgtga agaaaatacc tgattatgaa gccctagaaa tagacacagg tgataaatgg    1020
ggtggcttca caaaagacca agaaagcaaa ctgatgatgt acccttactg cgttacggaa    1080
ataactgact ttaaaggcaa ccatatgaat ctgaaaaccg agtacatcaa taacagtaaa    1140
ctaaagatac aggttagggg ttcactaggg gtcagtaaca aggttgccta cagtgttcag    1200
gattataacg cagatagcgc attgagtggc ggcaatagat tgactgcgtc tctagattca    1260
tccttaatca acaacaaccc aaatgacata gcaatactaa atgactatct atctgcttat    1320
cagttaacga aaatgggcgg caacacagcg tttgattacg ggaatgggta cagaggtgtg    1380
tacgtcatca aaaagcaatt gaaggctgaa tacagacgaa gtctatcaag tttcttccat    1440
aaatacggat acaagattaa cagggtaaag aaaccaaatt taagaacacg aaaagcattt    1500
aactatgttc agacaaaaga ctgtttcatt tcaggggaca tcaataacaa tgacttacag    1560
gaaataagaa caattttcga taatggtatt actctttggc atactgacaa catcggaaat    1620
tacagcgtcg agaatgaatt gaggtga                                        1647
```

<210> SEQ ID NO 93
<211> LENGTH: 1800
<212> TYPE: DNA
<213> ORGANISM: Bacteriophage phi-29

<400> SEQUENCE: 93

```
atggcatatg taccattatc aggaacgaac gtcaggattt tagctgacgt tcctttctct      60
aatgattata aaaacacgag atggttcaca tcttcaagta atcagtataa ctggtttaac     120
agcaaatcac gtgtgtatga aatgagtaaa gtaacattca tggggtttag agaaaataaa     180
ccatatgttt cggttagtct tcccatagat aagctttaca gtgcgtcata tattatgttt     240
caaaatgcag actacggtaa caagtggttt tatgcatttg taaccgagtt agaatttaaa     300
aatagtgctg ttacctacgt tcactttgaa attgatgttc tccaaacatg gatgttcgat     360
attaaatttc aagaatcatt cattgtgagg gagcacgtta aattatggaa tgacgacggg     420
acaccgacta tcaacacaat tgatgagggt ctcagctacg gaagtgaata cgacatagtt     480
```

-continued

```
tctgtagaaa accataaacc atacgacgac atgatgtttc tcgtgattat ttccaaaagc      540
attatgcatg ggacgccggg agaagaggaa agcaggctaa atgacataaa cgcaagcctg      600
aacggcatgc cgcaacctct ctgctactat attcacccat tctacaaaga tggtaaagtt      660
cctaaaacgt atatcggaga taacaacgct aacttgtctc ctattgtcaa tatgctcacc      720
aatatctttt cacagaagag cgctgttaac gatattgtca atatgtatgt gactgattat      780
attggtttga agcttgacta taaaaatggt gataaagaat tgaagctcga taaagacatg      840
tttgaacagg cgggtatagc tgacgataaa cacggtaacg ttgacaccat ctttgtgaag      900
aaaatacctg attatgaagc cctagaaata gacacaggtg ataaatgggg tggcttcaca      960
aaagaccaag aaagcaaact gatgatgtac ccttactgcg ttacggaaat aactgacttt      1020
aaaggcaacc atatgaatct gaaaaccgag tacatcaata acagtaaact aaagatacag      1080
gttaggggtt cactaggggt cagtaacaag gttgcctaca gtgttcagga ttataacgca      1140
gatagcgcat tgagtggcgg caatagattg actgcgtctc tagattcatc cttaatcaac      1200
aacaacccaa atgacatagc aatactaaat gactatctat ctgcttattt acagggcaac      1260
aaaaattcac tagagaacca aaaatcgtct atccttttta atggcattat gggtatgatc      1320
ggcggaggta tatcagcggg agcaagtgcg gcaggaggtt cagccctagg gatggcttca      1380
tcagttacag ggatgacaag cactgcgggt aatgctgttc tacagatgca agcgatgcaa      1440
gccaagcaag ccgatatagc aaacattccg ccgcagttaa cgaaaatggg cggcaacaca      1500
gcgtttgatt acgggaatgg gtacagaggt gtgtacgtca tcaaaaagca attgaaggct      1560
gaatacagac gaagtctatc aagtttcttc cataaatacg gatacaagat taacagggta      1620
aagaaaccaa atttaagaac acgaaaagca tttaactatg ttcagacaaa agactgtttc      1680
atttcagggg acatcaataa caatgactta caggaaataa gaacaatttt cgataatggt      1740
attactcttt ggcatactga caacatcgga aattacagcg tcgagaatga attgaggtga      1800
```

NANOPORE ASSEMBLIES AND USES THEREOF

CROSS-REFERENCE TO RELATED APPLICATIONS

This application is a U.S. national phase application of International Application No. PCT/US2019/017432, filed on Feb. 11, 2019, which in turn claims priority under 35 U.S.C. § 119 (e) to U.S. Provisional Patent Application No. 62/629,604, filed on Feb. 12, 2018, the disclosures of which are incorporated herein by reference in their entireties.

FIELD OF THE INVENTION

The present disclosure relates generally to nanopores and more specifically to systems and methods using nanopores assembled with non-membrane proteins for detecting analytes.

BACKGROUND OF THE INVENTION

Biological nanopores are protein channels embedded in a substrate, typically lipid membranes. A wide variety of protein complexes in nature form elegant channel-like structures, some of which have been explored as nanopores, exemplified by α-hemolysin, MspA, aerolysin, FluA, Omp F/G, CsgG, ClyA, and PA₆₃. For example, the biological protein nanopore Δ-hemolysin (ΔHL) from *Staphylococcus aureus* has been used for single molecule detection.

Recently, researchers have adopted biological, solid-state, DNA origami, and hybrid nanopores in single-molecule analyses. Biological nanopores have advantages compared to their synthetic counterparts, mostly because they can be reproducibly fabricated and modified with an atomic level precision that cannot yet be matched by artificial nanopores. The existing use of biological nanopores, however, also has drawbacks. For example, they are not versatile in providing different shapes, sizes, and hydrophilic/hydrophobic properties in order to detect different analytes with high sensitivity and specificity.

Accordingly, there remains a strong need for a robust nanopore system amendable for detecting analytes with distinct properties.

SUMMARY OF THE INVENTION

This disclosure addresses this need in the art by providing a nanopore assembly for detecting an analyte. The nanopore assembly comprises a channel formed of a plurality of subunits. Each of the subunits comprises a non-membrane protein capable of forming a protein channel In some embodiments, each of the subunits comprises a polypeptide having a polypeptide sequence at least 75% identical to a polypeptide sequence selected from the group consisting of SEQ ID NOs: 1-35. In some embodiments, the polypeptide comprises a polypeptide sequence at least 75% identical to SEQ ID NOs: 4-12.

In some embodiments, the polypeptide may include at least one residue substituted with cysteine. In some embodiments, the polypeptide is derived from phi29 portal or tail protein. In some embodiments, phi29 tail protein may include one or more of E595C, K321C, and K358C substitutions. In some embodiments, the phi29 tail protein may include one or more of K134I, D138L, D139L, D158L, E163V, E309V, D311V, K321V, K356A, K358A, D377A, D381V, N388L, R5241, R539A, and E595V substitutions.

In one aspect, the nanopore assembly further comprises a probe for detecting an analyte. The probe is operably linked to at least one of the subunits. The probe can be one of chemicals, carbohydrates, aptamers, nucleic acids, peptide, protein, antibodies, and receptors. In some embodiments, the probe comprises a sequence at least 75% identical to a sequence selected from the group consisting of SEQ ID NOs: 36-79. In some embodiments, the probe is an anti-PSA antibody. The probe may be operably linked via covalent bonding to at least one of the subunits. The covalent bonding includes a disulfide linkage, an ester linkage, or a sulfhydryl linkage. In some embodiments, the probe is operably linked to a location in proximity to an entrance of the channel or a location at an interior side of the channel The analyte can be one of nucleic acids, amino acids, peptides, proteins, polymers, and chemical molecules. In some embodiments, the analyte is one of PSA, CEA, AFP, VCAM, MiR-155, MiR-22, MiR-7, MiR-92a, MiR-122, MiR-192, MiR-223, MiR-26a, MiR-27a, and MiR-802.

According to some embodiments of the nanopore assembly, the channel is embedded in a polymersome. In some embodiments, the channel is inserted in a membrane. The membrane may include a polymer membrane or a lipid membrane. The polymer membrane may include an alternating copolymer, a periodic copolymer, a block copolymer, a di-block copolymer, a tri-block copolymer, a terpolymer, or a combination thereof. In some embodiments, the polymer membrane comprises PMOXA-PDMS-PMOXA. In some embodiments, the nanopore assembly may further include cholesterol and/or porphyrin.

In another aspect, this disclosure also provides an apparatus for detecting an analyte. The apparatus includes the nanopore assembly described above and optionally a support for the nanopore assembly. The apparatus may further include an electrode, to which the nanopore assembly is tethered.

In another aspect, this disclosure further provides a kit that includes the nanopore assembly described above and optionally instructions for using the nanopore assembly.

In another aspect, the disclosure provides a method of detecting an analyte. The method includes: (1) contacting a sample containing an analyte with the nanopore assembly as described; (2) applying an electrical current across the channel of the nanopore assembly; (3) determining the electrical current passing through the channel at one or more time intervals; and (4) comparing the electrical current measured at one or more time intervals with a reference electrical current, wherein a change in electrical current relative to the reference electrical current indicates a presence of the analyte in the sample. The analyte may be any one of nucleic acids, amino acids, peptides, proteins, polymers, and chemical molecules. In some embodiments, the reference electrical current is measured with a sample that does not contain the analyte. In some embodiments, the nanopore assembly is placed on a support.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

FIGS. 1A and 1B are a schematic diagram showing different functional layers of a typical non-membrane protein (shown as a truncated cone structure) to be used as a polymer membrane-embedded nanopore. FIG. 1A shows the three distinct domains that are important for membrane anchoring. FIG. 1B shows the two areas that are particularly important for conjugation of functional modules for single molecule sensing.

FIG. 2 shows an example of mutagenesis in the membrane anchoring layer for direct membrane insertion, in which phi29 gp9ΔLoop tail protein is shown as an example. Structure of phi29 gp9ΔLoop tail protein channel before and after a series of hydrophobic mutations made on the middle layer (boxed) to increase its capability of direct membrane insertion. The exemplary mutation sites include: K134I, D138L, D139L, D158L, E163V, E309V, D311V, K321V, K356A, K358A, D377A, D381V, N388L, R524I, R539A, and E595V. After expression and purification, the mutant proteins were spontaneously inserted into polymer membranes. Representative positive charged residues (e.g., R and K) and representative negative charged residues (e.g., E, Q, D, and N) are indicated.

FIG. 17A shows an example of polyoxazoline based triblock copolymers for insertion of non-membrane proteins as nanopores, as demonstrated using $PMOXA_6$-$PDMS_6$s-$PMOXA_6$.

FIG. 17B shows the stability of the planar membrane over the course of 2 days. The membrane shows no signs of membrane leakage. Membrane: $PMOXA_6$-$PDMS_3$s-$PMOXA_6$.

FIGS. 17C and 17D show an example of inserting non-membrane protein pores using a fusion of polymersomes with planar polymer membranes, as demonstrated using phi29 gp9 tail protein (FIG. 17C) and P22 gp1 portal proteins (FIG. 17D). Planar membrane and polymersome composition in FIG. 17C: $PMOXA_{11}$-$PDMS_{65}$-$PMOXA_{11}$; Planar membrane and polymersome composition in FIG. 17D: $PMOXA_5$-$PDMS_{13}$-$PMOXA_5$;

DETAILED DESCRIPTION OF THE INVENTION

Figure 3:
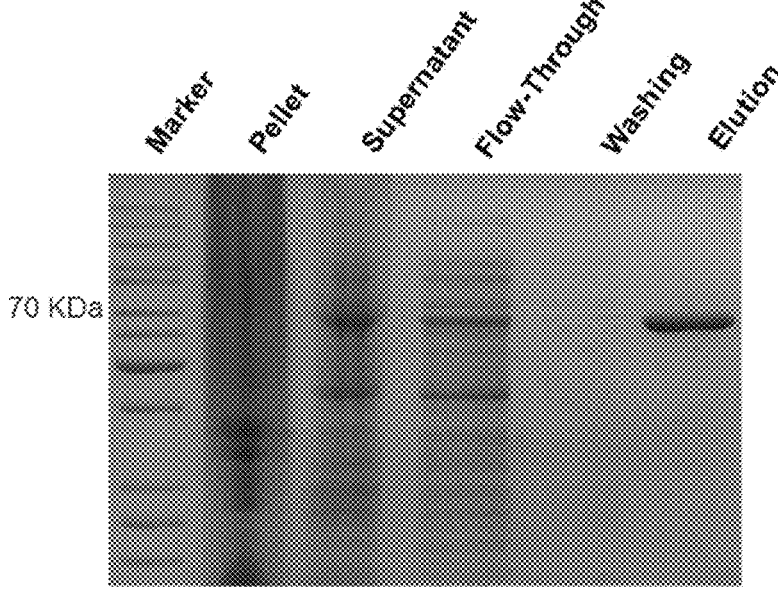
FIG. 3 shows an example of bacteriophage protein expression and purification, in which protein expression and purification of phi29 gp9 tail protein was demonstrated. Coomassie-blue stained SDS-PAGE gel shows the expression of phi29 gp-9 tail protein channel with a molecular weight of 70.33 kDa.

This disclosure provides a robust nanopore system and method adaptable for detecting different analytes. It allows for detection of a single molecule and of a target molecule present with other contaminants. The system offers a label-free, amplification-free, real-time detection. It requires very low sample amount and can be used for high-throughput analysis. The system can be adapted to detect a variety of analytes (e.g., small molecules, polymers, polypeptides, and nucleotides) with different shapes, sizes, and hydrophilic/hydrophobic properties, with high sensitivity and specificity.

This disclosure addresses the need in the art by providing nanopores formed of non-membrane proteins, such as proteins derived from bacteriophages. To generate the disclosed nanopores, bacteriophage proteins were expressed, purified, self-assembled, and inserted in lipid or polymer membranes. Non-membrane protein channels, however, are more difficult to be inserted into lipid bilayer or polymer membrane directly. Unlike membrane protein channels, non-membrane protein channels generally lack hydrophobic layer in the middle and hydrophilic layers in both ends. This invention overcomes this limitation by employing a series of methods for inserting various protein channels either directly or through highly efficient fusion mechanism in polymer membranes. In addition, in some scenarios, protein engineering, such as site-directed mutagenesis, insertion, and deletion of amino acids, and introduction of functional modules are carried out to tune nanopore properties to meet different detection needs.

The disclosed nanopore system has a wide variety of applications, including but not limited to single molecule detection, DNA/RNA/peptide sequencing, sensing of chemicals, biological reagents, and polymers, and disease diagnosis. As will be further described below, the methods, kits, and detection devices employing the disclosed nanopore system are also within the scope of this disclosure.

I. Nanopore Assemblies

One aspect of the present disclosure relates to nanopores formed of non-membrane proteins. The non-membrane proteins suitable for forming nanopores may be derived from cellular DNA translocases, helicases, terminase, ATPases, and fragments thereof. The non-membrane proteins suitable for forming nanopores may also include proteins involved in DNA repair, replication, recombination, chromosome segregation, DNA/RNA transportation, membrane sorting, cellular reorganization, cell division, bacterial binary fission, and other processes. The nanopore may include a plurality of subunits, each comprising a non-membrane protein. For example, the nanopore may include 10 to 15 subunits of phage portal proteins or 5 to 10 phage tail proteins. A non-membrane protein channel forming nanopores can be derived from bacteriophage portal proteins including, but not limited to T3, T4, T5, T7, SPP1, P22, P2, P3, Lambda, Mu, HK97 and C1. For example, a non-membrane protein channel forming nanopores can be derived from bacteriophage tail proteins including, but not limited to phi29, C1, *Neisseria meningitidis* serogroup B, T4, phiX174, lambda, SPP1, T5, Mu, F4-1, P2, Serratia phage KSP90, Enterobacteria phage T7M, Bacteriophage HK97.

Also within the scope of this disclosure are the variants and homologs with significant identity to bacteriophage proteins (e.g., bacteriophage portal or tail proteins) including, but not limited to T3, T4, T5, T7, SPP1, P22, P2, P3, Lambda, Mu, HK97, and C1. For example, such variants and homologs may have sequences with at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity over the sequences of the bacteriophage portal proteins described herein.

Biological pore mutagenesis can be used to optimize protein pores for assembly or use in a composition or method set forth herein. For example, protein engineering and mutagenesis techniques can be used to mutate biological pores and tailor their properties for specific applications. Accordingly, the nanopore assembly may include a channel formed of a plurality of subunits. Each of the subunits comprises a polypeptide having a polypeptide sequence having at least 75% identity to a polypeptide sequence selected from the group consisting of SEQ ID NOs: 1-35. In some embodiments, the polypeptide comprises a polypeptide sequence at least 75% identical to SEQ ID NOs: 4-12.

The subunits may include one or more substitutions, deletions or insertion to facilitate functionalization of nanopores or insertion in membranes. For example, the subunit may include at least one residue substituted with cysteine, such that a functional group can be linked to the subunit via a disulfide bond. For example, cysteine residues can be used for conjugating chemicals such as porphyrin to the nanopore. In some embodiments, the subunit may include phi29 gp9 protein having one or more of E595C, K321C, and K358C substitutions.

In addition, the subunit may include the phi29 gp9 protein having one or more of K134I, D138L, D139L, D158L, E163V, E309V, D311V, K321V, K356A, K358A, D377A, D381V, N388L, R524I, R539A, and E595V substitutions. Substitution of charged residues (e.g., K, R, D, E) with hydrophobic residues (e.g., A, V, L) increases the hydrophobicity of the protein locally and globally.

In some embodiments, the process of incorporating a protein channel in a membrane or a nanodisc can benefit from an affinity tag (e.g., polyhistidine affinity tags) on the protein and from the purification of the mixed nanopore population over an affinity column (e.g., a Ni column). Affinity tags and chemical conjugation techniques (e.g., modifications of cysteines set forth above) can be used to attach tethers to nanopores for use in a variety of methods, compositions or apparatus set forth herein. For example, the resulting tethers can be used to attract or attach a nanopore to a solid support or an electrode.

TABLE 1

| SEQ ID NO | Sequences | Other information |
|---|---|---|
| SEQ ID NO: 1 | MADNENRLESILSRFDADWTASDEARREAKNDLF FSRVSQWDDWLSQYTTLQYRGQFDVVRPVVRKL VSEMRQNPIDVLYRPKDGARPDAADVLMGMYRT DMRHNTAKIAVNIAVREQIEAGVGAWRLVTDYE DQSPTSNNQVIRREPIHSACSHVIWDSNSKLMDKS DARHCTVIHSMSQNGWEDFAEKYDLDADDIPSFQ NPNDWVFPWLTQDTIQIAEFYEVVEKKETAFIYQ DPVTGEPVSYFKRDIKDVIDDLADSGFIKIAERQIK RRRVYKSIITCTAVLKDKQLIAGEHIPIVPVFGEWG FVEDKEVYEGVVRLTKDGQRLRNMIMSFNADIV ARTPKKKPFFWPEQIAGFEHMYDGNDDYPYYLL NRTDENSGDLPTQPLAYYENPEVPQANAYMLEA ATSAVKEVATLGVDTEAVNGGQVAFDTVNQLN MRADLETYVFQDNLATAMRRDGEIYQSIVNDIYD VPRNVTITLEDGSEKDVQLMAEVVDLATGEKQVL NDIRGRYECYTDVGPSFQSMKQQNRAEILELLGK TPQGTPEYQLLLLQYFTLLDGKGVEMMRDYANK QLIQMGVKKPETPEEQQWLVEAQQAKQGQQDPA MVQAQGVLLQGQAELAKAQNQTLSLQIDAAKVE AQNQLNAARIAEIFNNMDLSKQSEFREFLKTVASF QQDRSEDARANAELLLKGDEQTHKQRMDIANILQ SQRQNQPSGSVAETPQ | P22 portal protein channel/nanopore/ WT |
| SEQ ID NO: 2 | MADNENRLESILSRFDADWTASDEARREAKNDLF FSRVSQWDDWLSQYTTLQYRGQFDVVRPVVRKL VSEMRQNPIDVLYRPKDGARPDAADVLMGMYRT DMRHNTAKIAVNIAVREQIEAGVGAWRLVTDYE DQSPTSNNQVIRREPIHSACSHVIWDSNSKLMDKS DARHCTVIHSMSQNGWEDFAEKYDLDADDIPSFQ NPNDWVFPWLTQDTIQIAEFYEVVEKKETAFIYQ DPVTGEPVSYFKRDIKDVIDDLADSGFIKIAERQIK RRRVYKSIITCTAVLKDKQLIAGEHIPIVPVFGEWG FVEDKEVYEGVVRLTKDGQRLRNMIMSFNADIV ARTPKKKPFFWPEQIAGFEHMYDGNDDYPYYLL NRTDENSGDLPTQPLAYYENPEVPQANAYMLEA ATSAVKEVATLGVDTEAVNGGQVAFDTVNQLN MRADLETYVFQDNLATAMRRDGEIYQSIVNDIYD VPRNVTITLEDGSEKDVQLMAEVVDLATGEKQVL NDIRGRYECYTDVGPSFQSMKQQNRAEILELLGK TPQGTPEYQLLLLQYFTLLDGKGVEMMRDYANK QLIQMGVKKPETPEEQQWLVEAQQAKQ | P22 portal protein channel/nanopore/ Barrel deletion |
| SEQ ID NO: 3 | MAYVPLSGTNVRILADVPFSNDYKNTRWFTSSSN QYNWFNSKSRVYEMSKVTFMGFRENKPYVSVSL PIDKLYSASYIMFQNADYGNKWFYAFVTELEFKN SAVTYVHFEIDVLQTWMFDIKFQESFIVREHVKL WNDDGTPTINTIDEGLSYGSEYDIVSVENHKPYDD MMFLVIISKSIMHGTPGEEESRLNDINASLNGMPQ PLCYYIHPFYKDGKVPKTYIGDNNANLSPIVNMLT NIFSQKSAVNDIVNMYVTDYIGLKLDYKNGDKEL KLDKDMFEQAGIADDKHGNVDTIFVKKIPDYEAL EIDTGDKWGGFTKDQESKLMMYPYCVTEITDFKG NHMNLKTEYINNSKLKIQVRGSLGVSNKVAYSVQ DYNADSALSGGNRLTASLDSSLINNNPNDIAILND YLSAYLQGNKNSLENQKSSILFNGIMGMIGGGISA GASAAGGSALGMASSVTGMTSTAGNAVLQMQA MQAKQADIANIPPQLTKMGGNTAFDYGNGYRGV YVIKKQLKAEYRRSLSSFFHKYGYKINRVKKPNL RTRKAFNYVQTKDCFISGDINNNDLQEIRTIFDNGI TLWHTDNIGNYSVENELR | Phi29 tail protein channel/nanopore/ WT |
| SEQ ID NO: 4 | MAYVPLSGTNVRILADVPFSNDYKNTRWFTSSSN QYNWFNSKSRVYEMSKVTFMGFRENKPYVSVSL PIDKLYSASYIMFQNADYGNKWFYAFVTELEFKN SAVTYVHFEIDVLQTWMFDIKFQESFIVREHVKL WNDDGTPTINTIDEGLSYGSEYDIVSVENHKPYDD MMFLVIISKSIMHGTPGEEESRLNDINASLNGMPQ PLCYYIHPFYKDGKVPKTYIGDNNANLSPIVNMLT NIFSQKSAVNDIVNMYVTDYIGLKLDYKNGDKEL KLDKDMFEQAGIADDKHGNVDTIFVKKIPDYEAL EIDTGDKWGGFTKDQESKLMMYPYCVTEITDFKG NHMNLKTEYINNSKLKIQVRGSLGVSNKVAYSVQ DYNADSALSGGNRLTASLDSSLINNNPNDIAILND YLSAYQLTKMGGNTAFDYGNGYRGVYVIKKQLK AEYRRSLSSFFHKYGYKINRVKKPNLRTRKAFNY VQTKDCFISGDINNNDLQEIRTIFDNGITLWHTDNI | Phi29 tail protein channel/nanopore/ phi29-gp9 Δ417- 491 |

TABLE 1-continued

| Amino Acid Sequences of Channel Proteins | | |
| --- | --- | --- |
| SEQ ID NO | Sequences | Other information |
| | GNYSVENELR | |
| SEQ ID NO: 5 | MAYVPLSGTNVRILADVPFSNDYKNTRWFTSSSN QYNWFNSKSRVYEMSKVTFMGFRENKPYVSVSL PIDKLYSASYIMFQNADYGNKWFYAFVTELEFKN SAVTYVHFEIDVLQTWMFDIKFQESFIVREHVKL WNDDGTPTINTIDEGLSYGSEYDIVSVENHKPYDD MMFLVIISKSIMHGTPGEEESRLNDINASLNGMPQ PLCYYIHPFYKDGKVPKTYIGDNNANLSPIVNMLT NIFSQKSAVNDIVNMYVTDYIGLKLDYKNGDKEL KLDKDMFEQAGIADDKHGNVDTIFVKKIPDYEAL EIDTGDKWGGFTKDQESKLMMYPYCVTEITDFKG NHMNLKTEYINNSKLCIQVRGSLGVSNKVAYSVQ DYNADSALSGGNRLTASLDSSLINNNPNDIAILND YLSAYQLTKMGGNTAFDYGNGYRGVYVIKKQLK AEYRRSLSSFFHKYGYKINRVKKPNLRTRKAFNY VQTKDCFISGDINNNDLQEIRTIFDNGITLWHTDNI GNYSVENELR | Phi29 tail protein channel/nanopore/ phi29-gp9Δ417- 491-K358C |
| SEQ ID NO: 6 | MAYVPLSGTNVRILADVPFSNDYKNTRWFTSSSN QYNWFNSKSRVYEMSKVTFMGFRENKPYVSVSL PIDKLYSASYIMFQNADYGNKWFYAFVTELEFKN SAVTYVHFEIDVLQTWMFDIKFQESFIVREHVILW NLLGTPTINTIDEGLSYGSEYDIVSVENHKPYDDM MFLVIISKSIMHGTPGEEESRLNDINASLNGMPQPL CYYIHPFYKDGKVPKTYIGDNNANLSPIVNMLTNI FSQKSAVNDIVNMYVTDYIGLKLDYKNGDKELK LDKDMFEQAGIADDKHGNVDTIFVKKIPDYEALEI DTGDKWGGFTKDQESKLMMYPYCVTEITDFKGN HMNLKTEYINNSKLKIQVRGSLGVSNKVAYSVQD YNADSALSGGNRLTASLDSSLINNNPNDIAILNDY LSAYQLTKMGGNTAFDYGNGYRGVYVIKKQLKA EYRRSLSSFFHKYGYKINRVKKPNLRTRKAFNYV QTKDCFISGDINNNDLQEIRTIFDNGITLWHTDNIG NYSVENELR | Phi29 tail protein channel/nanopore/ phi29-gp9Δ417- 491- K134I, D138L, D139L |
| SEQ ID NO: 7 | MAYVPLSGTNVRILADVPFSNDYKNTRWFTSSSN QYNWFNSKSRVYEMSKVTFMGFRENKPYVSVSL PIDKLYSASYIMFQNADYGNKWFYAFVTELEFKN SAVTYVHFEIDVLQTWMFDIKFQESFIVREHVILW NLLGTPTINTIDEGLSYGSEYLIVSVVNHKPYDDM MFLVIISKSIMHGTPGEEESRLNDINASLNGMPQPL CYYIHPFYKDGKVPKTYIGDNNANLSPIVNMLTNI FSQKSAVNDIVNMYVTDYIGLKLDYKNGDKELK LDKDMFEQAGIADDKHGNVDTIFVKKIPDYEALEI DTGDKWGGFTKDQESKLMMYPYCVTEITDFKGN HMNLKTEYINNSKLKIQVRGSLGVSNKVAYSVQD YNADSALSGGNRLTASLDSSLINNNPNDIAILNDY LSAYQLTKMGGNTAFDYGNGYRGVYVIKKQLKA EYRRSLSSFFHKYGYKINRVKKPNLRTRKAFNYV QTKDCFISGDINNNDLQEIRTIFDNGITLWHTDNIG NYSVENELR | Phi29 tail protein channel/nanopore/ phi29-gp9Δ417- 491- K134I, D138L, D139L, D158L, E163V |
| SEQ ID NO: 8 | MAYVPLSGTNVRILADVPFSNDYKNTRWFTSSSN QYNWFNSKSRVYEMSKVTFMGFRENKPYVSVSL PIDKLYSASYIMFQNADYGNKWFYAFVTELEFKN SAVTYVHFEIDVLQTWMFDIKFQESFIVREHVILW NLLGTPTINTIDEGLSYGSEYLIVSVVNHKPYDDM MFLVIISKSIMHGTPGEEESRLNDINASLNGMPQPL CYYIHPFYKDGKVPKTYIGDNNANLSPIVNMLTNI FSQKSAVNDIVNMYVTDYIGLKLDYKNGDKELK LDKDMFEQAGIADDKHGNVDTIFVKKIPDYEALV IVTGDKWGGFTKDQESKLMMYPYCVTEITDFKG NHMNLKTEYINNSKLKIQVRGSLGVSNKVAYSVQ DYNADSALSGGNRLTASLDSSLINNNPNDIAILND YLSAYQLTKMGGNTAFDYGNGYRGVYVIKKQLK AEYRRSLSSFFHKYGYKINRVKKPNLRTRKAFNY VQTKDCFISGDINNNDLQEIRTIFDNGITLWHTDNI GNYSVENELR | Phi29 tail protein channel/nanopore/ phi29-gp9Δ417- 491- K134I, D138L, D139L, D158L, E163V, E309V, D311V, K321V |
| SEQ ID NO: 9 | MAYVPLSGTNVRILADVPFSNDYKNTRWFTSSSN QYNWFNSKSRVYEMSKVTFMGFRENKPYVSVSL PIDKLYSASYIMFQNADYGNKWFYAFVTELEFKN SAVTYVHFEIDVLQTWMFDIKFQESFIVREHVKL WNDDGTPTINTIDEGLSYGSEYDIVSVENHKPYDD MMFLVIISKSIMHGTPGEEESRLNDINASLNGMPQ | Phi29 tail protein channel/nanopore/ phi29-gp9Δ417- 491-K356A, 358A |

TABLE 1-continued

Amino Acid Sequences of Channel Proteins

| SEQ ID NO | Sequences | Other information |
|---|---|---|
| | PLCYYIHPFYKDGKVPKTYIGDNNANLSPIVNMLT<br>NIFSQKSAVNDIVNMYVTDYIGLKLDYKNGDKEL<br>KLDKDMFEQAGIADDKHGNVDTIFVKKIPDYEAL<br>EIDTGDKWGGFTKDQESKLMMYPYCVTEITDFKG<br>NHMNLKTEYINNSALAIQVRGSLGVSNKVAYSVQ<br>DYNADSALSGGNRLTASLDSSLINNNPNDIAILND<br>YLSAYQLTKMGGNTAFDYGNGYRGVYVIKKQLK<br>AEYRRSLSSFFHKYGYKINRVKKPNLRTRKAFNY<br>VQTKDCFISGDINNNDLQEIRTIFDNGITLWHTDNI<br>GNYSVENELR | |
| SEQ ID NO: 10 | MAYVPLSGTNVRILADVPFSNDYKNTRWFTSSSN<br>QYNWFNSKSRVYEMSKVTFMGFRENKPYVSVSL<br>PIDKLYSASYIMFQNADYGNKWFYAFVTELEFKN<br>SAVTYVHFEIDVLQTWMFDIKFQESFIVREHVKL<br>WNDDGTPTINTIDEGLSYGSEYDIVSVENHKPYDD<br>MMFLVIISKSIMHGTPGEEESRLNDINASLNGMPQ<br>PLCYYIHPFYKDGKVPKTYIGDNNANLSPIVNMLT<br>NIFSQKSAVNDIVNMYVTDYIGLKLDYKNGDKEL<br>KLDKDMFEQAGIADDKHGNVDTIFVKKIPDYEAL<br>EIDTGDKWGGFTKDQESKLMMYPYCVTEITDFKG<br>NHMNLKTEYINNSALAIQVRGSLGVSNKVAYSVQ<br>AYNAVSALSGGLRLTASLDSSLINNNPNDIAILND<br>YLSAYQLTKMGGNTAFDYGNGYRGVYVIKKQLK<br>AEYRRSLSSFFHKYGYKINRVKKPNLRTRKAFNY<br>VQTKDCFISGDINNNDLQEIRTIFDNGITLWHTDNI<br>GNYSVENELR | Phi29 tail protein<br>channel/nanopore/<br>phi29-gp9Δ417-<br>491-<br>K356A, 358A,<br>D377A, D381V,<br>N388L |
| SEQ ID NO: 11 | MAYVPLSGTNVRILADVPFSNDYKNTRWFTSSSN<br>QYNWFNSKSRVYEMSKVTFMGFRENKPYVSVSL<br>PIDKLYSASYIMFQNADYGNKWFYAFVTELEFKN<br>SAVTYVHFEIDVLQTWMFDIKFQESFIVREHVKL<br>WNDDGTPTINTIDEGLSYGSEYDIVSVENHKPYDD<br>MMFLVIISKSIMHGTPGEEESRLNDINASLNGMPQ<br>PLCYYIHPFYKDGKVPKTYIGDNNANLSPIVNMLT<br>NIFSQKSAVNDIVNMYVTDYIGLKLDYKNGDKEL<br>KLDKDMFEQAGIADDKHGNVDTIFVKKIPDYEAL<br>EIDTGDKWGGFTKDQESKLMMYPYCVTEITDFKG<br>NHMNLKTEYINNSALAIQVRGSLGVSNKVAYSVQ<br>AYNAVSALSGGLRLTASLDSSLINNNPNDIAILND<br>YLSAYQLTKMGGNTAFDYGNGYRGVYVIKKQLK<br>AEYRRSLSSFFHKYGYKINRVKKPNLRTRKAFNY<br>VQTKDCFISGDINNNDLQEIRTIFDNGITLWHTDNI<br>GNYSVENELI | Phi29 tail protein<br>channel/nanopore/<br>phi29-gp9Δ417-<br>491-<br>K356A, 358A,<br>D377A, D381V,<br>N388L, R524I |
| SEQ ID NO: 12 | MNHKHHHHHHSSGENLYFQGHMGSMAYVPLSG<br>TNVRILADVPFSNDYKNTRWFTSSSNQYNWFNSK<br>SRVYEMSKVTFMGFRENKPYVSVSLPIDKLYSAS<br>YIMFQNADYGNKWFYAFVTELEFKNSAVTYVHF<br>EIDVLQTWMFDIKFQESFIVREHVKLWNDDGTPTI<br>NTIDEGLSYGSEYDIVSVENHKPYDDMMFLVIISK<br>SIMHGTPGEEESRLNDINASLNGMPQPLCYYIHPF<br>YKDGKVPKTYIGDNNANLSPIVNMLTNIFSQKSA<br>VNDIVNMYVTDYIGLKLDYKNGDKELKLDKDMF<br>EQAGIADDKHGNVDTIFVKKIPDYEALEIDTGDK<br>WGGFTKDQESKLMMYPYCVTEITDFKGNHMNLK<br>TEYINNSKLKIQVRGSLGVSNKVAYSVQDYNADS<br>ALSGGNRLTASLDSSLINNNPNDIAILNDYLSAYQ<br>LTKMGGNTAFDYGNGYRGVYVIKKQLKAEYRRS<br>LSSFFHKYGYKINRVKKPNLRTRKAFNYVQTKDC<br>FISGDINNNDLQEIRTIFDNGITLWHTDNIGNYSVE<br>NELR | Phi29 tail protein<br>channel/nanopore/<br>phi29-gp9Δ417-<br>491-N-his |
| SEQ ID NO: 13 | MAYVPLSGTNVRILADVPFSNDYKNTRWFTSSSN<br>QYNWFNSKSRVYEMSKVTFMGFRENKPYVSVSL<br>PIDKLYSASYIMFQNADYGNKWFYAFVTELEFKN<br>SAVTYVHFEIDVLQTWMFDIKFQESFIVREHVKL<br>WNDDGTPTINTIDEGLSYGSEYDIVSVENHKPYDD<br>MMFLVIISKSIMHGTPGEEESRLNDINASLNGMPQ<br>PLCYYIHPFYKDGKVPKTYIGDNNANLSPIVNMLT<br>NIFSQKSAVNDIVNMYVTDYIGLKLDYKNGDKEL<br>KLDKDMFEQAGIADDKHGNVDTIFVKKIPDYEAL<br>EIDTGDKWGGFTCDQESKLMMYPYCVTEITDFKG<br>NHMNLKTEYINNSKLKIQVRGSLGVSNKVAYSVQ<br>DYNADSALSGGNRLTASLDSSLINNNPNDIAILND<br>YLSAYLQGNKNSLENQKSSILFNGIMGMIGGGISA | Phi29 tail protein<br>channel/nanopore/<br>phi29-gp9<br>K321C |

TABLE 1-continued

| SEQ ID NO | Sequences | Other information |
|---|---|---|
| | GASAAGGSALGMASSVTGMTSTAGNAVLQMQA<br>MQAKQADIANIPPQLTKMGGNTAFDYGNGYRGV<br>YVIKKQLKAEYRRSLSSFFHKYGYKINRVKKPNL<br>RTRKAFNYVQTKDCFISGDINNNDLQEIRTIFDNGI<br>TLWHTDNIGNYSVENELR | |
| SEQ ID NO: 14 | MAYVPLSGTNVRILADVPFSNDYKNTRWFTSSSN<br>QYNWFNSKSRVYEMSKVTFMGFRENKPYVSVSL<br>PIDKLYSASYIMFQNADYGNKWFYAFVTELEFKN<br>SAVTYVHFEIDVLQTWMFDIKFQESFIVREHVKL<br>WNDDGTPTINTIDEGLSYGSEYDIVSVENHKPYDD<br>MMFLVIISKSIMHGTPGEEESRLNDINASLNGMPQ<br>PLCYYIHPFYKDGKVPKTYIGDNNANLSPIVNMLT<br>NIFSQKSAVNDIVNMYVTDYIGLKLDYKNGDKEL<br>KLDKDMFEQAGIADDKHGNVDTIFVKKIPDYEAL<br>EIDTGDKWGGFTKDQESKLMMYPYCVTEITDFKG<br>NHMNLKTEYINNSKLCIQVRGSLGVSNKVAYSVQ<br>DYNADSALSGGNRLTASLDSSLINNNPNDIAILND<br>YLSAYLQGNKNSLENQKSSILFNGIMGMIGGGISA<br>GASAAGGSALGMASSVTGMTSTAGNAVLQMQA<br>MQAKQADIANIPPQLTKMGGNTAFDYGNGYRGV<br>YVIKKQLKAEYRRSLSSFFHKYGYKINRVKKPNL<br>RTRKAFNYVQTKDCFISGDINNNDLQEIRTIFDNGI<br>TLWHTDNIGNYSVENELR | Phi29 tail protein<br>channel/nanopore/<br>phi29-gp9<br>K358C |
| SEQ ID NO: 15 | MAYVPLSGTNVRILADVPFSNDYKNTRWFTSSSN<br>QYNWFNSKSRVYEMSKVTFMGFRENKPYVSVSL<br>PIDKLYSASYIMFQNADYGNKWFYAFVTELEFKN<br>SAVTYVHFEIDVLQTWMFDIKFQESFIVREHVKL<br>WNDDGTPTINTIDEGLSYGSEYDIVSVENHKPYDD<br>MMFLVIISKSIMHGTPGEEESRLNDINASLNGMPQ<br>PLCYYIHPFYKDGKVPKTYIGDNNANLSPIVNMLT<br>NIFSQKSAVNDIVNMYVTDYIGLKLDYKNGDKEL<br>KLDKDMFEQAGIADDKHGNVDTIFVKKIPDYEAL<br>EIDTGDKWGGFTKDQESKLMMYPYCVTEITDFKG<br>NHMNLKTEYINNSKLKIQVRGSLGVSNKVAYSVQ<br>DYNADSALSGGNRLTASLDSSLINNNPNDIAILND<br>YLSAYLQGNKNSLENQKSSILFNGIMGMIGGGISA<br>GASAAGGSALGMASSVTGMTSTAGNAVLQMQA<br>MQAKQADIANIPPQLTKMGGNTAFDYGNGYRGV<br>YVIKKQLKAEYRRSLSSFFHKYGYKINRVKKPNL<br>RTRKAFNYVQTKDCFISGDINNNDLQEIRTIFDNGI<br>TLWHTDNIGNYSVCNELR | Phi29 tail protein<br>channel/nanopore/<br>phi29-gp9<br>E595C |
| SEQ ID NO: 16 | MTLSKIKLFYNTPFNNMQNTLHFNSNEERDAYFN<br>SKFDVHEFTSTFNYRNMKGVLRVTIDLVSDRSCF<br>EQLMGVNYCQVQYIQSNRVEYLFVTDIQQLNDK<br>VCELSLVPDVVMTYTQGNVLNTLNNVNVIRQHY<br>TQTEYEQNLEQIRSNNDVLATSTMRVHAIKSELFT<br>QLEYILTIGANLRKSFGTAEKPKFPSSSGSTHDGIY<br>NPYDMYWFNDYESLKEVMDYLTGYPWIQQSIKN<br>VTIIPSGFIKQESLNDHEPVNGGDLSVRKLGKQGV<br>SNQKDFNAISLDYQSLMFTLGLNPINDKHLLRPNI<br>VTAELTDYAGNRLPIDLSLIETNLEFDSFVTMGAK<br>NEIKVYVKNYNARGNNVGQYIDNALTINNFDTIG<br>FSVDSGELGKANSAYSRELSNSRQMSSRINTVLD<br>NDASVKDRLFNAISLSGGLSIKSALSGFNNEYEHY<br>RDQKAQFKQMDALPNAITEGHVGYAPLFKQDKF<br>GVHLRLGRISQDELNNVKKYYNMFGYECNDYST<br>KLSDITSMSICNWVQFKGIWTLPNVDTGHMNMLR<br>ALFEAGVRLWHKESDMINNTVVNNVIIKSLEHHH<br>HHH | Bacteriophage C1<br>tail protein<br>channel/nanopore/<br>WT |
| SEQ ID NO: 17 | MQNNSYGYAVSVRVGGKEHRHWERYDIDSDFLI<br>PADSFDFVIGRLGPEAAIPDLSGESCEVVIDGQIVM<br>TGIIGSQRHGKSKGSRELSLSGRDLAGFLVDCSAP<br>QLNVKGMTVLDAAKKLAAPWPQIKAVVLKAEN<br>NPALGKIDIEPGETVWQALTHIANSVGLHPWLEPD<br>GTLVVGGADYSSPPVATLCWSRTDSRCNIERMDI<br>EWDTDNRFSEVTFLAQSHGRSGDSAKHDLKWVY<br>KDPTMTLHRPKTVVVSDADNLAALQKQAKKQLA<br>DWRLEGFTLTITVGGHKTRDGVLWQPGLRVHVID<br>DEHGIDAVFFLMGRRFMLSRMDGTQTELRLKED<br>GIWTPDAYPKKAEAARKRKGKRKGVSHKGKKG<br>GKKQAETAVFE | *Neisseria<br>meningitidis*<br>serogroup B tail<br>protein<br>channel<br>channel/nanopore/<br>WT |

TABLE 1-continued

Amino Acid Sequences of Channel Proteins

| SEQ ID NO | Sequences | Other information |
|---|---|---|
| SEQ ID NO: 18 | MFVDDVTRAFESGDFARPNLFQVEISYLGQNFTF QCKATALPAGIVEKIPVGFMNRKINVAGDRTFDD WTVTVMNDEAHDARQKFVDWQSIAAGQGNEITG GKPAEYKKSAIVRQYARDAKTVTKEIEIKGLWPT NVGELQLDWDSNNEIQTFEVTLALDYWE | Bacteriophage T4 tail protein channel/nanopore/ WT |
| SEQ ID NO: 19 | MVDAGFENQKELTKMQLDNQKEIAEMQNETQKE IAGIQSATSRQNTKDQVYAQNEMLAYQQKESTAR VASIMENTNLSKQQQVSEIMRQMLTQAQTAGQY FTNDQIKEMTRKVSAEVDLVHQQTQNQRYGSSHI GATAKD | Bacteriophage phiX174 tail protein channel/nanopore/ WT |
| SEQ ID NO: 20 | MPVPNPTMPVKGAGTTLWVYKGSGDPYANPLSD VDWSRLAKVKDLTPGELTAESYDDSYLDDEDAD WTATGQGQKSAGDTSFTLAWMPGEQGQQALLA WFNEGDTRAYKIRFPNGTVDVFRGWVSSIGKAVT AKEVITRTVKVTNVGRPSMAEDRSTVTAATGMT VTPASTSVVKGQSTTLTVAFQPEGVTDKSFRAVS ADKTKATVSVSGMTITVNGVAAGKVNIPVVSGN GEFAAVAEITVTAS | Escherichia phage lambda (Bacteriophage lambda) tail protein channel/nanopore/ WT |
| SEQ ID NO: 21 | NIYDILDKVFTMMYDGQDLTDYFLVQEVRGRSV YSIEMGKRTIAGVDGGVITTESLPARELEVDAIVF GDGTETDLRRRIEYLNFLLHRDTDVPITFSDEPSRT YYGRYEFATEGDEKGGFHKVTLNFYCQDDPLKYG PEVTTDVTTASTPVKNTGLAVTNPTIRCVFSTSAT EYEMQLLDGSTVVKFLKVVYGFNTGDTLVIDCHE RSVTLNGQDIMPALLIQSDWIQLKPQVNTYLKAT QPSTIVFTEKFL | Bacteriophage SPP1 tail protein channel/nanopore/ WT |
| SEQ ID NO: 22 | MSLQLLRNTRIFVSTVKTGHNKTNTQEILVQDDIS WGQDSNSTDITVNEAGPRPTRGSKRFNDSLNAAE WSFSTYILPYKDKNTSKQIVPDYMLWHALSSGRA INLEGTTGAHNNATNFMVNFKDNSYHELAMLHIY ILTDKTWSYIDSCQINQAEVNVDIEDIGRVTWSGN GNQLIPLDEQPFDPDQIGIDDETYMTIQGSYIKNKL TILKIKDMDTNKSYDIPITGGTFTINNNITYLTPNV MSRVTIPIGSFTGAFELTGSLTAYLNDKSLGSMEL YKDLIKTLKVVNRFEIALVLGGEYDDERPAAILVA KQAHVNIPTIETDDVLGTSVEFKAIPSDLDAGDEG YLGFSSKYTRTTINNLIVNGDGATDAVTAITVKSA GNVTTLNRSATLQMSVEVTPSSARNKEVTWAITA GDAATINATGLLRADASKTGAVTVEATAKDGSG VKGTKVITVTAGG | Escherichia phage T5 tail protein channel/nanopore/ WT |
| SEQ ID NO: 23 | MAGNQRQGVAFIRVNGMELESMEGASFTPSGITR EEVTGSRVYGWKGKPRAAKVECKIPGGGPIGLDE IIDWENITVEFQADTGETWMLANAWQADEPKND GGEISLVLMAKQSKRIA | Escherichia phage Mu tail protein channel/nanopore/ WT |
| SEQ ID NO: 24 | MPVPNPTMPVKGAGTTLWVYKGSGDPYANPLSD VDWSRLAKVKDLTPGELTAESYDDSYLDDEDAD WTATGQGQKSAGDTSFTLAWMPGEQGQQALLA WFNEGDTRAYKIRFPNGTVDVFRGWVSSIGKAVT AKEVITRTVKVTNVGRPSMAEDRSTVTAATGMT VTPASTSVVKGQSTTLTVAFQPEGVTDKSFRAVS ADKTKATVSVSGMTITVNGVAAGKVNIPVVSGN GEFAAVAEITVTAS | Escherichia phage lambda tail protein channel/nanopore/ WT |
| SEQ ID NO: 25 | MKLDYNSREIFFGNEALIVADMTKGSNGKPEFTN HKIVTGLVSVGSMEDQAETNSYPADDVPDHGVK KGATLLQGEMVFIQTDQALKEDMLGQQRTENGL GWSPTGNWKTKCVQYLIKGRKRDKVTGEFVDGY RVVVYPHLTPTAEATKESETDSVDGVDPIQWTLA VQATESDIYSNGGKKVPAIEYEIWGEQAKDFAKK MESGLFIMQPDTVLAGAITLVAPVIPNVTTATKGN NDGTIVVPDTLKDSKGGTVKVTSVIKDAHGKVAT NGQLAPGVYIVTFSADGYEDVTAGVSVTDHS | Lactococcus phage F4-1 tail protein channel/nanopore/ WT |
| SEQ ID NO: 26 | MAMPRKLKLMNVFLNGYSYQGVAKSVTLPKLTR KLENYRGAGMNGSAPVDLGLDDDALSMEWSLG GFPDSVIWELYAATGVDAVPIRFAGSYQRDDTGE TVAVEVVMRGRQKEIDTGEGKQGEDTESKISVVC TYFRLTMDGKELVEIDTINMIEKVNGVDRLEQHR RNIGL | Escherichia phage P2 tail protein channel/nanopore/ WT |

Amino Acid Sequences of Channel Proteins

| SEQ ID NO | Sequences | Other information |
|---|---|---|
| SEQ ID NO: 27 | MATVNEFRGAMSRGGGVQRQHRWRVTISFPSFA ASADQTRDVCLLAVTTNTPTGQLGEILVPWGGRE LPFPGDRRFEALPITFINVVNNGPYNSMEVWQQYI NGSESNRASANPDEYFRDVVLELLDANDNVTKT WTLQGAWPQNLGQLELDMSAMDSYTQFTCDLR YFQAVSDRSR | *Serratia* phage KSP90 tail protein channel/nanopore/ WT |
| SEQ ID NO: 28 | MRSYEMNIETAEELSAVNDILASIGEPPVSTLEGD ANADVANARRVLNKINRQIQSRGWTFNIEEGVTL LPDAFSGMIPFSSDYLSVMATSGQTQYVNRGGYL YDRSAKTDRFPSGVQVNLIRLREFDEMPECFRNYI VTKASRQFNNRFFGAPEVDGVLQEEEQEAWSACF EYELDYGNYNMLDGDAFTSGLLNR | *Enterobacteria* phage T7M tail protein channel/nanopore/ WT |
| SEQ ID NO: 29 | MAIDVLDVISLSLFKQQIEFEEDDRDELITLYAQA AFDYCMRWCDEPAWKVAADIPAAVKGAVLLVF ADMFEHRTAQSEVQLYENAAAERMMFIHRNWR GKAESEEGS | Bacteriophage HK97 tail protein channel/nanopore/ WT |
| SEQ ID NO: 30 | MARKRSNTYRSINEIQRQKRNRWFIHYLNYLQSL AYQLFEWENLPPTINPSFLEKSIHQFGYVGFYKDP VISYIACNGALSGQRDVYNQATVFRAASPVYQKE FKLYNYRDMKEEDMGVVIYNNDMAFPTTPTLEL FAAELAELKEIISVNQNAQKTPVLIRANDNNQLSL KQVYNQYEGNAPVIFAHEALDSDSIEVFKTDAPY VVDKLNAQKNAVWNEMMTFLGIKNANLEKKER MVTDEVSSNDEQIESSGTVFLKSREEACEKINELY GLNVKVKFRYDIVEQMRRELQQIENVSRGTSDGE TNE | Bacteriophage Phi29 portal protein channel/nanopore/ WT |
| SEQ ID NO: 31 | TYRSINEIQRQKRNRWFIHYLNYLQSLAYQLFEW ENLPPTINPSFLEKSIHQFGYVGFYKDPVISYIACN GALSGQRDVYNQATVFRAASPVYQKEFKLYNYR DMKEEDMGVVIYNNDMAFPTTPTLELFAAELAEL KEIISVNQNAQKTPVLIRANDNNQLSLKQVYNQY EGNAPVIFAHEALDSDSIEVFKTDAPYVVDKLNA QKNAVWNEMMTFLGIKNANLEKKERMVTDEVSS NDEQIESSGTVFLKSREEACEKINELYGLNVKVKF RYDIVEQMRRELQQIENVSRGTSDGETNEAHIVM VDAYKPTK | Bacteriophage Phi29 portal protein channel/nanopore/ phi29 gp10 Δ1-7 |
| SEQ ID NO: 32 | TYLSINVIQLQKRNRWFIHYLNYLQSLAYQLFEW ENLPPTINPSFLEKSIHQFGYVGFYKDPVISYIACN GALSGQRDVYNQATVFRAASPVYQKEFKLYNYR DMKEEDMGVVIYNNDMAFPTTPTLELFAAELAEL KEIISVNQNAQKTPVLIRANDNNQLSLKQVYNQY EGNAPVIFAHEALDSDSIEVFKTDAPYVVDKLNA QKNAVWNEMMTFLGIKNANLEKKERMVTDEVSS NDEQIESSGTVFLKSREEACEKINELYGLNVKVKF RYDIVEQMRRELQQIENVSRGTSDGETNEAHIVM VDAYKPTK | Bacteriophage Phi29 portal protein channel/nanopore/ phi29 gp10 Δ1-7 R10L, E14V, R17L |
| SEQ ID NO: 33 | ILTYLSINVIQLQKRNRWFIHYLNYLQSLAYQLFE WENLPPTINPSFLEKSIHQFGYVGFYKDPVISYIAC NGALSGQRDVYNQATVFRAASPVYQKEFKLYNY RDMKEEDMGVVIYNNDMAFPTTPTLELFAAELAE LKEIISVNQNAQKTPVLIRANDNNQLSLKQVYNQ YEGNAPVIFAHEALDSDSIEVFKTDAPYVVDKLN AQKNAVWNEMMTFLGIKNANLEKKERMVTDEV SSNDEQIESSGTVFLKSREEACEKINELYGLNVKV KFRYDIVEQMRRELQQIENVSRGTSDGETNEAHIV MVDAYKPTK | Bacteriophage Phi29 portal protein channel/nanopore/ phi29 gp10 Δ1-7 N-ter IL, R10L, E14V, R17L |
| SEQ ID NO: 34 | ILVAILTYLSINVIQLQKRNRWFIHYLNYLQSLAY QLFEWENLPPTINPSFLEKSIHQFGYVGFYKDPVIS YIACNGALSGQRDVYNQATVFRAASPVYQKEFKL YNYRDMKEEDMGVVIYNNDMAFPTTPTLELFAA ELAELKEIISVNQNAQKTPVLIRANDNNQLSLKQV YNQYEGNAPVIFAHEALDSDSIEVFKTDAPYVVD KLNAQKNAVWNEMMTFLGIKNANLEKKERMVT DEVSSNDEQIESSGTVFLKSREEACEKINELYGLN VKVKFRYDIVEQMRRELQQIENVSRGTSDGETNE AHIVMVDAYKPTK | Bacteriophage Phi29 portal protein channel/nanopore/ phi29 gp10 Δ1-7 N-ter ILVAIL, R10L, E14V, R17L |
| SEQ ID NO: 35 | MARKRSNTYRSINEIQRQKRNRWFIHYLNYLQSL AYQLFEWENLPPTINPSFLEKSIHQFGYVGFYKDP | Bacteriophage Phi29 portal |

TABLE 1-continued

| Amino Acid Sequences of Channel Proteins | | |
| --- | --- | --- |
| SEQ ID NO | Sequences | Other information |
| | VISYIACNGCLSGQRDVYNQATVFRAASPVYQKE FKLYNYRDMKEEDMGVVIYNNDMAFPTTPTLCL FAAELAELKEIISVNQNAQKTPVLIRANDNNCLSL KQVYNQYEGNAPVIFAHEALDSDSIEVFKTDAPY VVDKLNAQKNAVWNEMMTFLGIKNANLEKKER MVTDEVSSNDEQIESSGTVFLKSREEACEKINELY GLNVKVKFRYDIVEQMRRELQQIENVSRGTSDGE TNE | protein channel/nanopore/ phi29 gp10 A79C, E135C, Q168C |

TABLE 2

| Sequences of Linkers and Probes | | |
| --- | --- | --- |
| SEQ ID NO: 36 | AHIVMVDAYKPTK | Spytag/ Conjugation Linker |
| SEQ ID NO: 37 | DYDIPTTENLYFQGAMVDTLSGLSSEQGQSGDMT IEEDSATHIKFSKRDEDGKELAGATMELRDSSGKT ISTWISDGQVKDFYLYPGKYTFVETAAPDGYEVA TAITFTVNEQGQVTVNGKATKGDAHI | SpyCatcher/ Conjugation Linker |
| SEQ ID NO: 38 | MALTQPSSVSANPGETVKITCSGSSGSYGWYQQK SPDSAPVTVIYQSNQRPSDIPSRFSGSKSGSTGTLTI TGVQAEDEAVYYCGGWGSSVGMFGAGTTLTVL GQSSRSSGGGGSSGGGGSAVTLDESGGGLQTPGG ALSLVCKASGFTFSSYAMGWVRQAPGKGLEWVA GISDDGDSYISYATAVKGRATISRDNGQSTVRLQL NNLRAEDTATYYCARSHCSGCRNAALIDAWGHG TEVIVSSMSYY | Anti-PSA single chain antibody/probe |
| SEQ ID NO: 39 | VHSPNKK | Anti-Endothelial vascular adhesion molecule/probe |
| SEQ ID NO: 40 | EVHLQQSLAELVRSGASVKLSCTASGFNIKHYYM HWVKQRPEQGLEWIGWINPENVDTEYAPKFQGK ATMTADTSSNTAYLQLSSLTSEDTAVYYCNHYRY AVGGALDYWGQGTTVTVSSGGGGSGGGGSGGG GSDIELTQSPAIMSASPGEKVTMTCSASSSVSYIH WYQQKSGTSPKRWVYDTSKLASGVPARFSGSGS GTSYSLTISTMEAEVAATYYCQQWNNNPYTFGG GTKLEIK | CEA probe |
| SEQ ID NO: 41 | VKLQESGPGLVAPSQSLSMSCTVSGFSLSSYGVH WVRQPPGKGLEWLGVIWAGGTTNYNSALMSRLS ISKDNSKSQVLLKMNSLQTDDTAMYYCATTTMIT LMDYWGQGTTVTVSS | CEA probe |
| SEQ ID NO: 42 | DVQLNQAKSSLSASLGDRVTISCRASQDISNYLN WYQQKPDGTVKLLIYYTSRLHSGVPPRFSGSGSG TDYSLTISNLEQEDIATYFCQQGNTVPWTFGGGTK LEI | CEA probe |
| SEQ ID NO: 43 | MARSGL | ErbB2 probe |
| SEQ ID NO: 44 | MARAKE | ErbB2 probe |
| SEQ ID NO: 45 | MSRTMS | ErbB2 probe |
| SEQ ID NO: 46 | KCCYSL | ErbB2 probe |
| SEQ ID NO: 47 | WIFPWIQL | GRP78 probe |
| SEQ ID NO: 48 | WDLAWMFRLPVG | GRP78 probe |
| SEQ ID NO: 49 | CTVALPGGYVRVC | GRP78 probe |
| SEQ ID NO: 50 | IPLVVPLGGSCK | Hepsin probe |
| SEQ ID NO: 51 | KTLLPTP | Plectin-1 probe |
| SEQ ID NO: 52 | CVAYCIEHHCWTC | PSA probe |

TABLE 2-continued

Sequences of Linkers and Probes

| SEQ ID NO: 53 | CVFAHNYDYLVC | PSA probe |
|---|---|---|
| SEQ ID NO: 54 | CVFTSNYAFC | PSA probe |
| SEQ ID NO: 55 | SGRSA | uPA probe |
| SEQ ID NO: 56 | WGFP | uPA probe |
| SEQ ID NO: 57 | XFXXYLW | uPA probe |
| SEQ ID NO: 58 | AEPMPHSLNFSQYLWYT | uPA probe |
| SEQ ID NO: 59 | FSRYLWS | uPA probe |
| SEQ ID NO: 60 | IELLQAR | E-selectin probe |
| SEQ ID NO: 61 | DITWDQLWDLMK | E-selectin probe |
| SEQ ID NO: 62 | AYTKCSRQWRTCMTTH | Galectin-3 probe |
| SEQ ID NO: 63 | PQNSKIPGPTFLDPH | Galectin-3 probe |
| SEQ ID NO: 64 | SMEPALPDWWWKMFK | Galectin-3 probe |
| SEQ ID NO: 65 | ANTPCGPYTHDCP | Galectin-3 probe |
| SEQ ID NO: 66 | FQHPSFI | Alpha-fetoprotein (AFP) probe |
| SEQ ID NO: 67 | CVPELGHEC | HSP90 probe |
| SEQ ID NO: 68 | AACCCCUAUCACGAUUAGCAUUAA | MiR-155 probe |
| SEQ ID NO: 69 | AGUCAACAUCAGUCUGAUAAGCUA | MiR21 probe |
| SEQ ID NO: 70 | ACAGUUCUUCAACUGGCAGCUU | MiR-22 probe |
| SEQ ID NO: 71 | AACAACAAAAUCACUAGUCUUCCA | MiR-7 probe |
| SEQ ID NO: 72 | ACAGGCCGGGACAAGUGCAAUA | MiR-92a probe |
| SEQ ID NO: 73 | CAAACACCAUUGUCACACUCCA | MiR-122 probe |
| SEQ ID NO: 74 | GGCUGUCAAUUCAUAGGUCAG | MiR-192 probe |
| SEQ ID NO: 75 | UGGGGUAUUUGACAAACUGACA | MiR-223 probe |
| SEQ ID NO: 76 | AGCCUAUCCUGGAUUACUUGAA | MiR-26a probe |
| SEQ ID NO: 77 | GCGGAACUUAGCCACUGUGAA | MiR-27a probe |
| SEQ ID NO: 78 | ACAAGGAUGAAUCUUUGUUACUG | MiR-802 probe |
| SEQ ID NO: 79 | ATGGCGTTAACCCAACCTAGCAGCGTTAGCGCG AATCCTGGCGAAACCGTGAAAATTACCTGCAGC GGCAGCAGCGGTAGCTATGGCTGGTATCAGCA GAAAAGCCCGGATTCAGCGCCTGTGACCGTGAT TTATCAGAGCAACCAGCGCCCGAGCGATATTCC TAGCCGCTTTAGCGGCAGCAAAAGCGGTAGCA CCGGCACCTTAACCATTACCGGTGTGCAGGCGG AAGATGAAGCGGTGTATTATTGCGGCGGTTGGG GTTCAAGCGTTGGCATGTTTGGTGCGGGTACCA CCTTAACCGTGTTAGGTCAGAGCAGCCGTTCAA GCGGTGGCGGTGGTAGCAGCGGTGGTGGTGGT AGCGCAGTTACCCTGGATGAAAGCGGTGGCGG CTTACAAACTCCTGGTGGTGCGCTGAGCTTAGT TTGTAAAGCGAGCGGCTTTACCTTTAGCAGCTA TGCGATGGGTTGGGTGCGTCAGGCGCCTGGTAA AGGCTTAGAATGGGTGGCGGGCATTAGCGATG ATGGCGATAGCTATATTAGCTATGCGACCGCGG TTAAAGGTCGTGCGACCATTAGCCGTGATAACG GCCAGAGCACCGTTCGTCTGCAGCTGAATAACC TGCGCGCGGAAGATACCGCGACCTATTATTGCG CGCGCAGCCATTGTAGCGGTTGTCGTAACGCGG CGCTGATTGATGCATGGGGCCATGGCACCGAAG TGATTGTGAGCAGCATGTCGTACTACCATCACC ATCACCATCACGATTACGACATCCCAACGACCG AAAACCTGTATTTTCAGGGCGCCATGGTTGATA | Anti-PSA single chain antibody-SPYCATCHER |

TABLE 2-continued

| Sequences of Linkers and Probes |
| --- |
| CCTTATCAGGTTTATCAAGTGAGCAAGGTCAGT |
| CCGGTGATATGACAATTGAAGAAGATAGTGCTA |
| CCCATATTAAATTCTCAAAACGTGATGAGGACG |
| GCAAAGAGTTAGCTGGTGCAACTATGGAGTTGC |
| GTGATTCATCTGGTAAAACTATTAGTACATGGA |
| TTTCAGATGGACAAGTGAAAGATTTCTACCTGT |
| ATCCAGGAAAATATACATTTGTCGAAACCGCAG |
| CACCAGACGGTTATGAGGTAGCAACTGCTATTA |
| CCTTTACAGTTAATGAGCAAGGTCAGGTTACTG |
| TAAATGGCAAAGCAACTAAAGGTGACGCTCAT |
| ATTTAA |

TABLE 3

| | Nucleic Acid Sequences | |
| --- | --- | --- |
| SEQ ID NO: 80 | ATGAATCATAAACATCATCATCATCATCACAGC AGCGGCGAAAACCTGTATTTTCAGGGCCATATG GGATCCGCCGACAATGAAAACAGGCTGGAGAG CATCCTGTCGCGCTTTGATGCGGACTGGACAGC CAGTGATGAAGCCAGACGAGAGGCAAAGAATG ATCTCTTCTTCTCCCGCGTATCTCAGTGGGATGA CTGGCTATCACAATACACAACCCTGCAGTATCG CGGGCAGTTCGATGTTGTACGTCCAGTGGTGCG CAAGCTCGTTTCTGAGATGCGTCAGAACCCTAT TGATGTTCTGTATCGTCCAAAGGACGGAGCAAG ACCTGATGCCGCTGATGTGCTTATGGGTATGTA TCGCACAGACATGCGGCATAACACGGCTAAAA TCGCGGTTAACATCGCTGTTCGTGAGCAGATTG AAGCTGGAGTTGGTGCGTGGCGTCTGGTCACTG ACTACGAAGACCAAAGTCCGACGAGCAACAAT CAGGTTATCCGTCGAGAGCCTATCCATAGTGCC TGCTCCCATGTTATCTGGGACAGCAACAGCAAA CTGATGGATAAGTCTGACGCCCGTCACTGCACA GTTATCCACTCAATGAGCCAGAATGGTTGGGAG GATTTCGCAGAAAAATACGACCTCGATGCGGAT GATATTCCATCATTCCAGAACCCCAACGATTGG GTATTTCCATGGCTGACGCAGGACACAATTCAG ATCGCTGAGTTTTACGAAGTGGTCGAGAAGAAA GAGACGGCGTTTATCTACCAAGACCCGGTTACG GGTGAGCCGGTAAGCTACTTTAAGCGCGATATT AAAGACGTCATCGATGACCTGGCTGATAGTGGA TTTATCAAAATTGCAGAGCGCCAGATTAAGCGT CGCCGGGTATACAAATCGATTATCACCTGCACT GCTGTACTCAAAGACAAGCAGCTCATTGCTGGC GAGCATATCCCCATTGTTCCGGTGTTCGGAGAG TGGGGCTTCGTTGAAGATAAAGAAGTGTATGAG GGTGTCGTCCGCCTGACAAAAGACGGCCAGCGT CTGCGCAACATGATTATGTCGTTCAACGCCGAC ATCGTGGCCCGCACTCCGAAGAAGAAGCCGTTC TTCTGGCCTGAGCAGATTGCAGGCTTTGAGCAT ATGTACGACGGTAACGACGATTACCCATACTAC CTGCTCAATCGCACTGACGAAAATAGTGGAGAC CTTCCGACTCAGCCGCTGGCATATTATGAAAAC CCGGAAGTGCCGCAAGCCAACGCCTACATGCTG GAAGCAGCAACCAGCGCAGTAAAAGAGGTTGC CACTCTCGGAGTTGATACAGAAGCGGTAAATGG CGGACAGGTTGCGTTTGATACCGTCAATCAACT GAATATGAGGGCTGACCTTGAGACATACGTGTT TCAGGATAATCTGGCTACCGCCATGCGCCGTGA CGGAGAGATTTACCAGTCGATAGTTAATGACAT CTACGATGTTCCTCGCAACGTTACGATTACCCTT GAGGATGGCAGCGAGAAAGATGTTCAGCTAAT GGCTGAGGTTGTTGACCTTGCTACTGGAGAAAA GCAGGTACTAAACGATATCAGGGGGCGCTATG AGTGCTACACGGATGTTGGACCATCATTCCAGT CCATGAAGCAGCAAAACCGCGCAGAAATTCTT GAGTTGCTCGGCAAGACGCCACAGGGAACGCC AGAATATCAACTGCTGTTGCTTCAGTACTTCAC CCTGCTTGATGGTAAAGGTGTTGAGATGATGCG TGACTATGCCAACAAGCAGCTTATTCAGATGGG CGTTAAGAAGCCAGAAACGCCCGAAGAGCAGC AATGGTTAGTAGAGGCGCAACAAGCCAAACAA GGTGGAGGAGGAGGAGGAAAGCTTGCGTTAAC CCAACCTAGCAGCGTTAGCGCGAATCCTGGCGA | P22 portal protein channel Barrel deletion-anti-PSA single chain antibody (channel with probe) |

TABLE 3-continued

Nucleic Acid Sequences

AACCGTGAAAATTACCTGCAGCGGCAGCAGCG
GTAGCTATGGCTGGTATCAGCAGAAAAGCCCG
GATTCAGCGCCTGTGACCGTGATTTATCAGAGC
AACCAGCGCCCGAGCGATATTCCTAGCCGCTTT
AGCGGCAGCAAAAGCGGTAGCACCGGCACCTT
AACCATTACCGGTGTGCAGGCGGAAGATGAAG
CGGTGTATTATTGCGGCGGTTGGGGTTCAAGCG
TTGGCATGTTTGGTGCGGGTACCACCTTAACCG
TGTTAGGTCAGAGCAGCCGTTCAAGCGGTGGCG
GTGGTAGCAGCGGTGGTGGTGGTAGCGCAGTTA
CCCTGGATGAAAGCGGTGGCGGCTTACAAACTC
CTGGTGGTGCGCTGAGCTTAGTTTGTAAAGCGA
GCGGCTTTACCTTTAGCAGCTATGCGATGGGTT
GGGTGCGTCAGGCGCCTGGTAAAGGCTTAGAAT
GGGTGGCGGGCATTAGCGATGATGGCGATAGC
TATATTAGCTATGCGACCGCGGTTAAAGGTCGT
GCGACCATTAGCCGTGATAACGGCCAGAGCAC
CGTTCGTCTGCAGCTGAATAACCTGCGCGCGGA
AGATACCGCGACCTATTATTGCGCGCGCAGCCA
TTGTAGCGGTTGTCGTAACGCGGCGCTGATTGA
TGCATGGGGCCATGGCACCGAAGTGATTGTGAG
CAGCTAA

SEQ ID NO: 81    ATGAATCATAAACATCATCATCATCATCACAGC    P22 portal protein
                AGCGGCGAAAACCTGTATTTTCAGGGCCATATG    channel Barrel
                GGATCCGCCGACAATGAAAACAGGCTGGAGAG    deletion-anti-
                CATCCTGTCGCGCTTTGATGCGGACTGGACAGC    VCAM-1
                CAGTGATGAAGCCAGACGAGAGGCAAAGAATG
                ATCTCTTCTTCTCCCGCGTATCTCAGTGGGATGA
                CTGGCTATCACAATACACAACCCTGCAGTATCG
                CGGGCAGTTCGATGTTGTACGTCCAGTGGTGCG
                CAAGCTCGTTTCTGAGATGCGTCAGAACCCTAT
                TGATGTTCTGTATCGTCCAAAGGACGGAGCAAG
                ACCTGATGCCGCTGATGTGCTTATGGGTATGTA
                TCGCACAGACATGCGGCATAACACGGCTAAAA
                TCGCGGTTAACATCGCTGTTCGTGAGCAGATTG
                AAGCTGGAGTTGGTGCGTGGCGTCTGGTCACTG
                ACTACGAAGACCAAAGTCCGACGAGCAACAAT
                CAGGTTATCCGTCGAGAGCCTATCCATAGTGCC
                TGCTCCCATGTTATCTGGGACAGCAACAGCAAA
                CTGATGGATAAGTCTGACGCCCGTCACTGCACA
                GTTATCCACTCAATGAGCCAGAATGGTTGGGAG
                GATTTCGCAGAAAAATACGACCTCGATGCGGAT
                GATATTCCATCATTCCAGAACCCCAACGATTGG
                GTATTTCCATGGCTGACGCAGGACACAATTCAG
                ATCGCTGAGTTTTACGAAGTGGTCGAGAAGAAA
                GAGACGGCGTTTATCTACCAAGACCCGGTTACG
                GGTGAGCCGGTAAGCTACTTTAAGCGCGATATT
                AAAGACGTCATCGATGACCTGGCTGATAGTGGA
                TTTATCAAAATTGCAGAGCGCCAGATTAAGCGT
                CGCCGGGTATACAAATCGATTATCACCTGCACT
                GCTGTACTCAAAGACAAGCAGCTCATTGCTGGC
                GAGCATATCCCCATTGTTCCGGTGTTCGGAGAG
                TGGGGCTTCGTTGAAGATAAAGAAGTGTATGAG
                GGTGTCGTCCGCCTGACAAAAGACGGCCAGCGT
                CTGCGCAACATGATTATGTCGTTCAACGCCGAC
                ATCGTGGCCCGCACTCCGAAGAAGAAGCCGTTC
                TTCTGGCCTGAGCAGATTGCAGGCTTTGAGCAT
                ATGTACGACGGTAACGACGATTACCCATACTAC
                CTGCTCAATCGCACTGACGAAAATAGTGGAGAC
                CTTCCGACTCAGCCGCTGGCATATTATGAAAAC
                CCGGAAGTGCCGCAAGCCAACGCCTACATGCTG
                GAAGCAGCAACCAGCGCAGTAAAAGAGGTTGC
                CACTCTCGGAGTTGATACAGAAGCGGTAAATGG
                CGGACAGGTTGCGTTTGATACCGTCAATCAACT
                GAATATGAGGGCTGACCTTGAGACATACGTGTT
                TCAGGATAATCTGGCTACCGCCATGCGCCGTGA
                CGGAGAGATTTACCAGTCGATAGTTAATGACAT
                CTACGATGTTCCTCGCAACGTTACGATTACCCTT
                GAGGATGGCAGCGAGAAAGATGTTCAGCTAAT
                GGCTGAGGTTGTTGACCTTGCTACTGGAGAAAA
                GCAGGTACTAAACGATATCAGGGGGCGCTATG
                AGTGCTACACGGATGTTGGACCATCATTCCAGT
                CCATGAAGCAGCAAAACCGCGCAGAAATTCTT
                GAGTTGCTCGGCAAGACGCCACAGGGAACGCC
                AGAATATCAACTGCTGTTGCTTCAGTACTTCAC
                CCTGCTTGATGGTAAAGGTGTTGAGATGATGCG
                TGACTATGCCAACAAGCAGCTTATTCAGATGGG TABLE 3-continued

| Nucleic Acid Sequences | | |
|---|---|---|
| | CGTTAAGAAGCCAGAAACGCCCGAAGAGCAGC<br>AATGGTTAGTAGAGGCGCAACAAGCCAAACAA<br>GGTGGTGGCGTACATTCGCCTAACAAGAAGTAA | |
| SEQ ID NO: 82 | ATGAATCATAAACATCATCATCATCATCACAGC<br>AGCGGCGAAAACCTGTATTTTCAGGGCCATATG<br>GGATCCGCCGACAATGAAAACAGGCTGGAGAG<br>CATCCTGTCGCGCTTTGATGCGGACTGGACAGC<br>CAGTGATGAAGCCAGACGAGAGGCAAAGAATG<br>ATCTCTTCTTCTCCCGCGTATCTCAGTGGGATGA<br>CTGGCTATCACAATACACAACCCTGCAGTATCG<br>CGGGCAGTTCGATGTTGTACGTCCAGTGGTGCG<br>CAAGCTCGTTTCTGAGATGCGTCAGAACCCTAT<br>TGATGTTCTGTATCGTCCAAAGGACGGAGCAAG<br>ACCTGATGCCGCTGATGTGCTTATGGGTATGTA<br>TCGCACAGACATGCGGCATAACACGGCTAAAA<br>TCGCGGTTAACATCGCTGTTCGTGAGCAGATTG<br>AAGCTGGAGTTGGTGCGTGGCGTCTGGTCACTG<br>ACTACGAAGACCAAAGTCCGACGAGCAACAAT<br>CAGGTTATCCGTCGAGAGCCTATCCATAGTGCC<br>TGCTCCCATGTTATCTGGGACAGCAACAGCAAA<br>CTGATGGATAAGTCTGACGCCCGTCACTGCACA<br>GTTATCCACTCAATGAGCCAGAATGGTTGGGAG<br>GATTTCGCAGAAAAATACGACCTCGATGCGGAT<br>GATATTCCATCATTCCAGAACCCCAACGATTGG<br>GTATTTCCATGGCTGACGCAGGACACAATTCAG<br>ATCGCTGAGTTTTACGAAGTGGTCGAGAAGAAA<br>GAGACGGCGTTTATCTACCAAGACCCGGTTACG<br>GGTGAGCCGGTAAGCTACTTTAAGCGCGATATT<br>AAAGACGTCATCGATGACCTGGCTGATAGTGGA<br>TTTATCAAAATTGCAGAGCGCCAGATTAAGCGT<br>CGCCGGGTATACAAATCGATTATCACCTGCACT<br>GCTGTACTCAAAGACAAGCAGCTCATTGCTGGC<br>GAGCATATCCCCATTGTTCCGGTGTTCGGAGAG<br>TGGGGCTTCGTTGAAGATAAAGAAGTGTATGAG<br>GGTGTCGTCCGCCTGACAAAAGACGGCCAGCGT<br>CTGCGCAACATGATTATGTCGTTCAACGCCGAC<br>ATCGTGGCCCGCACTCCGAAGAAGAAGCCGTTC<br>TTCTGGCCTGAGCAGATTGCAGGCTTTGAGCAT<br>ATGTACGACGGTAACGACGATTACCCATACTAC<br>CTGCTCAATCGCACTGACGAAAATAGTGGAGAC<br>CTTCCGACTCAGCCGCTGGCATATTATGAAAAC<br>CCGGAAGTGCCGCAAGCCAACGCCTACATGCTG<br>GAAGCAGCAACCAGCGCAGTAAAAGAGGTTGC<br>CACTCTCGGAGTTGATACAGAAGCGGTAAATGG<br>CGGACAGGTTGCGTTTGATACCGTCAATCAACT<br>GAATATGAGGGCTGACCTTGAGACATACGTGTT<br>TCAGGATAATCTGGCTACCGCCATGCGCCGTGA<br>CGGAGAGATTTACCAGTCGATAGTTAATGACAT<br>CTACGATGTTCCTCGCAACGTTACGATTACCCTT<br>GAGGATGGCAGCGAGAAAGATGTTCAGCTAAT<br>GGCTGAGGTTGTTGACCTTGCTACTGGAGAAAA<br>GCAGGTACTAAACGATATCAGGGGGCGCTATG<br>AGTGCTACACGGATGTTGGACCATCATTCCAGT<br>CCATGAAGCAGCAAAACCGCGCAGAAATTCTT<br>GAGTTGCTCGGCAAGACGCCACAGGGAACGCC<br>AGAATATCAACTGCTGTTGCTTCAGTACTTCAC<br>CCTGCTTGATGGTAAAGGTGTTGAGATGATGCG<br>TGACTATGCCAACAAGCAGCTTATTCAGATGGG<br>CGTTAAGAAGCCAGAAACGCCCGAAGAGCAGC<br>AATGGTTAGTAGAGGCGCAACAAGCCAAACAA<br>GGTCAACAAGACCCGGCAATGGTTCAGGCTCA<br>GGGCGTACTCCTGCAGGGGCAGGCTGAACTGG<br>CTAAAGCTCAGAACCAGACGCTGTCCCTGCAAA<br>TCGATGCAGCTAAAGTCGAAGCGCAGAACCAG<br>CTTAACGCTGCCAGAATCGCAGAAATCTTCAAC<br>AACATGGACCTCAGTAAACAATCTGAGTTTAGA<br>GAGTTCCTTAAAACCGTTGCTTCATTCCAGCAG<br>GACCGCAGCGAAGACGCTCGCGCAAATGCTGA<br>GTTACTCCTTAAAGGCGATGAACAGACGCACAA<br>GCAGCGAATGGACATTGCCAACATCCTGCAATC<br>GCAGAGACAAAATCAACCTTCCGGCAGTGTAG<br>CCGAGACACCTCAAGGTGGCGTACATTCGCCTA<br>ACAAGAAGTAA | P22 portal protein<br>channel Full<br>length-anti-<br>VCAM-1 |
| SEQ ID NO: 83 | ATGAATCATAAACATCATCATCATCATCACAGC<br>AGCGGCGAAAACCTGTATTTTCAGGGCCATATG<br>ATTCTGACATACCTGTCTATCAATGTGATACAG | phi29 portal<br>protein channel<br>Δ1-7 N-ter IL, |

TABLE 3-continued

| Nucleic Acid Sequences |
|---|

| | CTTCAAAAACGGAATAGATGGTTTATTCACTAT<br>CTGAACTACCTTCAATCTCTAGCCTATCAGCTAT<br>TTGAGTGGGAGAACCTACCGCCTACGATAAACC<br>CTAGTTTCTTAGAAAAGTCTATTCATCAATTCG<br>GGTACGTGGGGTTCTATAAAGACCCTGTCATCA<br>GTTATATCGCTTGTAATGGCGCTCTATCGGGTC<br>AGAGAGACGTTTACAACCAAGCTACAGTTTTTA<br>GAGCCGCATCTCCTGTGTATCAAAAAGAATTCA<br>AGCTATACAACTATAGAGATATGAAGGAAGAA<br>GATATGGGTGTTGTTATCTACAACAATGACATG<br>GCTTTCCCTACCACGCCAACGCTAGAATTGTTT<br>GCGGCTGAATTGGCTGAATTAAAAGAAATCATA<br>TCGGTCAACCAAAACGCTCAAAAGACACCCGTC<br>TTAATTAGAGCAAATGACAATAACCAACTGAGC<br>TTAAAACAAGTGTATAACCAGTATGAAGGTAAT<br>GCCCCTGTTATCTTCGCTCACGAAGCTCTCGAC<br>AGTGACTCTATAGAAGTGTTTAAGACTGATGCT<br>CCCTATGTGGTGGACAAGTTAAACGCTCAGAAA<br>AATGCAGTATGGAATGAGATGATGACTTTCCTT<br>GGCATTAAGAACGCTAACCTAGAGAAGAAAGA<br>GCGCATGGTTACGGATGAAGTTTCCAGTAACGA<br>TGAACAGATCGAGTCTAGCGGCACTGTATTTTT<br>GAAGTCGAGGGAAGAAGCATGTGAGAAGATTA<br>ATGAGCTATATGGTCTCAATGTTAAAGTTAAAT<br>TCAGATATGACATCGTGGAACAAATGAGACGT<br>GAGCTACAGCAAATAGAAAATGTTTCACGTGG<br>AACATCGGACGGTGAAACAAATGAGGCGCATA<br>TTGTGATGGTGGATGCGTATAAACCGACCAAAT<br>AACTCGAG | R10L, E14V,<br>R17L, C-Spytag |
| SEQ ID NO: 84 | ATGATTCTGACATACCTGTCTATCAATGTGATA<br>CAGCTTCAAAAACGGAATAGATGGTTTATTCAC<br>TATCTGAACTACCTTCAATCTCTAGCCTATCAGC<br>TATTTGAGTGGGAGAACCTACCGCCTACGATAA<br>ACCCTAGTTTCTTAGAAAAGTCTATTCATCAATT<br>CGGGTACGTGGGGTTCTATAAAGACCCTGTCAT<br>CAGTTATATCGCTTGTAATGGCGCTCTATCGGG<br>TCAGAGAGACGTTTACAACCAAGCTACAGTTTT<br>TAGAGCCGCATCTCCTGTGTATCAAAAAGAATT<br>CAAGCTATACAACTATAGAGATATGAAGGAAG<br>AAGATATGGGTGTTGTTATCTACAACAATGACA<br>TGGCTTTCCCTACCACGCCAACGCTAGAATTGT<br>TTGCGGCTGAATTGGCTGAATTAAAAGAAATCA<br>TATCGGTCAACCAAAACGCTCAAAAGACACCC<br>GTCTTAATTAGAGCAAATGACAATAACCAACTG<br>AGCTTAAAACAAGTGTATAACCAGTATGAAGGT<br>AATGCCCCTGTTATCTTCGCTCACGAAGCTCTC<br>GACAGTGACTCTATAGAAGTGTTTAAGACTGAT<br>GCTCCCTATGTGGTGGACAAGTTAAACGCTCAG<br>AAAAATGCAGTATGGAATGAGATGATGACTTTC<br>CTTGGCATTAAGAACGCTAACCTAGAGAAGAA<br>AGAGCGCATGGTTACGGATGAAGTTTCCAGTAA<br>CGATGAACAGATCGAGTCTAGCGGCACTGTATT<br>TTTGAAGTCGAGGGAAGAAGCATGTGAGAAGA<br>TTAATGAGCTATATGGTCTCAATGTTAAAGTTA<br>AATTCAGATATGACATCGTGGAACAAATGAGA<br>CGTGAGCTACAGCAAATAGAAAATGTTTCACGT<br>GGAACATCGGACGGTGAAACAAATGAGCTCGA<br>GCACCACCACCACCACCACTGA | phi29 portal<br>protein channel<br>Δ1-7 N-ter IL,<br>R10L ,E14V,<br>R17L, C-his |
| SEQ ID NO: 85 | ATGGCACGTAAACGCAGTAACACATACCGATCT<br>ATCAATGAGATACAGCGTCAAAAACGGAATAG<br>ATGGTTTATTCACTATCTGAACTACCTTCAATCT<br>CTAGCCTATCAGCTATTTGAGTGGGAGAACCTA<br>CCGCCTACGATAAACCCTAGTTTCTTAGAAAAG<br>TCTATTCATCAATTCGGGTACGTGGGGTTCTAT<br>AAAGACCCTGTCATCAGTTATATCGCTTGTAAT<br>GGCGCTCTATCGGGTCAGAGAGACGTTTACAAC<br>CAAGCTACAGTTTTTAGAGCCGCATCTCCTGTG<br>TATCAAAAAGAATTCAAGCTATACAACTATAGA<br>GATATGAAGGAAGAAGATATGGGTGTTGTTATC<br>TACAACAATGACATGGCTTTCCCTACCACGCCA<br>ACGCTAGAATTGTTTGCGGCTGAATTGGCTGAA<br>TTAAAAGAAATCATATCGGTCAACCAAAACGCT<br>CAAAAGACACCCGTCTTAATTAGAGCCAATGAC<br>AATAACTGCCTGAGCTTAAAACAAGTGTATAAC<br>CAGTATGAAGGTAATGCCCCTGTTATCTTCGCT<br>CACGAAGCTCTCGACAGTGACTCTATAGAAGTG | phi29 portal<br>protein channel-<br>Q168C |

TABLE 3-continued

Nucleic Acid Sequences

TTTAAGACTGATGCTCCCTATGTGGTGGACAAG
TTAAACGCTCAGAAAAATGCAGTATGGAATGA
GATGATGACTTTCCTTGGCATTAAGAACGCTAA
CCTAGAGAAGAAAGAGCGCATGGTTACGGATG
AAGTTTCCAGTAACGATGAACAGATCGAGTCTA
GCGGCACTGTATTTTTGAAGTCGAGGGAAGAAG
CATGTGAGAAGATTAATGAGCTATATGGTCTCA
ATGTTAAAGTTAAATTCAGATATGACATCGTGG
AACAAATGAGACGTGAGCTACAGCAAATAGAA
AATGTTTCACGTGGAACATCGGACGGTGAAACA
AATGAG

SEQ ID NO: 86     ATGGCACGTAAACGCAGTAACACATACCGATCT     phi29 portal
                  ATCAATGAGATACAGCGTCAAAAACGGAATAG     protein channel-
                  ATGGTTTATTCACTATCTGAACTACCTTCAATCT     E135C
                  CTAGCCTATCAGCTATTTGAGTGGGAGAACCTA
                  CCGCCTACGATAAACCCTAGTTTCTTAGAAAAG
                  TCTATTCATCAATTCGGGTACGTGGGGTTCTAT
                  AAAGACCCTGTCATCAGTTATATCGCTTGTAAT
                  GGCGCTCTATCGGGTCAGAGAGACGTTTACAAC
                  CAAGCTACAGTTTTTAGAGCCGCATCTCCTGTG
                  TATCAAAAAGAATTCAAGCTATACAACTATAGA
                  GATATGAAGGAAGAAGATATGGGTGTTGTTATC
                  TACAACAATGACATGGCTTTCCCTACCACGCCA
                  ACGCTATGCTTGTTTGCGGCTGAATTGGCTGAA
                  TTAAAAGAAATCATATCGGTCAACCAAAACGCT
                  CAAAAGACACCCGTCTTAATTAGAGCCAATGAC
                  AATAACCAACTGAGCTTAAAACAAGTGTATAAC
                  CAGTATGAAGGTAATGCCCCTGTTATCTTCGCT
                  CACGAAGCTCTCGACAGTGACTCTATAGAAGTG
                  TTTAAGACTGATGCTCCCTATGTGGTGGACAAG
                  TTAAACGCTCAGAAAAATGCAGTATGGAATGA
                  GATGATGACTTTCCTTGGCATTAAGAACGCTAA
                  CCTAGAGAAGAAAGAGCGCATGGTTACGGATG
                  AAGTTTCCAGTAACGATGAACAGATCGAGTCTA
                  GCGGCACTGTATTTTTGAAGTCGAGGGAAGAAG
                  CATGTGAGAAGATTAATGAGCTATATGGTCTCA
                  ATGTTAAAGTTAAATTCAGATATGACATCGTGG
                  AACAAATGAGACGTGAGCTACAGCAAATAGAA
                  AATGTTTCACGTGGAACATCGGACGGTGAAACA
                  AATGAG SEQ ID NO: 87     ATGGCACGTAAACGCAGTAACACATACCGATCT     phi29 portal
                  ATCAATGAGATACAGCGTCAAAAACGGAATAG     protein channel-
                  ATGGTTTATTCACTATCTGAACTACCTTCAATCT     A79C
                  CTAGCCTATCAGCTATTTGAGTGGGAGAACCTA
                  CCGCCTACGATAAACCCTAGTTTCTTAGAAAAG
                  TCTATTCATCAATTCGGGTACGTGGGGTTCTAT
                  AAAGACCCTGTCATCAGTTATATCGCTTGTAAT
                  GGCTGTCTATCGGGTCAGAGAGACGTTTACAAC
                  CAAGCTACAGTTTTTAGAGCCGCATCTCCTGTG
                  TATCAAAAAGAATTCAAGCTATACAACTATAGA
                  GATATGAAGGAAGAAGATATGGGTGTTGTTATC
                  TACAACAATGACATGGCTTTCCCTACCACGCCA
                  ACGCTAGAATTGTTTGCGGCTGAATTGGCTGAA
                  TTAAAAGAAATCATATCGGTCAACCAAAACGCT
                  CAAAAGACACCCGTCTTAATTAGAGCCAATGAC
                  AATAACCAACTGAGCTTAAAACAAGTGTATAAC
                  CAGTATGAAGGTAATGCCCCTGTTATCTTCGCT
                  CACGAAGCTCTCGACAGTGACTCTATAGAAGTG
                  TTTAAGACTGATGCTCCCTATGTGGTGGACAAG
                  TTAAACGCTCAGAAAAATGCAGTATGGAATGA
                  GATGATGACTTTCCTTGGCATTAAGAACGCTAA
                  CCTAGAGAAGAAAGAGCGCATGGTTACGGATG
                  AAGTTTCCAGTAACGATGAACAGATCGAGTCTA
                  GCGGCACTGTATTTTTGAAGTCGAGGGAAGAAG
                  CATGTGAGAAGATTAATGAGCTATATGGTCTCA
                  ATGTTAAAGTTAAATTCAGATATGACATCGTGG
                  AACAAATGAGACGTGAGCTACAGCAAATAGAA
                  AATGTTTCACGTGGAACATCGGACGGTGAAACA
                  AATGAG SEQ ID NO: 88     ATGGCATATGTACCATTATCAGGAACGAACGTC     phi29-tail protein
                  AGGATTTTAGCTGACGTTCCTTTCTCTAATGATT     channel Δ417-
                  ATAAAAACACGAGATGGTTCACATCTTCAAGTA     491-K358C
                  ATCAGTATAACTGGTTTAACAGCAAATCACGTG
                  TGTATGAAATGAGTAAAGTAACATTCATGGGGT
                  TTAGAGAAAATAAACCATATGTTTCGGTTAGTC TABLE 3-continued Nucleic Acid Sequences TTCCCATAGATAAGCTTTACAGTGCGTCATATA
TTATGTTTCAAAATGCAGACTACGGTAACAAGT
GGTTTTATGCATTTGTAACCGAGTTAGAATTTA
AAAATAGTGCTGTTACCTACGTTCACTTTGAAA
TTGATGTTCTCCAAACATGGATGTTCGATATTA
AATTTCAAGAATCATTCATTGTGAGGGAGCACG
TTAAATTATGGAATGACGACGGGACACCGACTA
TCAACACAATTGATGAGGGTCTCAGCTACGGAA
GTGAATACGACATAGTTTCTGTAGAAAACCATA
AACCATACGACGACATGATGTTTCTCGTGATTA
TTTCCAAAAGCATTATGCATGGGACGCCGGGAG
AAGAGGAAAGCAGGCTAAATGACATAAACGCA
AGCCTGAACGGCATGCCGCAACCTCTCTGCTAC
TATATTCACCCATTCTACAAAGATGGTAAAGTT
CCTAAAACGTATATCGGAGATAACAACGCTAAC
TTGTCTCCTATTGTCAATATGCTCACCAATATCT
TTTCACAGAAGAGCGCTGTTAACGATATTGTCA
ATATGTATGTGACTGATTATATTGGTTTGAAGC
TTGACTATAAAAATGGTGATAAAGAATTGAAGC
TCGATAAAGACATGTTTGAACAGGCGGGTATAG
CTGACGATAAACACGGTAACGTTGACACCATCT
TTGTGAAGAAAATACCTGATTATGAAGCCCTAG
AAATAGACACAGGTGATAAATGGGGTGGCTTC
ACAAAAGACCAAGAAAGCAAACTGATGATGTA
CCCTTACTGCGTTACGGAAATAACTGACTTTAA
AGGCAACCATATGAATCTGAAAACCGAGTACA
TCAATAACAGTAAACTATGTATACAGGTTAGGG
GTTCACTAGGGGTCAGTAACAAGGTTGCCTACA
GTGTTCAGGATTATAACGCAGATAGCGCATTGA
GTGGCGGCAATAGATTGACTGCGTCTCTAGATT
CATCCTTAATCAACAACAACCCAAATGACATAG
CAATACTAAATGACTATCTATCTGCTTATCAGTT
AACGAAAATGGGCGGCAACACAGCGTTTGATT
ACGGGAATGGGTACAGAGGTGTGTACGTCATC
AAAAAGCAATTGAAGGCTGAATACAGACGAAG
TCTATCAAGTTTCTTCCATAAATACGGATACAA
GATTAACAGGGTAAAGAAACCAAATTTAAGAA
CACGAAAAGCATTTAACTATGTTCAGACAAAAG
ACTGTTTCATTTCAGGGGACATCAATAACAATG
ACTTACAGGAAATAAGAACAATTTTCGATAATG
GTATTACTCTTTGGCATACTGACAACATCGGAA
ATTACAGCGTCGAGAATGAATTGAGGTGA SEQ ID NO: 89   ATGGCATATGTACCATTATCAGGAACGAACGTC     phi29-tail protein
AGGATTTTAGCTGACGTTCCTTTCTCTAATGATT     channelΔ4417-
ATAAAAACACGAGATGGTTCACATCTTCAAGTA     491-
ATCAGTATAACTGGTTTAACAGCAAATCACGTG     K134I, D138L,
TGTATGAAATGAGTAAAGTAACATTCATGGGGT     D139L
TTAGAGAAAATAAACCATATGTTTCGGTTAGTC
TTCCCATAGATAAGCTTTACAGTGCGTCATATA
TTATGTTTCAAAATGCAGACTACGGTAACAAGT
GGTTTTATGCATTTGTAACCGAGTTAGAATTTA
AAAATAGTGCTGTTACCTACGTTCACTTTGAAA
TTGATGTTCTCCAAACATGGATGTTCGATATTA
AATTTCAAGAATCATTCATTGTGAGGGAGCACG
TTATTTTATGGAATCTGCTGGGGACACCGACTA
TCAACACAATTGATGAGGGTCTCAGCTACGGAA
GTGAATACGACATAGTTTCTGTAGAAAACCATA
AACCATACGACGACATGATGTTTCTCGTGATTA
TTTCCAAAAGCATTATGCATGGGACGCCGGGAG
AAGAGGAAAGCAGGCTAAATGACATAAACGCA
AGCCTGAACGGCATGCCGCAACCTCTCTGCTAC
TATATTCACCCATTCTACAAAGATGGTAAAGTT
CCTAAAACGTATATCGGAGATAACAACGCTAAC
TTGTCTCCTATTGTCAATATGCTCACCAATATCT
TTTCACAGAAGAGCGCTGTTAACGATATTGTCA
ATATGTATGTGACTGATTATATTGGTTTGAAGC
TTGACTATAAAAATGGTGATAAAGAATTGAAGC
TCGATAAAGACATGTTTGAACAGGCGGGTATAG
CTGACGATAAACACGGTAACGTTGACACCATCT
TTGTGAAGAAAATACCTGATTATGAAGCCCTAG
AAATAGACACAGGTGATAAATGGGGTGGCTTC
ACAAAAGACCAAGAAAGCAAACTGATGATGTA
CCCTTACTGCGTTACGGAAATAACTGACTTTAA
AGGCAACCATATGAATCTGAAAACCGAGTACA
TCAATAACAGTAAACTAAAGATACAGGTTAGG
GGTTCACTAGGGGTCAGTAACAAGGTTGCCTAC
AGTGTTCAGGATTATAACGCAGATAGCGCATTG

TABLE 3-continued

Nucleic Acid Sequences

```
                    AGTGGCGGCAATAGATTGACTGCGTCTCTAGAT
                    TCATCCTTAATCAACAACAACCCAAATGACATA
                    GCAATACTAAATGACTATCTATCTGCTTATCAG
                    TTAACGAAAATGGGCGGCAACACAGCGTTTGAT
                    TACGGGAATGGGTACAGAGGTGTGTACGTCATC
                    AAAAAGCAATTGAAGGCTGAATACAGACGAAG
                    TCTATCAAGTTTCTTCCATAAATACGGATACAA
                    GATTAACAGGGTAAAGAAACCAAATTTAAGAA
                    CACGAAAAGCATTTAACTATGTTCAGACAAAAG
                    ACTGTTTCATTTCAGGGGACATCAATAACAATG
                    ACTTACAGGAAATAAGAACAATTTTCGATAATG
                    GTATTACTCTTTGGCATACTGACAACATCGGAA
                    ATTACAGCGTCGAGAATGAATTGAGGTGA

SEQ ID NO: 90       ATGGCATATGTACCATTATCAGGAACGAACGTC       phi29-tail protein
                    AGGATTTTAGCTGACGTTCCTTTCTCTAATGATT      channel Δ417-
                    ATAAAAACACGAGATGGTTCACATCTTCAAGTA      491-
                    ATCAGTATAACTGGTTTAACAGCAAATCACGTG      K134I, D138L,
                    TGTATGAAATGAGTAAAGTAACATTCATGGGGT      D139L, D158L,
                    TTAGAGAAAATAAACCATATGTTTCGGTTAGTC      E163V
                    TTCCCATAGATAAGCTTTACAGTGCGTCATATA
                    TTATGTTTCAAAATGCAGACTACGGTAACAAGT
                    GGTTTTATGCATTTGTAACCGAGTTAGAATTTA
                    AAAATAGTGCTGTTACCTACGTTCACTTTGAAA
                    TTGATGTTCTCCAAACATGGATGTTCGATATTA
                    AATTTCAAGAATCATTCATTGTGAGGGAGCACG
                    TTATTTTATGGAATCTGCTGGGGACACCGACTA
                    TCAACACAATTGATGAGGGTCTCAGCTACGGAA
                    GTGAATACCTGATAGTTTCTGTAGTTAACCATA
                    AACCATACGACGACATGATGTTTCTCGTGATTA
                    TTTCCAAAAGCATTATGCATGGGACGCCGGGAG
                    AAGAGGAAAGCAGGCTAAATGACATAAAACGCA
                    AGCCTGAACGGCATGCCGCAACCTCTCTGCTAC
                    TATATTCACCCATTCTACAAAGATGGTAAAGTT
                    CCTAAAACGTATATCGGAGATAACAACGCTAAC
                    TTGTCTCCTATTGTCAATATGCTCACCAATATCT
                    TTTCACAGAAGAGCGCTGTTAACGATATTGTCA
                    ATATGTATGTGACTGATTATATTGGTTTGAAGC
                    TTGACTATAAAAATGGTGATAAAGAATTGAAGC
                    TCGATAAAGACATGTTTGAACAGGCGGGTATAG
                    CTGACGATAAACACGGTAACGTTGACACCATCT
                    TTGTGAAGAAAATACCTGATTATGAAGCCCTAG
                    AAATAGACACAGGTGATAAATGGGGTGGCTTC
                    ACAAAAGACCAAGAAAGCAAACTGATGATGTA
                    CCCTTACTGCGTTACGGAAATAACTGACTTTAA
                    AGGCAACCATATGAATCTGAAAACCGAGTACA
                    TCAATAACAGTAAACTAAAGATACAGGTTAGG
                    GGTTCACTAGGGGTCAGTAACAAGGTTGCCTAC
                    AGTGTTCAGGATTATAACGCAGATAGCGCATTG
                    AGTGGCGGCAATAGATTGACTGCGTCTCTAGAT
                    TCATCCTTAATCAACAACAACCCAAATGACATA
                    GCAATACTAAATGACTATCTATCTGCTTATCAG
                    TTAACGAAAATGGGCGGCAACACAGCGTTTGAT
                    TACGGGAATGGGTACAGAGGTGTGTACGTCATC
                    AAAAAGCAATTGAAGGCTGAATACAGACGAAG
                    TCTATCAAGTTTCTTCCATAAATACGGATACAA
                    GATTAACAGGGTAAAGAAACCAAATTTAAGAA
                    CACGAAAAGCATTTAACTATGTTCAGACAAAAG
                    ACTGTTTCATTTCAGGGGACATCAATAACAATG
                    ACTTACAGGAAATAAGAACAATTTTCGATAATG
                    GTATTACTCTTTGGCATACTGACAACATCGGAA
                    ATTACAGCGTCGAGAATGAATTGAGGTGA SEQ ID NO: 91       ATGGCATATGTACCATTATCAGGAACGAACGTC       phi29-tail protein
                    AGGATTTTAGCTGACGTTCCTTTCTCTAATGATT      channel Δ417-491
                    ATAAAAACACGAGATGGTTCACATCTTCAAGTA      K134I, D138L,
                    ATCAGTATAACTGGTTTAACAGCAAATCACGTG      D139L, D158L,
                    TGTATGAAATGAGTAAAGTAACATTCATGGGGT      E163V, E309V, D311V,
                    TTAGAGAAAATAAACCATATGTTTCGGTTAGTC      K321V
                    TTCCCATAGATAAGCTTTACAGTGCGTCATATA
                    TTATGTTTCAAAATGCAGACTACGGTAACAAGT
                    GGTTTTATGCATTTGTAACCGAGTTAGAATTTA
                    AAAATAGTGCTGTTACCTACGTTCACTTTGAAA
                    TTGATGTTCTCCAAACATGGATGTTCGATATTA
                    AATTTCAAGAATCATTCATTGTGAGGGAGCACG
                    TTATTTTATGGAATCTGCTGGGGACACCGACTA
                    TCAACACAATTGATGAGGGTCTCAGCTACGGAA
                    GTGAATACCTGATAGTTTCTGTAGTTAACCATA
```

TABLE 3-continued

Nucleic Acid Sequences

```
AACCATACGACGACATGATGTTTCTCGTGATTA
TTTCCAAAAGCATTATGCATGGGACGCCGGGAG
AAGAGGAAAGCAGGCTAAATGACATAAACGCA
AGCCTGAACGGCATGCCGCAACCTCTCTGCTAC
TATATTCACCCATTCTACAAAGATGGTAAAGTT
CCTAAAACGTATATCGGAGATAACAACGCTAAC
TTGTCTCCTATTGTCAATATGCTCACCAATATCT
TTTCACAGAAGAGCGCTGTTAACGATATTGTCA
ATATGTATGTGACTGATTATATTGGTTTGAAGC
TTGACTATAAAAATGGTGATAAAGAATTGAAGC
TCGATAAAGACATGTTTGAACAGGCGGGTATAG
CTGACGATAAACACGGTAACGTTGACACCATCT
TTGTGAAGAAATACCTGATTATGAAGCCCTAG
TTATAGTTACAGGTGATAAATGGGGTGGCTTCA
CAAAAGACCAAGAAAGCAAACTGATGATGTAC
CCTTACTGCGTTACGGAAATAACTGACTTTAAA
GGCAACCATATGAATCTGAAAACCGAGTACATC
AATAACAGTAAACTAAAGATACAGGTTAGGGG
TTCACTAGGGGTCAGTAACAAGGTTGCCTACAG
TGTTCAGGATTATAACGCAGATAGCGCATTGAG
TGGCGGCAATAGATTGACTGCGTCTCTAGATTC
ATCCTTAATCAACAACAACCCAAATGACATAGC
AATACTAAATGACTATCTATCTGCTTATCAGTT
AACGAAAATGGGCGGCAACACAGCGTTTGATT
ACGGGAATGGGTACAGAGGTGTGTACGTCATC
AAAAAGCAATTGAAGGCTGAATACAGACGAAG
TCTATCAAGTTTCTTCCATAAATACGGATACAA
GATTAACAGGGTAAAGAAACCCAAATTTAAGAA
CACGAAAAGCATTTAACTATGTTCAGACAAAG
ACTGTTTCATTTCAGGGGACATCAATAACAATG
ACTTACAGGAAATAAGAACAATTTTCGATAATG
GTATTACTCTTTGGCATACTGACAACATCGGAA
ATTACAGCGTCGAGAATGAATTGAGGTGA
```

SEQ ID NO: 92

```
ATGAATCATAAACATCATCATCATCATCACAGC
AGCGGCGAAAACCTGTATTTTCAGGGCCATATG
GGATCCATGGCATATGTACCATTATCAGGAACG
AACGTCAGGATTTTAGCTGACGTTCCTTTCTCTA
ATGATTATAAAAACACGAGATGGTTCACATCTT
CAAGTAATCAGTATAACTGGTTTAACAGCAAAT
CACGTGTGTATGAAATGAGTAAAGTAACATTCA
TGGGGTTTAGAGAAAATAAACCATATGTTTCGG
TTAGTCTTCCCATAGATAAGCTTTACAGTGCGT
CATATATTATGTTTCAAAATGCAGACTACGGTA
ACAAGTGGTTTTATGCATTTGTAACCGAGTTAG
AATTTAAAAATAGTGCTGTTACCTACGTTCACT
TTGAAATTGATGTTCTCCAAACATGGATGTTCG
ATATTAAATTTCAAGAATCATTCATTGTGAGGG
AGCACGTTAAATTATGGAATGACGACGGGACA
CCGACTATCAACACAATTGATGAGGGTCTCAGC
TACGGAAGTGAATACGACATAGTTTCTGTAGAA
AACCATAAACCATACGACGACATGATGTTTCTC
GTGATTATTTCCAAAAGCATTATGCATGGGACG
CCGGGAGAAGAGGAAAGCAGGCTAAATGACAT
AAACGCAAGCCTGAACGGCATGCCGCAACCTCT
CTGCTACTATATTCACCCATTCTACAAAGATGG
TAAAGTTCCTAAAACGTATATCGGAGATAACAA
CGCTAACTTGTCTCCTATTGTCAATATGCTCACC
AATATCTTTTCACAGAAGAGCGCTGTTAACGAT
ATTGTCAATATGTATGTGACTGATTATATTGGTT
TGAAGCTTGACTATAAAAATGGTGATAAAGAAT
TGAAGCTCGATAAAGACATGTTTGAACAGGCG
GGTATAGCTGACGATAAACACGGTAACGTTGAC
ACCATCTTTGTGAAGAAATACCTGATTATGAA
GCCCTAGAAATAGACACAGGTGATAAATGGGG
TGGCTTCACAAAAGACCAAGAAAGCAAACTGA
TGATGTACCCTTACTGCGTTACGGAAATAACTG
ACTTTAAAGGCAACCATATGAATCTGAAAACCG
AGTACATCAATAACAGTAAACTAAAGATACAG
GTTAGGGGTTCACTAGGGGTCAGTAACAAGGTT
GCCTACAGTGTTCAGGATTATAACGCAGATAGC
GCATTGAGTGGCGGCAATAGATTGACTGCGTCT
CTAGATTCATCCTTAATCAACAACAACCCAAAT
GACATAGCAATACTAAATGACTATCTATCTGCT
TATCAGTTAACGAAAATGGGCGGCAACACAGC
GTTTGATTACGGGAATGGGTACAGAGGTGTGTA
CGTCATCAAAAAGCAATTGAAGGCTGAATACA
GACGAAGTCTATCAAGTTTCTTCCATAAATACG
``` phi29-tail protein
channel Δ417-
491-N-his

TABLE 3-continued

| Nucleic Acid Sequences |
|---|

|  | GATACAAGATTAACAGGGTAAAGAAACCAAAT<br>TTAAGAACACGAAAAGCATTTAACTATGTTCAG<br>ACAAAAGACTGTTTCATTTCAGGGGACATCAAT<br>AACAATGACTTACAGGAAATAAGAACAATTTTC<br>GATAATGGTATTACTCTTTGGCATACTGACAAC<br>ATCGGAAATTACAGCGTCGAGAATGAATTGAG<br>GTGA |  |
| SEQ ID NO: 93 | ATGGCATATGTACCATTATCAGGAACGAACGTC<br>AGGATTTTAGCTGACGTTCCTTTCTCTAATGATT<br>ATAAAAACACGAGATGGTTCACATCTTCAAGTA<br>ATCAGTATAACTGGTTTAACAGCAAATCACGTG<br>TGTATGAAATGAGTAAAGTAACATTCATGGGGT<br>TTAGAGAAAATAAACCATATGTTTCGGTTAGTC<br>TTCCCATAGATAAGCTTTACAGTGCGTCATATA<br>TTATGTTTCAAAATGCAGACTACGGTAACAAGT<br>GGTTTTATGCATTTGTAACCGAGTTAGAATTTA<br>AAAATAGTGCTGTTACCTACGTTCACTTTGAAA<br>TTGATGTTCTCCAAACATGGATGTTCGATATTA<br>AATTTCAAGAATCATTCATTGTGAGGGAGCACG<br>TTAAATTATGGAATGACGACGGGACACCGACTA<br>TCAACACAATTGATGAGGGTCTCAGCTACGGAA<br>GTGAATACGACATAGTTTCTGTAGAAAACCATA<br>AACCATACGACGACATGATGTTTCTCGTGATTA<br>TTTCCAAAAGCATTATGCATGGGACGCCGGGAG<br>AAGAGGAAAGCAGGCTAAATGACATAAACGCA<br>AGCCTGAACGGCATGCCGCAACCTCTCTGCTAC<br>TATATTCACCCATTCTACAAAGATGGTAAAGTT<br>CCTAAAACGTATATCGGAGATAACAACGCTAAC<br>TTGTCTCCTATTGTCAATATGCTCACCAATATCT<br>TTTCACAGAAGAGCGCTGTTAACGATATTGTCA<br>ATATGTATGTGACTGATTATATTGGTTTGAAGC<br>TTGACTATAAAAATGGTGATAAAGAATTGAAGC<br>TCGATAAAGACATGTTTGAACAGGCGGGTATAG<br>CTGACGATAAACACGGTAACGTTGACACCATCT<br>TTGTGAAGAAAATACCTGATTATGAAGCCCTAG<br>AAATAGACACAGGTGATAAATGGGGTGGCTTC<br>ACAAAAGACCAAGAAAGCAAACTGATGATGTA<br>CCCTTACTGCGTTACGGAAATAACTGACTTTAA<br>AGGCAACCATATGAATCTGAAAACCGAGTACA<br>TCAATAACAGTAAACTAAAGATACAGGTTAGG<br>GGTTCACTAGGGGTCAGTAACAAGGTTGCCTAC<br>AGTGTTCAGGATTATAACGCAGATAGCGCATTG<br>AGTGGCGGCAATAGATTGACTGCGTCTCTAGAT<br>TCATCCTTAATCAACAACAACCCAAATGACATA<br>GCAATACTAAATGACTATCTATCTGCTTATTTAC<br>AGGGCAACAAAAATTCACTAGAGAACCAAAAA<br>TCGTCTATCCTTTTTAATGGCATTATGGGTATGA<br>TCGGCGGAGGTATATCAGCGGGAGCAAGTGCG<br>GCAGGAGGTTCAGCCCTAGGGATGGCTTCATCA<br>GTTACAGGGATGACAAGCACTGCGGGTAATGCT<br>GTTCTACAGATGCAAGCGATGCAAGCCAAGCA<br>AGCCGATATAGCAAACATTCCGCCGCAGTTAAC<br>GAAAATGGGCGGCAACACAGCGTTTGATTACG<br>GGAATGGGTACAGAGGTGTGTACGTCATCAAA<br>AAGCAATTGAAGGCTGAATACAGACGAAGTCT<br>ATCAAGTTTCTTCCATAAATACGGATACAAGAT<br>TAACAGGGTAAAGAAACCAAATTTAAGAACAC<br>GAAAAGCATTTAACTATGTTCAGACAAAAGACT<br>GTTTCATTTCAGGGGACATCAATAACAATGACT<br>TACAGGAAATAAGAACAATTTTCGATAATGGTA<br>TTACTCTTTGGCATACTGACAACATCGGAAATT<br>ACAGCGTCGAGAATGAATTGAGGTGA | phi29 tail protein<br>channel WT |

A polypeptide "variant," as the term is used herein, is a polypeptide that typically differs from a polypeptide specifically disclosed herein in one or more substitutions, deletions, additions and/or insertions. Such variants can be naturally occurring or can be synthetically generated, for example, by modifying one or more of the above polypeptide sequences of the disclosure and evaluating one or more biological activities of the polypeptide as described herein and/or using any of some techniques well known in the art.

For example, certain amino acids can be substituted for other amino acids in a protein structure without appreciable loss of its ability to bind other polypeptides or cells. Since it is the binding capacity and nature of a protein that defines that protein's biological functional activity, certain amino acid sequence substitutions can be made in a protein sequence, and, accordingly, its underlying DNA coding sequence, whereby a protein with like properties is obtained. It is thus contemplated that various changes can be made in the peptide sequences of the disclosed compositions, or corresponding DNA sequences that encode said peptides without appreciable loss of their biological utility or activity.

Variant sequences include those wherein conservative substitutions have been introduced by modification of polynucleotides encoding polypeptides of this disclosure Amino acids can be classified according to physical properties and contribution to secondary and tertiary protein structure. Such conservative modifications include amino acid substitutions, additions, and deletions. Conservative amino acid substitutions are ones in which the amino acid residue is replaced with an amino acid residue having a similar side chain Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

"Sequence identity" or "homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least about 70%, at least about 75%, at least about 80%, at least about 90%, at least about 95%, at least about 98%, or at least about 99% polynucleotide or polypeptide homology with a polynucleotide or polypeptide described herein.

Polypeptide variant sequences may share 70% or more (i.e. 80%, 85%, 90%, 95%, 97%, 98%, 99% or more) sequence identity with the sequences recited in this disclosure. Polypeptide variants may also include polypeptide fragments comprising various lengths of contiguous stretches of amino acid sequences disclosed herein. Polypeptide variant sequences include at least about 5, 10, 15, 20, 30, 40, 50, 75, 100, 150, or more contiguous peptides of one or more of the sequences disclosed herein as well as all intermediate lengths therebetween.

II. Nanopore Assemblies Functionalized With Probes

In one aspect, the nanopore assembly further comprises a probe for detecting an analyte. The probe is operably linked to at least one of the subunits. Such a probe is conjugated to the nanopore assembly to allow for selective binding of one or more analytes. A probe may be conjugated to the nanopore assembly at various stoichiometry (molar ratios between the probe and the nanopore assembly). In one example, the probe may be conjugated to each of the subunits. In another example, only one probe is conjugate the nanopore assembly. Also contemplated is a nanopore assembly including two or more different types of probes. Such functionalized nanopore assemblies can be used to detect analytes, such as nucleic acids, amino acids, peptides, proteins, polymers, and chemical molecules. In some embodiments, the analyte is one of PSA, CEA, AFP, VCAM, MiR-155, MiR-22, MiR-7, MiR-92a, MiR-122, MiR-192, MiR-223, MiR-26a, MiR-27a, MiR-802 or a fragment thereof.

The terms "specific binding," "selective binding," "selectively binds," and "specifically binds," refer to a probe on the nanopore assembly binds to an analyte in the sample more strongly than other contaminants present in the sample. For example, the probe may bind to an analyte with an equilibrium dissociation constant (Kd) of approximately less than $10^{-6}$ M, such as approximately less than $10^{-7}$ M, $10^{-8}$ M, $10^{-9}$ M or $10^{-10}$ M or even lower when determined by a binding assay, e.g., ELISA, equilibrium dialysis or surface plasmon resonance (SPR) technology in a BIA-CORE® 2000 surface plasmon resonance instrument.

The probe can be one of chemicals, carbohydrates, aptamers, nucleic acids, peptide, protein, antibodies, and receptors. In some embodiments, the probe may include a sequence at least 75% identical to a sequence of SEQ ID NOs: 36-79. In some embodiments, the probe is an anti-PSA antibody. The probe is operably linked via covalent bonding to at least one of the subunits. The probe can be linked to a subunit via one or more functional sites on the subunit. Such functional sites can be introduced by mutagenesis, for example, substitution with cysteine or other non-natural amino acids. The probe can also be linked to the channel via well-established chemical methods, including but not limited to ester linkage, click-chemistry, and sulfhydryl linkage. In some embodiments, the probe is operably linked to a location in proximity to an entrance of the channel or to a location at an interior side of the channel

III. Nanopore Assemblies With Membranes

In another aspect, this disclosure provides a nanopore assembly, in which the channel is inserted in the membrane. The polymer membrane can be of various compositions depending on the applications either in stand-alone form or in a microfluidic device. The polymer-membrane embedded channels display robust electrophysiological properties, a pre-requisite feature for single-molecule nanopore-based analysis. The membrane may include a polymer membrane (e.g., planar polymer membrane) or a lipid membrane. The polymer membrane can be either symmetric or asymmetric in nature. For example, the polymer membrane is an alternating copolymer (e.g., A-B-A-B- . . . ) or aperiodic copolymer (e.g., AA-BB-AA-BB . . . ). In another example, the polymer membrane can be a block copolymer comprising of two or more homopolymer subunits linked by covalent bonds. Alternatively, the polymer membrane can be a diblock or triblock copolymer (e.g., PMOXA-PDMS-PMOXA). The polymer membrane can also be a terpolymer consisting of three distinct monomers.

In some embodiments, the polymer membrane comprises an alternating copolymer, a periodic copolymer, a block copolymer, a di-block copolymer, a tri-block copolymer, a terpolymer, or a combination thereof. In some embodiments, the polymer membrane comprises PMOXA-PDMS-PMOXA.

In some embodiment, the channel is embedded in a polymersome of various sizes. In some embodiments, the polymersomes are fused with a planar polymer membrane to insert the channel Polymersomes are composed of hydrophilic-hydrophobic block copolymer, arranged in a bilayer vesicular system having a central aqueous core. They have a hydrophilic inner core and lipophilic bilayer. They differ from nanoparticles in that they contain a hydrophilic core rather than a lipophilic core, as in the case of nanoparticles. Although they have a bilayer structure, they offer more stability than liposomes due to the presence of a thick and rigid bilayer. They contain a hydrophilic core that provides a protein-affable environment.

In some embodiments, the channels are inserted into polymer membranes in the presence of any detergents of various composition (e.g., DDM, DOC, Tween, SDS, and Brij based detergents). In some embodiments, the protein channels are reconstituted into polymersomes in the presence of varying amounts of glycerol, CsCl, and/or sucrose for high-efficiency fusion.

In some embodiments, the protein channel is reengineered by mutagenesis (e.g., containing one to several substitutions) to facilitate insertion in (planar) polymer membranes. In addition, the protein channel is reengineered to introduce functional sites for site-specific labeling with chemicals or biopolymers for the purpose of inserting in polymer membranes. Such functional sites include cysteine residues for conjugating chemicals, such as porphyrin, or biological molecules, such as cholesterol or any hydrophobic lipid modules or nucleic acids of various lengths. The functional sites/groups may also include non-natural amino acids and linkage created by well-established chemical methods, including but not limited to ester, click chemistry, and sulfhydryl.

In some embodiments, the location of the conjugation is in the membrane anchoring layer of the channel, such as residues 70-80, 110-140, 155-245, 300-340, 410-435 of T4 gp 20 portal protein; residues 10-45, 250-300 of P22 gp1 portal protein; and residues 130-170, 300-325, 350-390, 530-595 of phi29 gp9 tail protein. Accordingly, to increase or decrease the hydrophobicity of the belt region for the purpose of membrane insertion, reengineering may include mutagenesis (e.g., substitution, insertion, deletion) of any one of the residues 70-80, 110-140, 155-245, 300-340, 410-435 of T4 gp 20 portal protein; residues 450-500, 350-380 of P22 gp1 portal protein; and residues 130-170, 300-325, 350-390, 530-595 of phi29 gp9 tail protein.

In some embodiments, the location of the conjugation is in the cis- and trans-hydrophilic layers of the channel, such as residues 465-515, 285-305 of T4 gp 20 portal protein; residues 450-500, 350-380 of P22 gp1 portal protein; and residues 20-50, and 250-300 of phi29 gp9 tail protein. Accordingly, to increase or decrease the hydrophobicity of the belt region for the purpose of membrane insertion, reengineering may include mutagenesis (e.g., substitution, insertion, deletion) may include any of the residues 465-515, 285-305 of T4 gp 20 portal protein; residues 450-500, 350-380 of P22 gp1 portal protein; and residues 20-50, and 250-300 of phi29 gp9 tail protein.

IV. Devices and Kits Comprising Nanopore Assemblies

In another aspect, this disclosure also provides a kit and a detection apparatus for detecting an analyte. The kit may include the nanopore assembly as described, optionally a buffer, and optionally instructions for using the nanopore assembly.

The apparatus may include the nanopore assembly as described and a support for the nanopore assembly. The detection apparatus can further include electrodes embedded in the solid support. The electrodes can be used to monitor assembly of protein nanopores into membranes. The electrodes can also be used for data collection during analyte detection steps. Electrodes used for monitoring and detection need not be embedded in the support and can be provided, for example, in a separate application-specific integrated circuit (ASIC) chip.

As used herein, the term "support" refers to a rigid substrate that is insoluble in an aqueous liquid and incapable of passing a liquid absent an aperture. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful supports comprise modified silicon such as SiN membranes on a Si substrate. For some embodiments, supports are located within a flow cell apparatus or other vessels.

In some embodiments, nanopores are fabricated on substrates such as chips, disks, blocks, plates and the like. Such substrates can be made from a variety of materials including but not limited to silicon, glass, ceramic, germanium, polymers (e.g., polystyrene), and/or gallium arsenide. The substrates may or may not be etched, e.g., chips can be semiconductor chips.

In particular embodiments, a detection apparatus can include a reservoir in contact with the array of nanopores. The reservoir can contain electrodes located to apply a current through the apertures formed by the protein nanopores.

In some embodiments, the detection apparatus of the present disclosure may include (a) an electrode; (b) a nanopore tethered to the electrode; and (c) a membrane surrounding the nanopore. Multiplex embodiments are also provided. For example, a detection apparatus can include (a) a plurality of electrodes; (b) a plurality of nanopores, each of the nanopores tethered to an electrode in the plurality of electrodes; and (c) a membrane surrounding each of the nanopores.

A nanopore can be tethered to an electrode (e.g., via a dielectric pad) using covalent moieties or non-covalent binding moieties. An example of a covalent attachment is when a nucleic acid tether is covalently attached to the nanopore and covalently attached to the dielectric pad. Other tethers can be similarly used for covalent attachment, including, for example, non-nucleic acid tethers such as polyethylene glycol or other synthetic polymers. An example, of a non-covalent attachment, is when a nanopore has an attached affinity moiety, such as a polyhistidine tag, Strep-tag or other amino acid encoded affinity moiety. Affinity moieties can bind non-covalently to ligands on a dielectric pad such as nickel or other divalent cations that bind polyhistidine, or biotin (or analogs thereof) that bind to Strep-tag. In some embodiments, such amino acid affinity moieties need not be used.

As described herein, the nanopores (whether hybrid nanopores or tethered nanopores) can be coupled with a detection circuit, including, for example, a patch clamp circuit, a tunneling electrode circuit, or a transverse conductance measurement circuit (such as a graphene nanoribbon, or a graphene nanogap), to record the electrical signals in methods of the present disclosure. In addition, the pore can also be coupled with an optical sensor that detects labels, for example, a fluorescent moiety or a Raman signal generating moiety, on the polynucleotides.

A detection apparatus of the present disclosure can be used to detect any of a variety of analytes including, but not limited to, ions, nucleic acids, nucleotides, polypeptides, biologically active small molecules, lipids, sugars or the like. Accordingly, one or more of these analytes can be present in or passed through the aperture of a protein nanopore in an apparatus set forth herein.

Other detection techniques that can be applied to an apparatus set forth herein include, but are not limited to, detecting events, such as the motion of a molecule or a portion of that molecule, particularly where the molecule is DNA or an enzyme that binds DNA, such as a polymerase. For example, Olsen et al, JACS 135: 7855-7860 (2013), which is incorporated herein by reference, discloses bioconjugating single molecules of the Klenow fragment (KF) of DNA polymerase I into electronic nanocircuits so as to allow electrical recordings of enzymatic function and dynamic variability with the resolution of individual nucleotide incorporation events. Or, for example, Hurt et al., *JACS* 131: 3772-3778 (2009), which is incorporated herein by reference, discloses measuring the dwell time for complexes of DNA with the KF atop a nanopore in an applied electric field. Or, for example, Kim et al., *Sens. Actuators B Chem.* 177: 1075-1082 (2012), which is incorporated herein by reference, discloses using a current-measuring sensor in experiments involving DNA captured in an α-hemolysin nanopore. Or, for example, Garalde et al., *J. Biol. Chem.* 286: 14480-14492 (2011), which is incorporated herein by reference, discloses distinguishing KF-DNA complexes based on the basis of their properties when captured in an electric field atop an α-hemolysin pore. Other references that disclose measurements involving α-hemolysin include the following, all to Howorka et al., which are incorporated herein by reference: *PNAS* 98: 12996-13301 (2001); *Biophysical Journal* 83: 3202-3210 (2002); and *Nature Biotechnology* 19: 636-639 (2001).

In some embodiments, the invention relates to channel proteins assembled into a lipid bilayer membrane. The presence of an analyte is monitored by the ionic current that passes through the pore at a fixed applied potential with an interruption of current indicating interactions of the analyte with the channel protein. In some embodiments, a stabilized sensor chip contains a single protein nanopore protein. The protein nanopore sensor chip can be applied to measurements at the single-molecule level, i.e., stochastic sensing. By monitoring the ionic current that passes through the pore at a fixed applied potential, various analytes can be distinguished on the basis of the amplitude and duration of individual current-blocking events.

V. Methods For Detecting Analytes Using Nanopore Assemblies

In another aspect, the disclosure provides a method of detecting/sensing an analyte. The method includes: (1) contacting a sample containing an analyte with the nanopore assembly as described; (2) applying an electrical current across the channel of the nanopore assembly; (3) determining the electrical current passing through the channel at one or more time intervals; and (4) comparing the electrical current measured at one or more time intervals with a reference electrical current, wherein a change in electrical current relative to the reference electrical current indicates a presence of the analyte in the sample. In some embodiments, the reference electrical current is measured with a sample that does not contain the analyte. In some embodiments, the nanopore assembly is placed on a support.

In some embodiments, the method may include measuring the ion current and/or a change in current signature, induced by translocation of each unit of the analyte or polymer through the channel In some embodiments, the method may include measuring the ion current and/or a change in current signature, induced by transient or permanent binding of each unit of the analyte or polymer to probes coupled on the channel which cause a change in current signature.

The analyte that can be detected by the disclosed methods of the present disclosure may be any one of nucleic acids, amino acids, peptides, proteins, polymers, and chemical molecules. A nucleic acid detected in the methods can be single stranded, double stranded, or contain both single stranded and double stranded sequence. The nucleic acid molecules can originate in a double-stranded form (e.g., dsDNA) and can optionally be converted to a single-stranded form. The nucleic acid molecules can also originate in a single stranded form (e.g., ssDNA, ssRNA), and the ssDNA can optionally be converted into a double-stranded form.

VI. Definitions

To aid in understanding the detailed description of the compositions and methods according to the disclosure, a few express definitions are provided to facilitate an unambiguous disclosure of the various aspects of the disclosure.

Unless otherwise defined, all technical and scientific terms used herein have the same meaning as commonly understood by one of ordinary skill in the art to which this disclosure belongs.

It is noted here that, as used in this specification and the appended claims, the singular forms "a," "an," and "the" include plural reference unless the context clearly dictates otherwise. The terms "including," "comprising," "containing," or "having" and variations thereof are meant to encompass the items listed thereafter and equivalents thereof as well as additional subject matter unless otherwise noted.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the terms "nanopore" and "channel" are used to refer to structures having a nanoscale passageway through which ionic current can flow. The inner diameter of the nanopore may vary considerably depending on the intended use of the device. Typically, the channel or nanopore will have an inner diameter of at least about 0.5 nm, usually at least about 1 nm and more usually at least about 1.5 nm, where the diameter may be as great as 50 nm or longer, but in many embodiments will not exceed about 10 nm, and usually will not exceed about 2 nm.

As used herein, the term "analyte" refers to a substance or chemical constituent that is undergoing analysis or sought to be detected. It is not intended that the present invention be limited to a particular analyte. Representative analytes include ions, saccharides, proteins, nucleic acids, and nucleic acid sequences.

As used herein the term "membrane" refers to a sheet or other barrier that prevents passage of electrical current or fluids. The membrane is typically flexible or compressible in contrast to solid supports set forth herein. The membrane can be made from lipid material, for example, to form a lipid bilayer, or the membrane can be made from non-lipid material. The membrane can be in the form of a copolymer membrane, for example, formed by diblock polymers or triblock polymers, or in the form of a monolayer, for example, formed by a bolalipid. See, for example, Rakhmatullina et al., Langmuir: the ACS Journal of Surfaces and Colloids 24: 6254-6261 (2008), which is incorporated herein by reference.

As used herein, the term "lipid membrane" means a film made primarily of compounds comprising saturated or unsaturated, branched or unbranched, aromatic or non-aromatic, hydrocarbon groups. The film may be composed of multiple lipids. Examples of lipids include, but are not limited to, fatty acids, mono-, di-, and triglycerides, glycerophospholipids, sphingolipids, steroids, lipoproteins, and glycolipids.

"Nucleic acid" or "nucleic acid sequence" or "nucleic acid molecule" refers to deoxyribonucleotides or ribonucleotides and polymers thereof in either single- or double-stranded form. The term nucleic acid is used interchangeably with gene, complementary DNA (cDNA), messenger RNA (mRNA), oligonucleotide, and polynucleotide. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The terms encompass molecules formed from any of the known base analogs of DNA and RNA such as, but not limited to 4-acetylcytosine, 8-hydroxy-N6-methyladenine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions, in some aspects, are achieved by generating sequences in which the third position of one or more selected (or all) codons is substituted with mixed-base and/or deoxyinosine residues (Batzer et al., Nucleic Acid Res. 19: 5081, 1991; Ohtsuka et al., J. Biol. Chem. 260: 2605-8, 1985; Rossolini et al., Mol. Cell. Probes 8: 91-8, 1994). The term nucleic acid is used interchangeably with gene, cDNA, mRNA, oligonucleotide, and polynucleotide.

"Polypeptide" is used in its conventional meaning, i.e., as a sequence of amino acids. The polypeptides are not limited to a specific length of the product. Peptides, polypeptides, and proteins are included within the definition of polypeptide, and such terms can be used interchangeably herein unless specifically indicated otherwise. This term also includes post-expression modifications of the polypeptide, for example, glycosylations, acetylations, phosphorylations and the like, as well as other modifications known in the art, both naturally occurring and non-naturally occurring. A polypeptide can be an entire protein or a subsequence thereof.

The terms "identical" or percent "identity" as known in the art refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms"). "Substantial identity" refers to sequences with at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity over a specified sequence. In some aspects, the identity exists over a region that is at least about 50-100 amino acids or nucleotides in length. In other aspects, the identity exists over a region that is at least about 100-200 amino acids or nucleotides in length. In other aspects, the identity exists over a region that is at least about 200-500 amino acids or nucleotides in length. In certain aspects, percent sequence identity is determined using a computer program selected from the group consisting of GAP, BLASTP, BLASTN, FASTA, BLASTA, BLASTX, BestFit, and the Smith-Waterman algorithm.

The term "similarity" is a related concept but, in contrast to "identity," refers to a measure of similarity which includes both identical matches and conservative substitution matches. If two polypeptide sequences have, for example, $^{10}/_{20}$ identical amino acids, and the remainder are all non-conservative substitutions, then the percent identity and similarity would both be 50%. If, in the same example, there are five more positions where there are conservative substitutions, then the percent identity remains 50%, but the percent similarity would be 75% ($^{15}/_{20}$). Therefore, in cases where there are conservative substitutions, the degree of percent similarity between two polypeptides will be higher than the percent identity between those two polypeptides.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as about 1% to 50%, it is intended that values such as 2% to 40%, 10% to 30%, or 1% to 3%, etc., are expressly enumerated in this specification. The values listed above are only examples of what is specifically intended.

Ranges, in various aspects, are expressed herein as from "about" or "approximately" one particular value and/or to "about" or "approximately" another particular value. When values are expressed as approximations, by use of the antecedent "about," it will be understood that some amount of variation is included in the range.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, the term "purified" or "substantially purified," as used herein, refers to the desired protein is enriched by at least 20%, more preferably by at least 50%, even more preferably by at least 75%, and most preferably by at least 90%, or even 95%.

Each publication, patent application, patent, and other reference cited herein is incorporated by reference in its entirety to the extent that it is not inconsistent with the present disclosure.

Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

Recitation of ranges of values herein are merely intended to serve as a shorthand method for referring individually to each separate value falling within the range and each end-point unless otherwise indicated herein, and each separate value and endpoint is incorporated into the specification as if it were individually recited herein.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

The section headings as used herein are for organizational purposes only and are not to be construed as limiting the subject matter described.

It is understood that the examples and embodiments described herein are for illustrative purposes only and that various modifications or changes in light thereof will be suggested to persons skilled in the art and are to be included within the spirit and purview of this application and scope of the appended claims.

VII. EXAMPLES

Example 1

This example describes the materials and methods to be used in the subsequent examples.

Material and Methods

Non-Membrane Protein Channel Reconstruction

For a non-membrane protein channel, it is difficult to insert into lipid bilayer or polymer membrane directly because unlike membrane protein channels, they usually lack hydrophobic layer in the middle and hydrophilic layers in both ends and hence require extensive engineering. In order to be used for biosensing, or sequencing, non-membrane protein channel also need to be engineered and functionalized with different probes. Although non-membrane protein channel may originate from various source with different sequences, shapes, structures, or properties, the strategies and methods employed to reengineer and enable them to be used as nanopore share some common feature. As shown in FIGS. 1A and 1B, three distinct domains are important for membrane anchoring, and two areas are particularly important for conjugation of functional modules for single molecule sensing. To reengineer these distinct domains and change the hydrophobic or hydrophilic property, or functionalized conjugation site or probes, a series of molecular cloning works are involved. Typically, a common restriction enzyme cloning method is employed for various engineering purposes. However, other clone methods, such as Gateway® Recombination Cloning, TOPO® Cloning, Isothermal Assembly Reaction, or Type IIS Assembly could also be employed.

Expression and Purification of Non-Membrane Proteins

Although non-membrane protein channel may originate from various source with different sequences, shapes, structures, or properties, the strategies and methods employed to express and purify them share some common features.

First, the reengineered non-membrane protein channel gene was cloned into an expression vector with or without a tag on the terminal. Then the vector was transformed into suitable protein expression host, e.g., E. coli system. After the protein channel was expressed in the host, the host was lysed and series of steps were taken to remove the host debris Finally, non-membrane proteins could be purified by one or combination of following methods, such as affinity chromatography, exchange chromatography, size exclusion chromatography, or other commonly used purification methods.

As an example, the non-membrane protein channel gene and variants gene was cloned into a PET23a vector with His-tag at the N-terminus. After transforming into BL21 (DE3) cells, one BL21(DE3) colony was inoculated in 5 mL fresh LB medium in the presence of antibiotics and cultured at 37° C. in a shaker for several hours until the OD reached 0.8. The flask was then kept at 4° C. for cooling down. Then 0.5 mM IPTG was added into the flask for induction. The bacteria were cultured at 16° C. in a shaker overnight. The bacteria were harvested in 8000 rpm for 10 mins, supernatant discarded, and then the pellet suspended with lysis buffer. The bacteria solution was sonicated until the solution became transparent and not sticky. The solution was centrifuged after sonicating with 12000 rpm for 30 mins, the supernatant discarded and the pellet collected. 10 ml urea (8 M) was added to the precipitation and oscillated at low speed on the oscillator until the precipitation was completely dissolved in urea. The solution was centrifuged at 12000 rpm for 10 mins The supernatant was added to 100 ml protein renaturation buffer and stirred overnight. The solution was centrifuged after refolding at 12000 rpm for 30 mins, the pellet discarded and the supernatant collected. The supernatant was passed through 0.45 um syringe filter to discard the denatured protein. The supernatant was added to a dialysis bag, and the dialysis fluid replaced three times. The fluid in the dialysis bag is collected and centrifuges for 12000 rpm for 10 minutes, the pellet discarded and the supernatant collected. Nickel beads were equilibrated with lysis buffer, and the supernatant added to the beads. The beads were then washed with washing buffer. The protein was eluted using elution buffer for 7~10 column volumes. The eluent was collected and concentrated to 5 mL. The eluent was centrifuged at 12000 rpm for 10 mins, and then the supernatant was absorbed and injected with a syringe into AKTA FPLC. Before injection, the sample loop was washed with 10 mL lysis buffer. The protein was collected after passing through a size exclusion column. An SDS-PAGE gel was run to check the protein sample after SEC, and stored at −80° C.

Conjugation

To functionalized with different probes or enhance the hydrophobicity or hydrophilicity of non-membrane protein channels, various conjugation methods could be employed. Although non-membrane protein channel may originate from various source with different sequences, shapes, structures, or properties, the strategies and methods employed for conjugation share some common feature. To conjugate a hydrophobic moiety to non-membrane protein channel, the reactions could be done on cysteine group on the protein channel The protein channel contains one or multiple cysteines per subunit, which are located in the middle layer of the channel and accessible to the environment. The protein solution was prepared in a buffer containing 0.5 M NaCl, 50 mM Tris, 15% glycerol with pH 6.8. The solution was degassed, and 100-fold excess TCEP was added to the solution. After 20 min incubation at room temperature, 4 µL of 4 mM cholesterol-PEG-maleimide was added drop-wise to the protein solution, and the reaction mixture was incubated in the dark at room temperature for 2 hours. Excess cholesterol-PEG-maleimide was removed by a NanoSep 100K spin column. The labeling of the protein was checked with 12% SDS-PAGE.

To conjugate probes to non-membrane protein channel, click chemistry, such as Tetrazine-Alkene ligation, or Azide-Alkyne click chemistry is employed. For Tetrazine-Alkene ligation, the protein solution was prepared in a buffer containing 0.5 M NaCl, 50 mM Tris, 15% glycerol with pH 6.8. The solution was degassed, and 100-fold excess TCEP was added to the solution. After 20 min incubation, 1.6 µL of 10 mM Methyltetrazine-PEG4-maleimide was added drop-wise to the protein solution, and the mixture was incubated in the dark at room temperature for 1 hour. Excess Methyltetrazine-PEG4-maleimide was removed by desalting using a desalt spin column. A 50 µL of probe solution was prepared in a buffer containing 0.5 M NaCl, 50 mM Tris with pH 6.8. The solution was degassed, and 100-fold excess TCEP was added to the solution. After 20 min incubation, 6 µL of 25 mM TCO-PEG3-maleimide was added drop-wise to the oligo solution, and the mixture was incubated at room temperature for 2 hours. Excess TCO-PEG3-maleimide was removed by desalting column. The labeling of the probe was verified by 20% urea-PAGE gel.

For Azide-Alkyne ligation, TCO-modified probe was mixed with Methyltetrazine-labeled protein at different molar ratios to achieve optimal protein labeling efficiency. The mixture was incubated at room temperature for 1 hour. The conjugation was verified with 12% SDS-PAGE. To A 40 µL of 20 µM protein solution was prepared in a buffer containing 0.5 M NaCl, 50mM Tris, 15% glycerol with pH 6.8. The solution was degassed, and 100-fold excess TCEP was added to the solution. After 20 min incubation, 1.6 µL of 10 mM Sulfo DBCO-PEG4-maleimide was added drop-wise to the protein solution, and the mixture was incubated in the dark at room temperature for 1 hour. Excess maleimide reagent was removed by desalting using a desalt spin column. The DBCO-modified protein was mixed with Azide-modified probe at equal molar concentration, and the reaction mixture was incubated at room temperature for 2 hours. The conjugation was verified with 12% SDS-PAGE gel.

Nanopore Experiments Setup and Data Recording

Although non-membrane protein channel may originate from various source with different sequences, shapes, structures, or properties, all non-membrane protein channels or variants could be applied on the similar nanopore setup or device. Typically, the setup comprises a sensor chip or array which have one or multiple apertures. The sensor chip is capable of supporting lipid or polymer membrane formation which could separate the compartment into cis-(top) and trans-(bottom) compartments. Both compartments were filled with conducting buffer. Input electrode was embedded into one of the compartment, and a ground electrode was embedded into another compartment. Furthermore, the setup maybe also combined with a fluidic system to enable sample flow from one container to the sensor device. To insert non-membrane protein channel into lipid or polymer membrane, the protein channel was suspended in their respective storage buffer is diluted 50-100 fold in the conducting buffer (typically 1 M KCl or 1 M NaCl, 5 mM HEPES or Tris, pH 7.6) and added to the top compartments. Under an applied potential (constant holding voltage or ramping voltage) with or without detergent, direct insertion of the protein channels in planar membranes can be observed. When no analyte presents, the current is stable and clean. When the analyte presents, the interaction with probe results in a current change which was recorded.

Data Analysis

Although non-membrane protein channel may originate from various source with different sequences, shapes, structures, or properties, the strategies and methods employed for data analysis share common feature. Typically, ~10,000+ current blockage events (either translocation or single molecule binding events) are analyzed to ensure the result is within statistical significance. MATLAB or PYTHON-based custom algorithm was developed for quantitative fast processing of events. Generally, two parameters are used: (1) Current blockage fraction, represented as [(Current$_{unblocked}$−Current$_{after\ analyte\ block}$)/Current$_{unblocked}$]; and (2) Dwell time: $\tau_{off}$ (duration of an event) and $\tau_{on}$ (time between consecutive events). From the $\tau_{on}$ and $\tau_{off}$, the $\kappa_{on}$ (association rate constant) and $\kappa_{off}$ (dissociation rate constant) can be obtained and finally $K_d$ (equilibrium dissociation constant). A calibration curve was constructed showing the capture rate as a function of analyte concentration. Upon introducing an unknown concentration of the analyte to the nanopore, the mean capture rate can be calculated, and the analyte concentration can be determined from the calibration curve. Analysis of clinical samples requires further tuning of the analysis algorithm to clearly discriminate between 'contaminative' or non-specific signals and true analyte induced events. To standardize the analyte detection system, an 'endogenous' normalizer with a 'spiked-in' control was generally employed. The platform data was then cross-validated using standard assays commonly used in the diagnostic field, such as immunoassay and qRT-PCR. Finally, statistical sample size/power analyses were based on two-sample t-tests for two-group comparisons and two-way analysis of variance (ANOVA) for a combination of two factors.

Example 2

Expression and Purification of the phi29 gp-9 Tail
Protein

Figure 4:
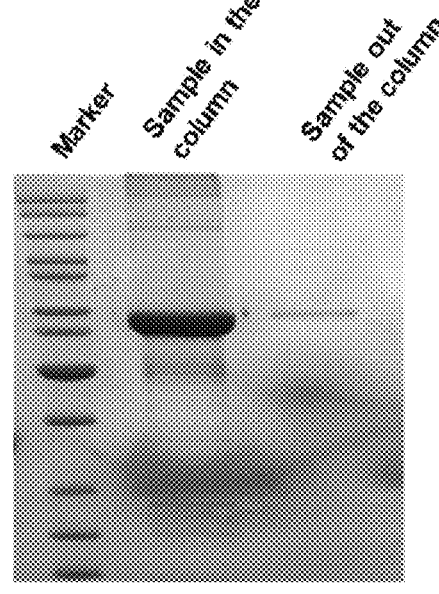
FIG. 4 is an example Coomassie-blue stained SDS-PAGE gel showing that majority of the gp-9 tail protein channel is present in 100 kDa column after purification and assembly, indicating that the channel is assembled from its monomer units, which are ~70kDa.
Figure 5:
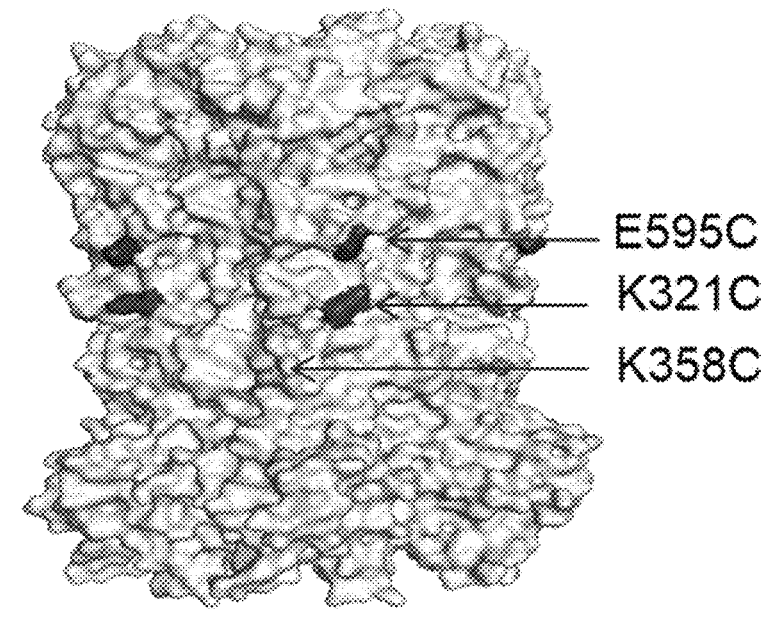
FIG. 5 is an example of target sites selection in the non-membrane protein surface, as demonstrated using the phi29 gp9 tail protein. Phi29 gp9 tail protein structure shows three possible residues for mutagenesis into cysteine for conjugating hydrophobic membrane-anchoring modules.
Figure 6:
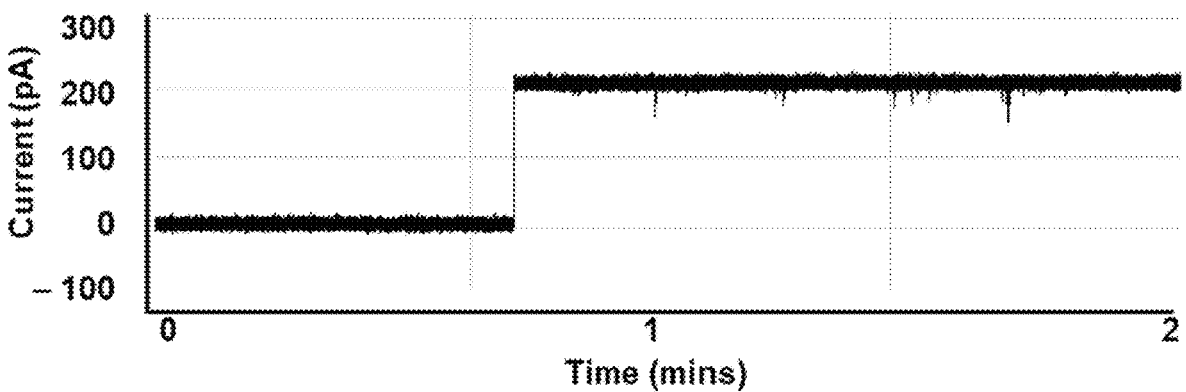
FIG. 6 shows an example of non-membrane protein channel inserted into polymer membranes, as demonstrated using the phi29 gp9ΔLoop tail protein. Single channel recording data shows direct insertion of the phi29 gp9ΔLoop channel into a polymer membrane of composition $PMOXA_6$-$PDMS_{65}$-$PMOXA_6$. Conduction buffer: 1 M NaCl, 5 mM Tris, pH 7.6. Applied voltage: 75 mV.
Figures 7A, 7B:
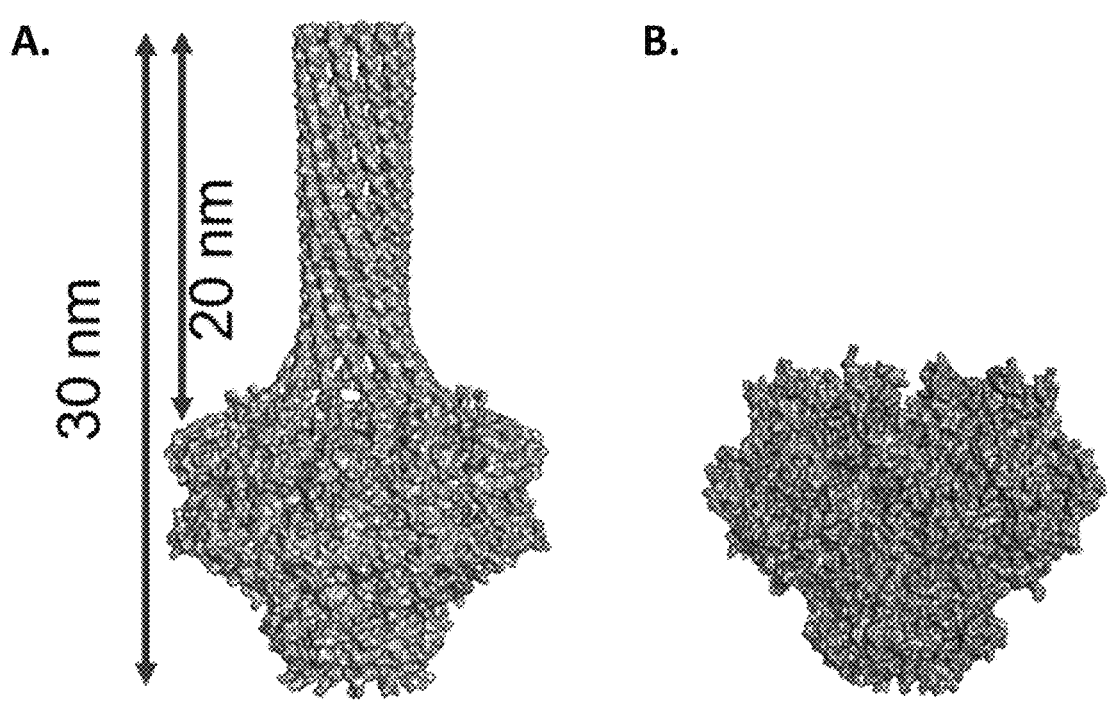
FIGS. 7A and 7B show the structure of bacteriophage P22 gp1 portal protein full length (FIG. 7A) and barrel-deleted mutant (FIG. 7B).
Figure 8:
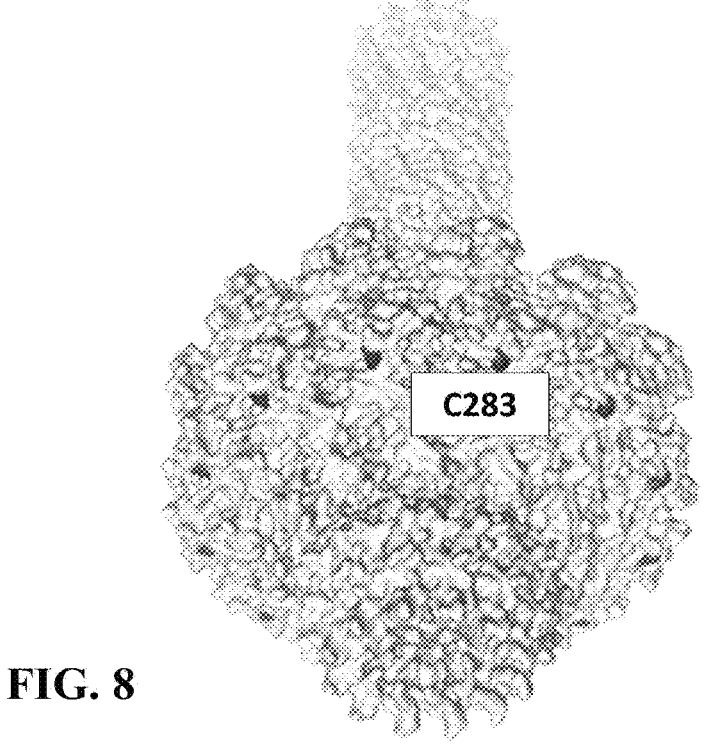
FIG. 8 shows an example of target sites selection in the non-membrane proteins for membrane anchorage, as demonstrated using P22 gp1 portal protein. A representative conjugation site (e.g., an accessible cysteine residue, C283) for incorporating membrane anchoring domain is shown on the structure of bacteriophage P22 gp1 portal protein.
Figure 9:
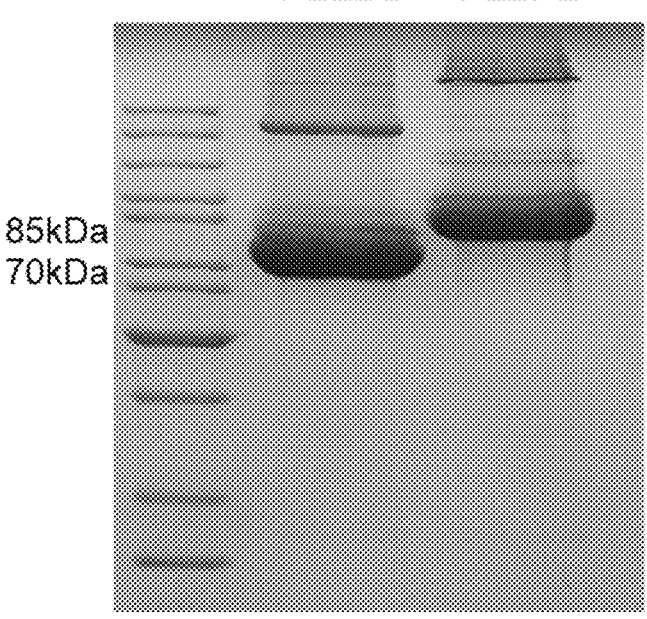
FIG. 9 shows an example of non-membrane proteins pores functionalized with fused peptide probes, as demonstrated using P22 gp1 portal protein fused with VCAM1. Coomassie-blue stained gel shows purified bacteriophage P22 gp1 portal protein full length and barrel deleted mutants with VCAM1 probe fused at the C-terminus.
Figure 10:
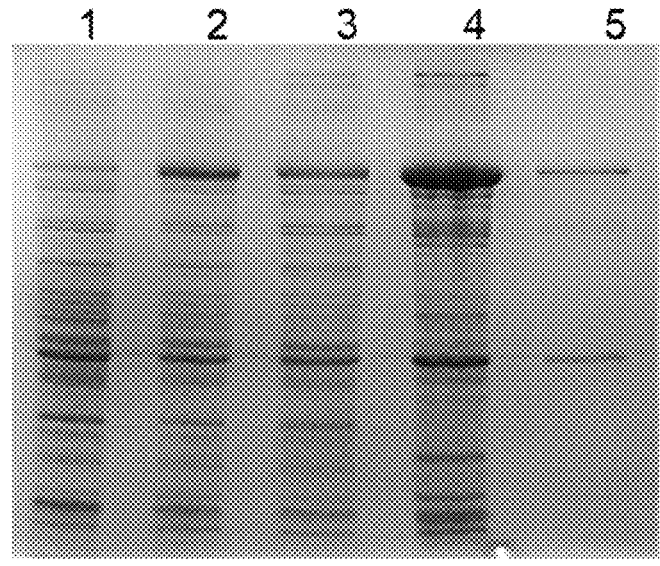
FIG. 10 shows an example of non-membrane proteins pores functionalized with fused peptide probes, as demonstrated using P22 gp1 portal protein fused with PSA. Coomassie-blue stained gel shows purified bacteriophage P22 gp1 portal protein barrel deleted mutant with PSA probe fused at the C-terminus.
Figure 11:
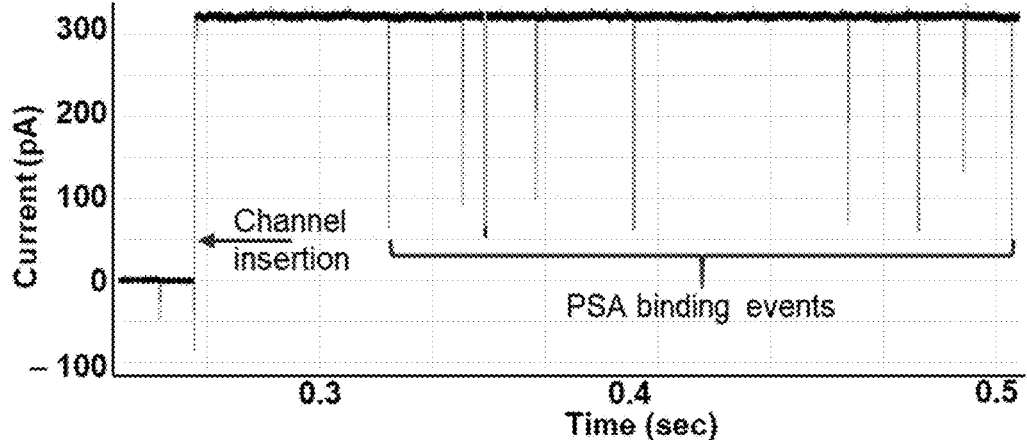
FIG. 11 shows an example of non-membrane proteins pores functionalized with fused peptide probes for single molecule sensing, as demonstrated using P22 gp1 portal protein fused with PSA probes for detecting PSA. Single channel recording data shows direct insertion of P22 gp1 protein channel harboring fused PSA probe into the polymer membrane of composition PMOXA6-PDMS35-PMOXA6. In the presence of PSA (10 ng/uL), the probe binds to the PSA and results in the characteristic current blockage events. Conduction buffer: 1 M KCl, 5 mM Tris, pH 7.6. Applied voltage: 75 mV.
Figure 12:
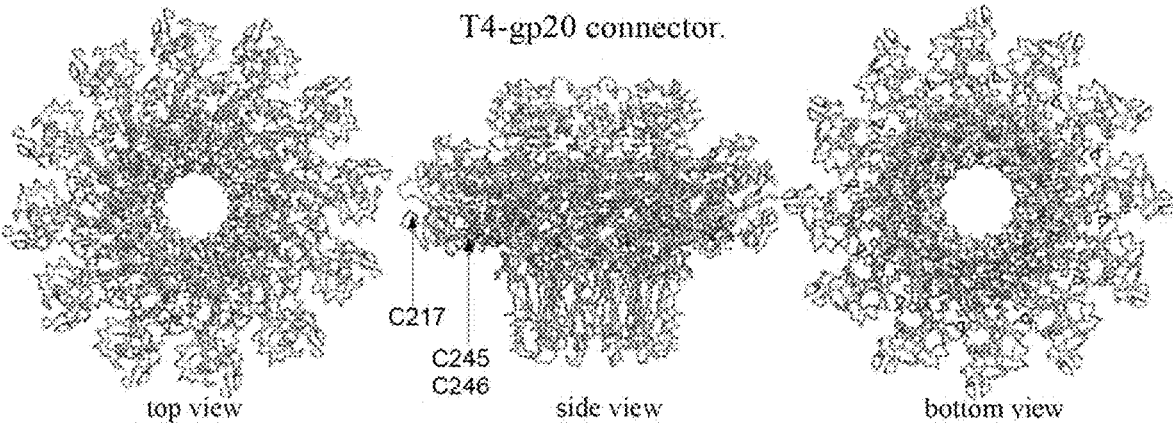
FIG. 12 shows an example of target sites selection in the non-membrane proteins for membrane anchorage, as demonstrated using T4 gp20 portal protein. Representative conjugation sites (e.g., via accessible cysteine residues, C217, 245, 246) for incorporating membrane anchoring domain are indicated on the structure of bacteriophage T4 gp20 portal protein.

The purified phi29 gp-9 tail protein and its variants in
SDS PAGE are shown in FIGS. 3-4. The expression and
purification steps are as follows. The phi29 gp-9 tail protein
gene and variants gene was cloned into vector pBDHT with
His-tag on the N-terminal After transforming into BL21
(DE3), one BL21 colony was inoculated in 5 mL fresh LB
medium with antibiotic inside, cultured at 37° C. in a shaker
(220 rpm) for several hours until the OD reached 0.8. The
flask was then kept at 4° C. for cooling down. Then 0.5 mM
IPTG was added into the flask for induction. The bacteria
were cultured at 16° C. in a shaker (180 rpm) overnight. The
bacteria were harvested in 8000 rpm for 10 mins, superna-
tant discarded, and then the pellet resuspended with lysis
buffer (50 mM Tris pH8.0, 500 mM NaCl). The bacteria
solution was sonicated until the solution becomes transpar-
ent and not sticky. The solution was centrifuged after
sonicating with 12000 rpm for 30 mins, the supernatant
discarded and the pellet collected. 10 ml urea (8 M) was
added to the precipitation and oscillated at low speed on the
oscillator until the precipitation was completely dissolved in
urea. The solution was centrifuged at 12000 rpm for 10 mins
The supernatant was added to 100 ml protein renaturation
buffer (15% glycerol, 500 mM NaCl, 50 mM Tris, 2 M
L-Arginine, pH8.0) and stirred overnight. The solution was
centrifuged after refolding at 12000 rpm for 30 mins, the
pellet discarded and the supernatant collected. The super-
natant was passed through 0.45 um syringe filter to discard
the denatured protein. The supernatant was added to a
dialysis bag, and the dialysis fluid (50 mM NaCl, 5 mM Tris)
replaced three times. The fluid in the dialysis bag is collected
and centrifuges for 12000 rpm for 10 minutes, the pellet
discarded and the supernatant collected. Nickel beads were
equilibrated with lysis buffer, and the supernatant added to
the beads. The beads were washed with washing buffer (50
mM Tris pH8.0, 500 mM NaCl, 25 mM imidazole) for 50
column volumes. The protein was eluted using elution buffer
(50 mM Tris pH8.0, 500 mM NaCl, 500 mM imidazole) for
7~10 column volumes. The elution was collected and con-
centrated to 5 mL. The elution was centrifuged at 12000 rpm
for 10 mins, and then the supernatant was absorbed and
injected with a syringe into AKTA FPLC. Before injection,
the sample loop was washed with 10 mL lysis buffer. The
protein was collected after passing through a size exclusion
column. An SDS-PAGE gel was run to check the protein
sample after SEC, and stored at –80° C.

Example 3

Phage Tail Proteins as Nanopores

Many bacteriophages contain a long contractile or non-
contractile, or short non-contractile tail. The tail plays a
critical role in the process of host cell recognition, mem-
brane penetration, and viral genome ejection. The tail pro-
teins are derived from (including but not limited to) phi29,
T4, T3, T5, T7, SPP1, P22, P2, P3, Lambda, Mu, HK97 and
C1.

These protein channels of the invention are ideal for
biosensing and sequencing of a biological molecule, such as
disease-related biomarker, polynucleotide and polypeptide
sequences. With improved membrane capability, the modi-
fied protein channels could insert into lipid or polymer membrane efficiently and serve as nanopore for biosensing
and sequencing. By conjugating with various probes, the
modified protein channels have the capacity to detect spe-
cific disease-related biomarker with high sensitivity and
specificity. The pore of the invention may be present in a
homologous or heterologous pore.

Representative Example: Gp-9 Tail Protein From
phi29

The crystal structure of phi29 bacteriophage tail (gp9)
shows that six gp9 subunits form a hexameric or cylindrical-
like tube structure. Inside the structure, the distal end is
blocked by six flexible hydrophobic loops before DNA
ejection is triggered. In order to deliver the genomic dsDNA
into the host cell cytoplasm, the phi29 tail needs to penetrate
the cell membrane. The length of the tube is about 12.5 nm.
The tube has an inner diameter of approximately 4 nm and
an outer diameter of approximately 9 nm and. The wall of
the tube is comprised of largely β-sheets with about 2.5 nm
thickness.

A clone of full-length gp9 and series of mutants were
constructed (FIGS. 2-6), such as gp9Δloop[417-491], in
which a disordered region (residues 417-491) was deleted.
According to the crystal structure, the gp9Δ 417-491 struc-
ture is also a cylindrical tube-like homo-hexamer. By study-
ing the structure of the tail protein, the amino acids 130-
170,300-325,350-390,530-595 is on the surface of the
middle channel, which can interact with the hydrophobic
layer of the membrane. Thus, attachment of a hydrophobic
group to these sites or mutation of these amino acids to
hydrophobic amino acids, including glycine (Gly), alanine
(Ala), valine (Val), leucine (Leu), isoleucine (Ile), proline
(Pro), phenylalanine (Phe), methionine (Met), and trypto-
phan (Trp), could change the channel's capability of mem-
brane insertion. Particularly, mutations of one or any com-
bination of the following sites are critical: K134I, D138L,
D139L, D158L, E163V, E309V, D311V, K321V, K356A,
K358A, D377A, D381V, N388L, R524I, R539A, E595V. To
conjugate a hydrophobic group to the middle part of the
channel, mutation of the following sites to cysteine are
important: E595C, K321C, and K358C. In addition, the
amino acids 250-300, and 20-50 are laying on the surface of
the upper and lower part of the channel, which can interact
with the hydrophilic environment.

Viral Portal Proteins as Nanopores

Portal proteins exist not only in bacteriophages phi29, T3,
T4, T5, T7, SPP1, and P22, but also in other viral systems
such as Adeno and Herpes viruses. The portal channel,
termed the connector, is a pore-like protein structure with a
central channel that acts as a pathway for genomic DNA to
enter the viral capsid during packaging and exit during
infections. Although structural studies indicate significant
differences in sequence homology and sizes among different
viral connector proteins, they all are topologically similar
with a truncated cone shape. The stoichiometry of the
connectors derived from overexpressed proteins often varies
depending on the expression conditions. These protein chan-
nels of the invention can be ideal for biosensing and
sequencing applications if they can be directly inserted into
robust polymer membranes. Since the structures of the
connector from different viral portal proteins show similar
characteristics, the principle outlined above also applies to
all of them by extension.

Representative Example: P22 Portal Channel

P22 is a tailed bacteriophage which assembles empty precursor capsids that are subsequently packaged with viral DNA by a powerful packaging motor. P22 portal protein forms a channel-like structure for bidirectional passage of viral DNA. Podoviridae family of short-tailed dsDNA bacteriophages includes members of the P22-like subgroup, such as Sf6, CUS-3, epsilon34, and APSE-1. The portal barrel is highly dynamic and susceptible to proteolysis in solution. The P22 portal protein is composed of 12 identical subunits, arranged symmetrically around the central channel. The overall height is ~30 nm with a funnel-shaped core of diameter ~17 mm, which is connected to an ~20 nm long α-helical tube. The average internal diameter of the channel varies from 3.5 nm to 7.5 nm throughout the structure.

Series of mutants were constructed (FIGS. 7-11), which include the following defining features: (1) The portal core (res. 1-602) is topologically similar to other viral protein channels, but the presence of the helical barrel tube is unique to P22. The connection between the portal core and helical barrel can be easily cleaved by chymotrypsin in solution, which indicates that the two domains are intrinsically flexible. The invention includes removal of the barrel residues 603-725 and replacement with any peptide or nucleic acid sequences as a separate recognition domain. (2) The invention includes alteration (deletion, truncation, mutation) of the internal flexible loop residues 464-492 to change the electrophysiological properties and/or detection capabilities. (3) The invention includes the use of EDTA (60 mM or higher) to assemble the dodecamer complex: Chelating divalent cations nonspecifically trapped at the monomer-monomer interface is necessary for correct assembly of dodecameric rings. (4) The invention includes changing the overall electronegative property of the channel interiors by altering the five rings of residues Glu70 (which is clustered together with Glu423, Glu414, Glu406, Glu393, and Glu396. (5) The invention includes altering any of the hydrophobic amino acids forming a belt underneath the wing domain (Phe 24, Ile25, Leu28, Phe60, Phe128, Pro129, and Pro132) to change the hydrophobicity of the surface; (6) The invention includes adding several amino acids (any natural or unnatural amino acids) at the terminal ends with the goal of using these amino acids as anchoring point (such as cysteine or lysine or arginine) for added functionalities or for altering the electrophysiological properties (hydrophilic or hydrophobic tag) for membrane insertion and channel stability; (7) The invention includes mutagenesis for hydrophobic and hydrophilic layer; Middle part: Amino acid from 250 to 300, 10-45; Upper part: 450-500; Lower part : 350-380; Arg 476 or C-terminal to Cys mutation for conjugation; Middle part THR240, VAL244, Arg 273 for Cys mutagenesis to conjugate cholesterol.

Representative Example: T4 Portal Channel

The T4 portal mostly exists as a 12-mer (some 11-mer or 13-mer depending on protein expression conditions) ring that is 14 nm long with 7 nm wide, and an interior channel of 3 nm in diameter. Since the channel assembles from 12 subunits, altering residue(s) in one monomer will trigger the effect in the entire channel with the mutation present in the same plane of the molecule. The invention includes (FIGS. 12-14, and 16): (1) changing the overall electronegative property of the channel interiors by altering the rings of charged residues; (2) altering the two basic residues, R338 and K342, at the inner channel entrance (with any amino acids to change the hydrophilicity; (3) Adding several amino acids (any natural or unnatural amino acids) at the terminal ends with the goal of using these amino acids as anchoring point (such as cysteine or lysine or arginine) for added functionalities or for altering the electrophysiological properties (hydrophilic or hydrophobic tag) for membrane insertion and channel stability; and (5) alteration (deletion, truncation, mutation) of the internal flexible loop residues 374-398 to change the electrophysiological properties and/or detection capabilities.

Example 4

Compositions of Membranes for Nanopore Housing

Planar bilayer lipid membranes (BLMs) or polymer membrane were generated in (a) BCH-1A horizontal BLM cell (Eastern Scientific) or (b) home-made custom chamber. A Teflon partition with a 100 or 200 μm aperture was placed in the apparatus to separate the BLM cell into cis-(top) and trans-(bottom) compartments. The home-made chamber has pre-drilled 100 or 200 um apertures separating the cis- and trans-compartments.

Lipid membrane: A planar lipid bilayer of varying composition was formed by pre-painting the aperture with lipids in hexane (concentration: 0.5 mg/ml) followed by painting with lipids in n-decane (concentration: 20-30 mg/ml). Examples of lipid composition include: (i) zwitterionic lipids such as 100% DPhPC or DOPC or POPC; (ii) 0-50% anionic lipids such as DPhPG/DOPG/POPG or DPhPS/DOPS/POPS mixed proportionately (final ratio adds up to 100%) with composition (i); (iii) 0-25% cholesterol mixed with composition (i) and (ii) proportionately. The exact lipid composition depends on the properties of the protein. Typical lipid membrane composition used include: 100% DPhPC; 100% DPhPC; 30% DPhPS; 70% DPhPC: 28% DPhPG: 2% cholesterol.

Polymer membrane: A planar polymer membrane of varying composition was formed by manual painting using membranes suspended in organic solvents such as Decane or Silicone oil (Polyphenyl-methylsiloxane based or Polydimethylsiloxane based with a viscosity of 20 mPa·s). The membrane composition is Polyoxazoline based triblock copolymers (FIG. 17) such as:

(i) PEOXA-PEO-PEOXA [Poly(2-ethyl oxazoline)-b-poly(ethylene oxide)-b-poly(2-ethyl oxazoline)];
  (ii) PMOXA-PDMS-PMOXA [Poly(2-methyl oxazoline)-b-poly(dimethylsiloxane)-b-poly(2-methyl oxazoline)]; (with ethyl-benzyl or propyl or propyl-ethoxy link between blocks)
  (iii) PMOXA-PB-PMOXA [Poly(2-methyl oxazoline)-b-poly(1,4-butadiene)-b-poly(2-methyl oxazoline)];
  (iv) PMOXA-PE-PMOXA [Poly(2-methyl oxazoline)-b-poly(ethylene)-b-poly(2-methyl oxazoline)];
  (v) PMOXA-PEO-PMOXA [Poly(2-methyl oxazoline)-b-poly(ethylene oxide)-b-poly(2-methyl oxazoline)]

Typical membranes used include PMOXA6-PDMS35-PMOXA6; PMOXA6-PDMS65-PMOXA6; PMOXA11-PDMS65-PMOXA11; PMOXA5-PDMS13-PMOXA5; PMOXA3-PDMS38-PMOXA3 (FIG. 17). The block lengths (denoted by subscripts X and Y in PMOXAX-PDMSY-PMOXAX) (which determines the length of hydrophilic or hydrophobic blocks) is tunable depending on the following factors: (1) certain membrane thickness is needed for stable insertion of the protein pore; (2) membranes need to retain very low permeability; (3) membrane has to be mechanically and chemically stable for an extended period of time under different solution conditions, including extreme pH (1-12) and high/low salt environments.

Example 5

Insertion of Protein Channels in the Membrane

Typically, the protein channels (tail proteins or portal channels) suspended in their respective storage buffer is diluted 50-100 fold in the conducting buffer (typically 1 M KCl or 1 M NaCl, 5 mM HEPES or Tris, pH 7.6) and added to the top compartments of the BLM cell. Under an applied potential (constant holding voltage or ramping voltage), direct insertion of the protein channels in planar membranes can be observed (FIGS. 6, 11, 14, 16, and 19).

If necessary, the membrane compositions as described can also be used to generate vesicular polymersome structures with varying polydispersity to reconstitute the protein channels. For high insertion efficiency, varying amounts of glycerol, CsCl, and/or sucrose can be encapsulated within the polymersomes. The resulting proteo-polymersomes can then fuse with a planar bilayer of the same composition in a salt and voltage-dependent manner

Example 6

Figure 13:
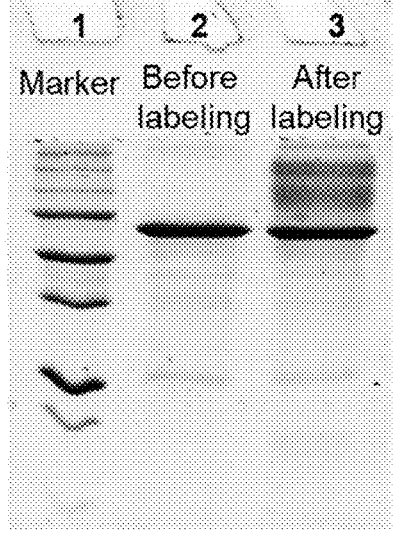
FIG. 13 shows an example of labeling non-membrane protein channels with cholesterol-PEG-maleimide for membrane anchorage, as demonstrated using T4 gp20 portal protein.

Conjugation of Hydrophobic Moieties to Non-Membrane Protein Channels Via Reactions With Cysteine Residues Here T4 gp20 portal protein is used as an example to demonstrate how to conjugate hydrophobic moiety to the non-membrane channel via reactions with cysteine residues. The protein channel contains three cysteines per subunit, which are located in the middle layer of the channel and accessible to the environment (FIG. 13). A 40 μL of 20 μM protein solution was prepared in a buffer containing 0.5 M NaCl, 50 mM Tris, 15% glycerol with pH 6.8. The solution was degassed, and 100-fold excess TCEP was added to the solution. After 20 min incubation at room temperature, 4 μL of 4 mM cholesterol-PEG-maleimide was added drop-wise to the protein solution, and the reaction mixture was incubated in the dark at room temperature for 2 hours. Excess cholesterol-PEG-maleimide was removed by a NanoSep 100K spin column. The labeling of the protein was checked with 12% SDS-PAGE (FIG. 13).

Example 7

Figure 14:
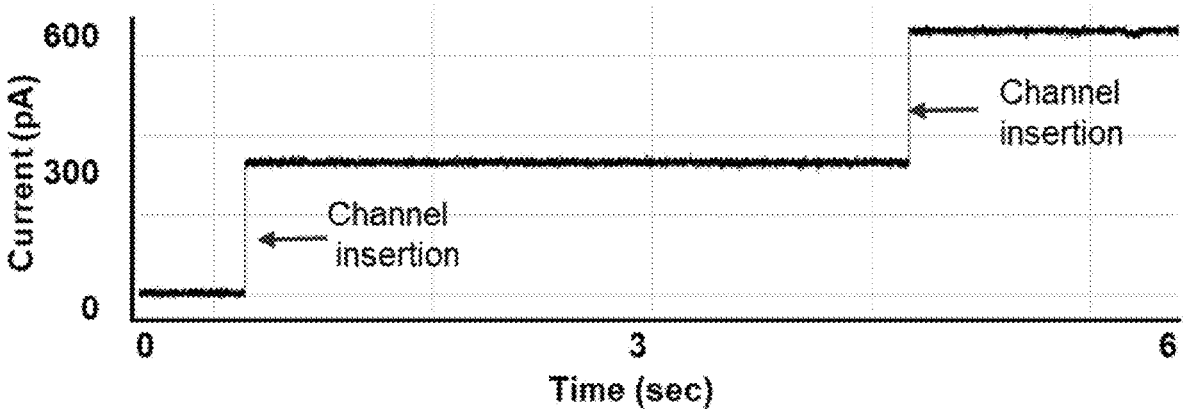
FIG. 14 shows an example of non-membrane protein channels inserted in polymer membranes, as demonstrated using T4 gp20 portal protein harboring cholesterol. Stepwise direct insertion of the proteins was observed under an applied potential. Conduction buffer: 1 M KCl, 5 mM Tris, pH 7.6. Applied voltage: 100 mV. Membrane: PMOXA6-PDMS35-PMOXA6.

Insertion of Non-Membrane Protein Channel Carrying Hydrophobic Moiety Into Lipid or Polymer Membrane Planar polymer membranes were generated. Under an applied voltage (constant holding voltage or ramping voltage), direct insertion of non-membrane protein channel carrying hydrophobic moiety was observed after adding protein channel to a cis chamber (FIG. 14). Mutation to hydrophobic amino acids or conjugation of hydrophobic group to the middle layer phi29 gp-9 tail protein can significantly enhance the insertion process and its stability.

Example 8

Conjugate Probes to Non-Membrane Protein Channels Via Click Reaction phi29 gp10 portal protein was used as a representative example.

Strategy 1: via Tetrazine-Alkene ligation: A 40 μL of 20 μM protein solution was prepared in a buffer containing 0.5

M NaCl, 50 mM Tris, 15% glycerol with pH 6.8. The solution was degassed, and 100-fold excess TCEP was added to the solution. After 20 min incubation, 1.6 μL of 10 mM Methyltetrazine-PEG4-maleimide was added drop-wise to the protein solution, and the mixture was incubated in the dark at room temperature for 1 hour. Excess Methyltetrazine-PEG4-maleimide was removed by desalting using a desalt spin column. A 50 μL of 30 μM thiol modified miRNA probe solution was prepared in a buffer containing 0.5 M NaCl, 50 mM Tris with pH 6.8. The solution was degassed, and 100-fold excess TCEP was added to the solution. After 20 min incubation, 6 μL of 25 mM TCO-PEG3-maleimide was added drop-wise to the oligo solution, and the mixture was incubated at room temperature for 2 hours. Excess TCO-PEG3-maleimide was removed by desalting column. The labeling of the miRNA probe was verified by 20% urea-PAGE gel. To conjugate the miRNA probe to the protein, the TCO-modified miRNA probe was mixed with Methyltetrazine-labeled protein at different molar ratios to achieve optimal protein labeling efficiency. The mixture was incubated at room temperature for 1 hour. The conjugation was verified with 12% SDS-PAGE.

Strategy 2: via Azide-Alkyne click chemistry: A 40 μL of 20 μM protein solution was prepared in a buffer containing 0.5 M NaCl, 50 mM Tris, 15% glycerol with pH 6.8. The solution was degassed, and 100-fold excess TCEP was added to the solution. After 20 min incubation, 1.6 μL of 10 mM Sulfo DBCO-PEG4-maleimide was added drop-wise to the protein solution, and the mixture was incubated in the dark at room temperature for 1 hour. Excess maleimide reagent was removed by desalting using a desalt spin column. The DBCO-modified protein was mixed with Azide-modified miRNA probe at equal molar concentration, and the reaction mixture was incubated at room temperature for 2 hours. The conjugation was verified with 12% SDS-PAGE.

Example 9

Verification of the DNA Probe Conjugated to Proteins

Figure 15:
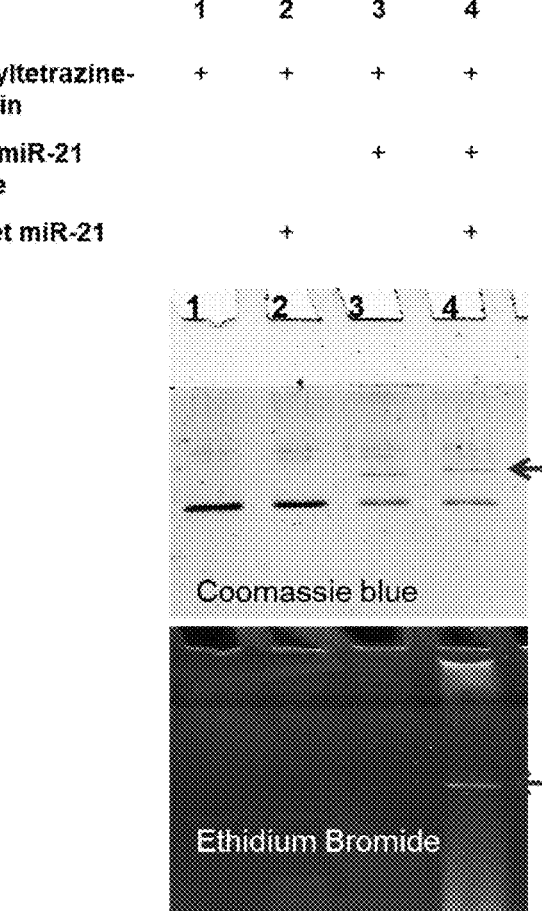
FIG. 15 shows an example of conjugating probes to non-membrane protein channels via click chemistry, as demonstrated using phi29 gp10 portal protein. The thiol-miR-21 probe was labeled with TCO (trans-cyclooctene) followed by conjugation of TCO-miR-21 probe to Methyl-tetrazine-protein. The SDS-PAGE gel verifies target miR-21 binding to miR-21 probe conjugated to proteins.

The protein-miRNA probe conjugate was incubated with the target miRNA oligo at an equal molar concentration at room temperature for 30 min. The binding of the protein-miRNA probe with the target miRNA was verified with 12% SDS-PAGE (FIG. 15).

Example 10

PSA Detection Using Engineered Non-Membrane Protein Channels

Figure 18:
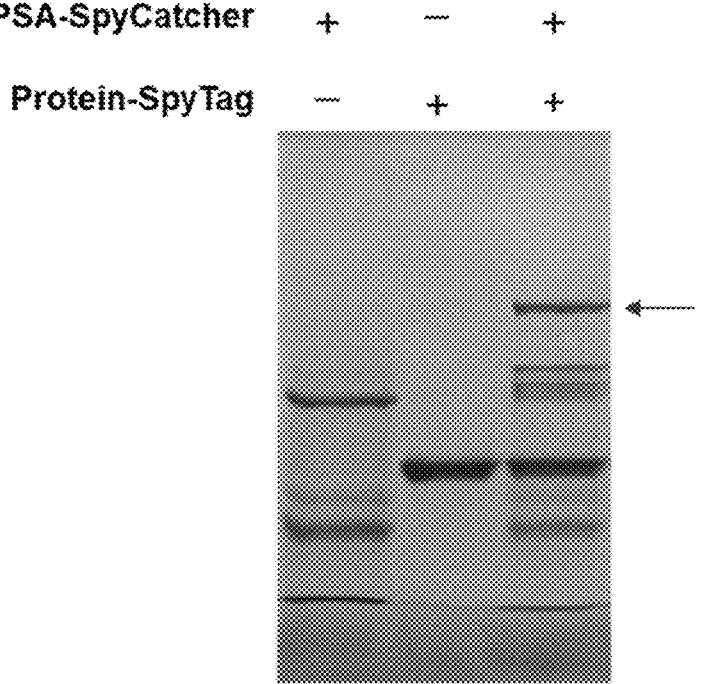
FIG. 18 shows an example of a non-membrane protein with Spytag/Spycatcher system for incorporating analyte probes, as demonstrated using phi29 gp10 portal protein. Coomassie-blue stained SDS-PAGE gel shows the binding of Spytag incorporated in phi29 gp10 portal protein and PSA-Spycatcher protein to form a complex. The functionalized pore can then be used for sensing PSA as shown in FIG. 19.

To conjugate a protein probe to the nanopore channel, various methods have been tried and tested, including reaction of cysteine residue with Methyltetrazine-PEG4-maleimide and subsequent reaction with TCO-labeled probes, and SpyCatcher/Spytag protein conjugation system. How a single chain antibody against PSA conjugate to phi29 gp10 portal protein channel via SpyCatcher/Spytag was demonstrated. Phi29 gp10 protein channel with a C-terminal Spy-Tag peptide was constructed and purified. Single chain antibody against PSA with a C-terminal SpyCatcher was constructed and purified. The assembled protein channel-PSA single chain antibody was verified by gel (FIG. 18).

Figure 19:
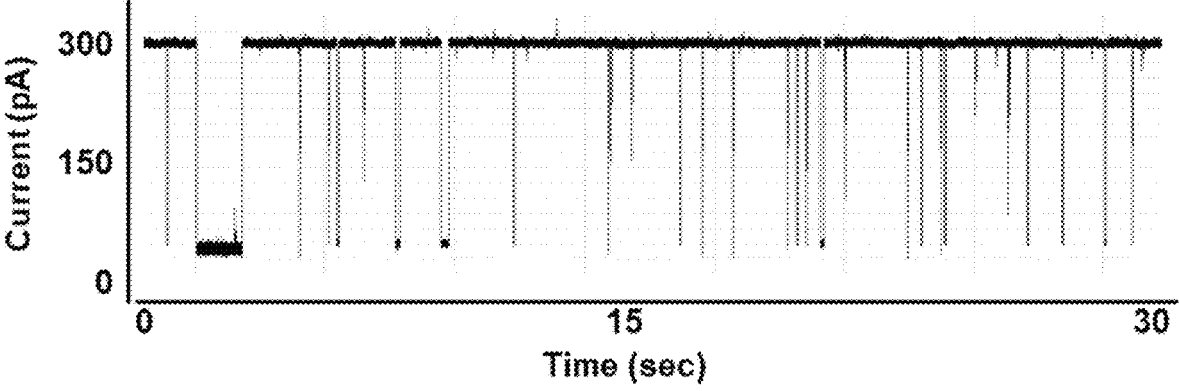
FIG. 19 shows an example of non-membrane protein channels for analyte detection using spytag-spycatcher system, as demonstrated using phi29 gp10 portal protein. After direct insertion, the spytag/spycatcher (PSA probe) on the phi29 gp10 portal was able to detect PSA (10 ng/uL) in the solution, as shown as current blockage events. Conduction buffer: 1 M KCl, 5 mM Tris, pH 7.6. Applied voltage: 100 mV. Membrane: PMOXA$_6$-PDMS$_{35}$-PMOXA$_6$.

Then the purified assembled protein channel-PSA single chain antibody was inserted into polymer membrane to test its capacity of binding PSA antigen. The procedure to setup electrophysiological experiments was described previously. After insertion, a series of different concentration of PSA antigen was added to the chamber, and a unique binding event was observed (FIG. 19).

Example 11

MicroRNA Detection Using Engineered Non-Membrane Protein Channels

Figure 16:
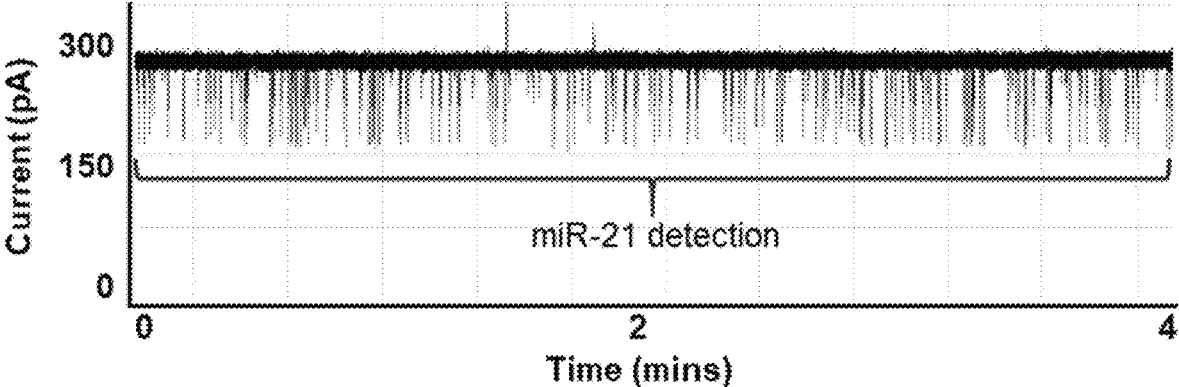
FIG. 16 shows an example of analyte (e.g., miRNA) detection using probe-functionalized non-membrane protein pores, as demonstrated using T4 gp20 portal protein. In the presence of target miRNA, current blockage events were observed, indicating detection of miRNA at the single molecule level. Conduction buffer: 1 M KCl, 5 mM Tris, pH 7.6. Applied voltage: 100 mV. Membrane: PMOXA6-PDMS35-PMOXA6.

To conjugate a nucleic probe to the nanopore channel, a variety of different methods have been tried and tested as outlined in Example 6. It was demonstrated that miR-21 probes can be conjugated to T4 gp20 portal protein channel The purified conjugated complex was inserted into a polymer membrane to test its capacity of binding corresponding microRNA. The procedure to setup electrophysiological experiments was described previously. After insertion, a series of different concentration of microRNA was added to the chamber, and a unique binding event was observed (FIG. 16).

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

---

We claim:

1. A nanopore assembly comprising a channel formed of a plurality of subunits, wherein each subunit comprises a polypeptide having the amino acid sequence of SEQ ID NO:3 that comprises at least one substitution at one or more positions independently selected from K134I, D138L, D139L, D158L, E163V, E309V, D311V, K321V, K356A, K358A, D377A, D381V, N388L, R524I, R539A, and E595V.

2. The nanopore assembly of claim 1, wherein the polypeptide comprises at least one residue substituted with cysteine.

3. The nanopore assembly of claim 1, further comprising a probe for detecting an analyte, the probe being operably linked to at least one of the subunits.

4. The nanopore assembly of claim 3, wherein the probe is selected from the group consisting of chemicals, carbohydrates, aptamers, nucleic acids, peptide, protein, antibodies, and receptors.

5. The nanopore assembly of claim 3, wherein the probe comprises a sequence at least 75% identical to a sequence selected from the group consisting of SEQ ID NOs: 36-79.

6. The nanopore assembly of claim 3, wherein the probe is an anti-PSA antibody.

7. The nanopore assembly of claim 3, wherein the analyte is selected from the group consisting of nucleic acids, amino acids, peptides, proteins, polymers, and chemical molecules.

8. The nanopore assembly of claim 3, wherein the analyte is selected from the group consisting of PSA, CEA, AFP, VCAM, MIR-155, MIR-22, MIR-7, MiR-92a, MiR-122, MiR-192, MiR-223, MiR-26a, MiR-27a, MiR-802, and PSA or a fragment thereof.

9. The nanopore assembly of claim 3, wherein the probe is operably linked via covalent bonding to at least one of the subunits, and wherein the covalent bonding optionally comprises a disulfide linkage, an ester linkage, or a sulfhydryl linkage.

10. The nanopore assembly of claim 3, wherein the probe is operably linked to a location in proximity to an entrance of the channel or a location at an interior side of the channel.

11. The nanopore assembly of claim 1, wherein the channel is embedded in a polymersome.

12. The nanopore assembly of claim 1, further comprising a membrane, wherein the channel is inserted in the membrane, and optionally at least one of cholesterol and porphyrin.

13. The nanopore assembly of claim 12, wherein the membrane comprises a polymer membrane or a lipid membrane.

14. The nanopore assembly of claim 13, wherein the polymer membrane comprises an alternating copolymer, a periodic copolymer, a block copolymer, a di-block copolymer, a tri-block copolymer, a terpolymer, or a combination thereof.

15. The nanopore assembly of claim 14, wherein the polymer membrane comprises PMOXA-PDMS-PMOXA [poly(2-methyl oxazoline)-b-poly(dimethylsiloxane)-b-poly (2-methyl oxazoline)].

16. An apparatus for detecting an analyte, comprising the nanopore assembly of claim 1 and optionally a support for the nanopore assembly.

17. A kit comprising the nanopore assembly of claim 1 and optionally instructions for using the nanopore assembly.

18. A method of detecting an analyte, comprising:

(a) contacting a sample containing an analyte with the nanopore assembly of claim 1 optionally placed on a support;

(b) applying an electrical current across the channel of the nanopore assembly;

(c) determining the electrical current passing through the channel at one or more time intervals; and (d) comparing the electrical current measured at one or more time intervals with a reference electrical current, wherein a change in electrical current relative to the reference electrical current indicates a presence of the analyte in the sample.

19. The method of claim 18, wherein the reference electrical current is measured with a sample that does not contain the analyte.

* * * * *